United States Patent
Zergiebel et al.

(10) Patent No.: US 10,849,624 B2
(45) Date of Patent: *Dec. 1, 2020

(54) ADAPTER ASSEMBLY FOR INTERCONNECTING ELECTROMECHANICAL SURGICAL DEVICES AND SURGICAL LOADING UNITS, AND SURGICAL SYSTEMS THEREOF

(71) Applicant: Covidien LP, Mansfield, MA (US)

(72) Inventors: Earl M. Zergiebel, Guilford, CT (US); David Chowaniec, Rocky Hill, CT (US); Ryan V. Williams, New Hartford, CT (US); Anand Subramanian, Stamford, CT (US)

(73) Assignee: COVIDIEN LP, Mansfield, MA (US)

( * ) Notice: Subject to any disclaimer, the term of this patent is extended or adjusted under 35 U.S.C. 154(b) by 153 days.

This patent is subject to a terminal disclaimer.

(21) Appl. No.: 16/172,215

(22) Filed: Oct. 26, 2018

(65) Prior Publication Data

US 2019/0059895 A1     Feb. 28, 2019

Related U.S. Application Data

(63) Continuation of application No. 14/822,970, filed on Aug. 11, 2015, now Pat. No. 10,123,799, which is a
(Continued)

(51) Int. Cl.
*A61B 17/072* (2006.01)
*H01R 39/08* (2006.01)
(Continued)

(52) U.S. Cl.
CPC ....... *A61B 17/07207* (2013.01); *H01R 39/08* (2013.01); *A61B 2017/0046* (2013.01);
(Continued)

(58) Field of Classification Search
CPC .... A61B 17/07207; A61B 2017/00398; A61B 2090/038; A61B 2017/0046;
(Continued)

(56) References Cited

U.S. PATENT DOCUMENTS 2,777,340 A    1/1957   Hettwer et al.
2,957,353 A    10/1960   Babacz
(Continued)

FOREIGN PATENT DOCUMENTS

CA       2451558 A1    1/2003
CA       2824590 A1    4/2014
(Continued)

OTHER PUBLICATIONS

Extended European Search Report dated Nov. 21, 2019 corresponding to counterpart Patent Application EP 19192890.2.
(Continued)

*Primary Examiner* — Nathaniel C Chukwurah
*Assistant Examiner* — Lucas E. A. Palmer

(57) ABSTRACT

The present disclosure relates to adapter assemblies for use with and to electrically and mechanically interconnect electromechanical surgical devices and surgical loading units, and to surgical systems including hand held electromechanical surgical devices and adapter assemblies for connecting surgical loading units to the hand held electromechanical surgical devices.

14 Claims, 34 Drawing Sheets

Related U.S. Application Data continuation-in-part of application No. 14/550,071, filed on Nov. 21, 2014, now Pat. No. 9,918,713, which is a continuation-in-part of application No. 14/550,183, filed on Nov. 21, 2014, now Pat. No. 10,561,417.

(60) Provisional application No. 61/913,550, filed on Dec. 9, 2013, provisional application No. 61/913,572, filed on Dec. 9, 2013.

(51) Int. Cl.
    *A61B 17/00* (2006.01)
    *A61B 90/00* (2016.01)

(52) U.S. Cl.
    CPC ......... *A61B 2017/00398* (2013.01); *A61B 2017/00473* (2013.01); *A61B 2017/00477* (2013.01); *A61B 2017/00486* (2013.01); *A61B 2017/00734* (2013.01); *A61B 2017/07271* (2013.01); *A61B 2017/07285* (2013.01); *A61B 2090/038* (2016.02); *A61B 2090/064* (2016.02); *Y10T 74/18576* (2015.01); *Y10T 74/19614* (2015.01)

(58) Field of Classification Search
    CPC ......... A61B 2017/00473; A61B 2017/00477; A61B 2017/00486; A61B 2017/00734; A61B 2017/07271; A61B 2017/07; Y10T 74/18576
    USPC ..................................... 227/175.1
    See application file for complete search history.

(56) References Cited

U.S. PATENT DOCUMENTS

| | | |
|---|---|---|
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,504,227 A | 3/1985 | Lohn |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,350,355 A * | 9/1994 | Sklar ............ A61B 17/320016 604/23 |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,433,721 A * | 7/1995 | Hooven ............ A61B 17/068 227/175.1 |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,626,587 A | 5/1997 | Bishop et al. |
| 5,632,432 A | 5/1997 | Schulze et al. |
| 5,645,209 A | 7/1997 | Green et al. |
| 5,647,526 A | 7/1997 | Green et al. |
| 5,653,374 A | 8/1997 | Young et al. |
| 5,658,300 A | 8/1997 | Bito et al. |
| 5,662,662 A | 9/1997 | Bishop et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,792,573 A | 8/1998 | Pitzen et al. |
| 5,797,536 A | 8/1998 | Smith et al. |
| 5,820,009 A | 10/1998 | Melling et al. |
| 5,863,159 A | 1/1999 | Lasko |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,165,169 A | 12/2000 | Panescu et al. |
| 6,239,732 B1 | 5/2001 | Cusey |
| 6,241,139 B1 | 6/2001 | Milliman et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,315,184 B1 | 11/2001 | Whitman |
| 6,321,855 B1 | 11/2001 | Barnes |
| 6,329,778 B1 | 12/2001 | Culp et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,434,507 B1 | 8/2002 | Clayton et al. |
| 6,443,973 B1 | 9/2002 | Whitman |
| 6,461,372 B1 | 10/2002 | Jensen et al. |
| 6,488,197 B1 | 12/2002 | Whitman |
| 6,491,201 B1 | 12/2002 | Whitman |
| 6,533,157 B1 | 3/2003 | Whitman |
| 6,537,280 B2 | 3/2003 | Dinger et al. |
| 6,610,066 B2 | 8/2003 | Dinger et al. |
| 6,611,793 B1 | 8/2003 | Burnside et al. |
| 6,645,218 B1 | 11/2003 | Cassidy et al. |
| 6,654,999 B2 | 12/2003 | Stoddard et al. |
| 6,698,643 B2 | 3/2004 | Whitman |
| 6,699,177 B1 | 3/2004 | Wang et al. |
| 6,716,233 B1 | 4/2004 | Whitman |
| 6,743,240 B2 | 6/2004 | Smith et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,860,892 B1 | 3/2005 | Tanaka et al. |
| 6,899,538 B2 | 5/2005 | Matoba |
| 6,905,057 B2 | 6/2005 | Swayze et al. |
| 6,959,852 B2 | 11/2005 | Shelton, IV et al. |

(56) References Cited

U.S. PATENT DOCUMENTS

| | | |
|---|---|---|
| 6,964,363 B2 | 11/2005 | Wales et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 7,032,798 B2 | 4/2006 | Whitman et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,111,769 B2 | 9/2006 | Wales et al. |
| 7,122,029 B2 | 10/2006 | Koop et al. |
| 7,140,528 B2 | 11/2006 | Shelton, IV |
| 7,141,049 B2 | 11/2006 | Stern et al. |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,172,104 B2 | 2/2007 | Scirica et al. |
| 7,225,964 B2 | 6/2007 | Mastri et al. |
| 7,238,021 B1 | 7/2007 | Johnson |
| 7,246,734 B2 | 7/2007 | Shelton, IV |
| 7,252,660 B2 | 8/2007 | Kunz |
| 7,328,828 B2 | 2/2008 | Ortiz et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,822,458 B2 | 10/2010 | Webster, III et al. |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,900,805 B2 | 3/2011 | Shelton, IV et al. |
| 7,905,897 B2 | 3/2011 | Whitman et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 | 6/2011 | Smith et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,011,550 B2 | 9/2011 | Aranyi et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 | 9/2011 | Whitman et al. |
| 8,035,487 B2 | 10/2011 | Malackowski |
| 8,052,024 B2 | 11/2011 | Viola et al. |
| 8,114,118 B2 | 2/2012 | Knodel et al. |
| 8,127,975 B2 | 3/2012 | Olson et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,342,379 B2 | 1/2013 | Whitman et al. |
| 8,348,130 B2 | 1/2013 | Shah et al. |
| 8,348,855 B2 | 1/2013 | Hillely et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi et al. |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,403,926 B2 | 3/2013 | Nobis et al. |
| 8,418,904 B2 | 4/2013 | Wenchell et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,523,043 B2 | 9/2013 | Ullrich et al. |
| 8,551,076 B2 | 10/2013 | Duval et al. |
| 8,561,871 B2 | 10/2013 | Rajappa et al. |
| 8,561,874 B2 | 10/2013 | Scirica |
| 8,602,287 B2 | 12/2013 | Yates et al. |
| 8,623,000 B2 | 1/2014 | Humayun et al. |
| 8,627,995 B2 | 1/2014 | Smith et al. |
| 8,632,463 B2 | 1/2014 | Drinan et al. |
| 8,636,766 B2 | 1/2014 | Milliman et al. |
| 8,647,258 B2 | 2/2014 | Aranyi et al. |
| 8,652,121 B2 | 2/2014 | Quick et al. |
| 8,657,174 B2 | 2/2014 | Yates et al. |
| 8,657,177 B2 | 2/2014 | Scirica et al. |
| 8,672,206 B2 | 3/2014 | Aranyi et al. |
| 8,696,552 B2 | 4/2014 | Whitman |
| 8,708,213 B2 | 4/2014 | Shelton, IV et al. |
| 8,715,306 B2 | 5/2014 | Faller et al. |
| 8,758,391 B2 | 6/2014 | Swayze et al. |
| 8,806,973 B2 | 8/2014 | Ross et al. |
| 8,808,311 B2 | 8/2014 | Heinrich et al. |
| 8,820,605 B2 | 9/2014 | Shelton, IV |
| 8,851,355 B2 | 10/2014 | Aranyi et al. |
| 8,858,571 B2 | 10/2014 | Shelton, IV et al. |
| 8,875,972 B2 | 11/2014 | Weisenburgh, II et al. |
| 8,888,762 B2 | 11/2014 | Whitman |
| 8,893,946 B2 | 11/2014 | Boudreaux et al. |
| 8,899,462 B2 | 12/2014 | Kostrzewski et al. |
| 8,905,289 B2 | 12/2014 | Patel et al. |
| 8,919,630 B2 | 12/2014 | Milliman |
| 8,931,680 B2 | 1/2015 | Milliman |
| 8,939,344 B2 | 1/2015 | Olson et al. |
| 8,950,646 B2 | 2/2015 | Viola |
| 8,960,519 B2 | 2/2015 | Whitman et al. |

(56) References Cited

U.S. PATENT DOCUMENTS

| | | |
|---|---|---|
| 8,961,396 B2 | 2/2015 | Azarbarzin et al. |
| 8,967,443 B2 | 3/2015 | McCuen |
| 8,968,276 B2 | 3/2015 | Zemlok et al. |
| 8,968,337 B2 | 3/2015 | Whitfield et al. |
| 8,992,422 B2 | 3/2015 | Spivey et al. |
| 9,016,545 B2 | 4/2015 | Aranyi et al. |
| 9,023,014 B2 | 5/2015 | Chowaniec et al. |
| 9,033,868 B2 | 5/2015 | Whitman et al. |
| 9,055,943 B2 | 6/2015 | Zemlok et al. |
| 9,064,653 B2 | 6/2015 | Prest et al. |
| 9,072,515 B2 | 7/2015 | Hall et al. |
| 9,113,847 B2 | 8/2015 | Whitman et al. |
| 9,113,875 B2 | 8/2015 | Viola et al. |
| 9,113,876 B2 | 8/2015 | Zemlok et al. |
| 9,113,899 B2 | 8/2015 | Garrison et al. |
| 9,216,013 B2 | 12/2015 | Scirica et al. |
| 9,282,961 B2 | 3/2016 | Whitman et al. |
| 9,282,963 B2 | 3/2016 | Bryant |
| 9,295,522 B2 | 3/2016 | Kostrzewski |
| 9,307,986 B2 | 4/2016 | Hall et al. |
| 9,351,726 B2 | 5/2016 | Leimbach |
| 9,713,466 B2 | 7/2017 | Kostrzewski |
| 9,918,713 B2 | 3/2018 | Zergiebel et al. |
| 10,123,799 B2 | 11/2018 | Zergiebel et al. |
| 2001/0031975 A1 | 10/2001 | Whitman et al. |
| 2002/0049454 A1* | 4/2002 | Whitman .............. A61B 17/072 606/139 |
| 2002/0165541 A1 | 11/2002 | Whitman |
| 2003/0038938 A1 | 2/2003 | Jung et al. |
| 2003/0165794 A1 | 9/2003 | Matoba |
| 2004/0111012 A1 | 6/2004 | Whitman |
| 2004/0133189 A1 | 7/2004 | Sakurai |
| 2004/0153124 A1 | 8/2004 | Whitman |
| 2004/0176751 A1 | 9/2004 | Weitzner et al. |
| 2004/0193146 A1 | 9/2004 | Lee et al. |
| 2005/0125027 A1 | 6/2005 | Knodel et al. |
| 2005/0131442 A1 | 6/2005 | Yachia et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |
| 2006/0273135 A1* | 12/2006 | Beetel .............. A61B 17/07207 227/175.1 |
| 2006/0278680 A1 | 12/2006 | Viola et al. |
| 2006/0284730 A1 | 12/2006 | Schmid et al. |
| 2007/0023476 A1 | 2/2007 | Whitman et al. |
| 2007/0023477 A1* | 2/2007 | Whitman .............. A61B 17/068 227/175.1 |
| 2007/0029363 A1 | 2/2007 | Popov |
| 2007/0084897 A1 | 4/2007 | Shelton et al. |
| 2007/0102472 A1 | 5/2007 | Shelton |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175956 A1* | 8/2007 | Swayze .............. A61B 34/76 227/178.1 |
| 2007/0175961 A1 | 8/2007 | Shelton et al. |
| 2007/0270784 A1 | 11/2007 | Smith et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0109012 A1 | 5/2008 | Falco et al. |
| 2008/0110958 A1 | 5/2008 | McKenna et al. |
| 2008/0147089 A1 | 6/2008 | Loh et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1* | 10/2008 | Zemlok .............. A61B 17/072 600/106 |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0012533 A1 | 1/2009 | Barbagli et al. |
| 2009/0090763 A1* | 4/2009 | Zemlok .............. A61B 90/98 227/175.2 |
| 2009/0099876 A1 | 4/2009 | Whitman |
| 2009/0108048 A1* | 4/2009 | Zemlok ............ A61B 17/00234 227/175.1 |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0206131 A1* | 8/2009 | Weisenburgh, II ......................... A61B 17/07207 227/175.2 |
| 2009/0209990 A1 | 8/2009 | Yates et al. |
| 2009/0254094 A1 | 10/2009 | Knapp et al. |
| 2009/0299141 A1 | 12/2009 | Downey et al. |
| 2009/0314821 A1* | 12/2009 | Racenet .......... A61B 17/07207 227/180.1 |
| 2010/0023022 A1 | 1/2010 | Zeiner et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0017801 A1* | 1/2011 | Zemlok .......... A61B 17/07207 227/175.1 |
| 2011/0071508 A1 | 3/2011 | Duval et al. |
| 2011/0077673 A1 | 3/2011 | Grubac et al. |
| 2011/0121049 A1* | 5/2011 | Malinouskas .......... A61B 90/92 227/175.1 |
| 2011/0125138 A1 | 5/2011 | Malinouskas et al. |
| 2011/0139851 A1* | 6/2011 | McCuen ................ A61B 34/76 227/175.1 |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174099 A1* | 7/2011 | Ross .................. A61B 17/072 74/89.32 |
| 2011/0184245 A1 | 7/2011 | Xia et al. |
| 2011/0204119 A1* | 8/2011 | McCuen .............. A61B 17/068 227/175.1 |
| 2011/0218522 A1 | 9/2011 | Whitman |
| 2011/0276057 A1 | 11/2011 | Conlon et al. |
| 2011/0290851 A1* | 12/2011 | Shelton, IV .......... B25C 5/0292 227/176.1 |
| 2011/0290854 A1* | 12/2011 | Timm .................. A61B 17/068 227/178.1 |
| 2011/0295242 A1* | 12/2011 | Spivey ................ A61B 17/068 606/1 |
| 2011/0295269 A1* | 12/2011 | Swensgard .......... A61B 34/70 606/130 |
| 2012/0000962 A1 | 1/2012 | Racenet et al. |
| 2012/0074199 A1 | 3/2012 | Olson et al. |
| 2012/0089131 A1* | 4/2012 | Zemlok ................ A61B 17/072 606/1 |
| 2012/0104071 A1* | 5/2012 | Bryant ............ A61B 17/07207 227/175.1 |
| 2012/0116368 A1 | 5/2012 | Viola |
| 2012/0138660 A1* | 6/2012 | Shelton, IV .......... A61B 34/71 227/176.1 |
| 2012/0143002 A1 | 6/2012 | Aranyi et al. |
| 2012/0172924 A1 | 7/2012 | Allen, IV |
| 2012/0211542 A1 | 8/2012 | Racenet |
| 2012/0223121 A1 | 9/2012 | Viola et al. |
| 2012/0245428 A1 | 9/2012 | Smith et al. |
| 2012/0253329 A1* | 10/2012 | Zemlok ................ A61B 17/115 606/1 |
| 2012/0310220 A1 | 12/2012 | Malkowski et al. |
| 2012/0323226 A1* | 12/2012 | Chowaniec .......... A61B 17/072 606/1 |
| 2012/0330285 A1 | 12/2012 | Hartoumbekis et al. |
| 2013/0018361 A1 | 1/2013 | Bryant |
| 2013/0093149 A1 | 4/2013 | Saur et al. |

(56) References Cited

U.S. PATENT DOCUMENTS

| | | | |
|---|---|---|---|
| 2013/0098970 A1* | 4/2013 | Racenet | A61B 17/07207 227/180.1 |
| 2013/0181035 A1 | 7/2013 | Milliman | |
| 2013/0184704 A1 | 7/2013 | Beardsley et al. | |
| 2013/0200131 A1* | 8/2013 | Racenet | A61B 17/072 227/180.1 |
| 2013/0214025 A1 | 8/2013 | Zemlok et al. | |
| 2013/0274722 A1 | 10/2013 | Kostrzewski et al. | |
| 2013/0282052 A1 | 10/2013 | Aranyi et al. | |
| 2013/0292451 A1 | 11/2013 | Viola et al. | |
| 2013/0313304 A1 | 11/2013 | Shelton, IV et al. | |
| 2013/0317486 A1 | 11/2013 | Nicholas et al. | |
| 2013/0319706 A1 | 12/2013 | Nicholas et al. | |
| 2013/0324978 A1* | 12/2013 | Nicholas | A61B 90/90 606/1 |
| 2013/0324979 A1 | 12/2013 | Nicholas et al. | |
| 2013/0334281 A1 | 12/2013 | Williams | |
| 2014/0012236 A1 | 1/2014 | Williams et al. | |
| 2014/0012237 A1 | 1/2014 | Pribanic et al. | |
| 2014/0012289 A1 | 1/2014 | Snow et al. | |
| 2014/0025046 A1 | 1/2014 | Williams et al. | |
| 2014/0110455 A1 | 4/2014 | Ingmanson et al. | |
| 2014/0207125 A1 | 7/2014 | Applegate et al. | |
| 2014/0207182 A1 | 7/2014 | Zergiebel et al. | |
| 2014/0207185 A1 | 7/2014 | Goble et al. | |
| 2014/0236173 A1 | 8/2014 | Scirica et al. | |
| 2014/0236174 A1 | 8/2014 | Williams et al. | |
| 2014/0263542 A1* | 9/2014 | Leimbach | A61B 17/0686 227/175.2 |
| 2014/0263554 A1* | 9/2014 | Leimbach | A61B 17/07207 227/176.1 |
| 2014/0263564 A1* | 9/2014 | Leimbach | A61B 17/064 227/180.1 |
| 2014/0263565 A1* | 9/2014 | Lytle, IV | A61B 34/30 227/180.1 |
| 2014/0276932 A1 | 9/2014 | Williams et al. | |
| 2014/0277017 A1* | 9/2014 | Leimbach | A61B 17/105 606/167 |
| 2014/0299647 A1 | 10/2014 | Scirica et al. | |
| 2014/0303668 A1 | 10/2014 | Nicholas et al. | |
| 2014/0352463 A1* | 12/2014 | Parihar | A61B 17/07207 74/25 |
| 2014/0358129 A1 | 12/2014 | Zergiebel et al. | |
| 2014/0361068 A1 | 12/2014 | Aranyi et al. | |
| 2014/0365235 A1 | 12/2014 | DeBoer et al. | |
| 2014/0373652 A1 | 12/2014 | Zergiebel et al. | |
| 2015/0014392 A1 | 1/2015 | Williams et al. | |
| 2015/0048144 A1 | 2/2015 | Whitman | |
| 2015/0076205 A1 | 3/2015 | Zergiebel | |
| 2015/0080912 A1 | 3/2015 | Sapre | |
| 2015/0112381 A1 | 4/2015 | Richard | |
| 2015/0122870 A1 | 5/2015 | Zemlok et al. | |
| 2015/0133224 A1 | 5/2015 | Whitman et al. | |
| 2015/0133957 A1 | 5/2015 | Kostrzewski | |
| 2015/0150547 A1 | 6/2015 | Ingmanson et al. | |
| 2015/0150574 A1 | 6/2015 | Richard et al. | |
| 2015/0157320 A1 | 6/2015 | Zergiebel et al. | |
| 2015/0157321 A1 | 6/2015 | Zergiebel et al. | |
| 2015/0164502 A1 | 6/2015 | Richard et al. | |
| 2015/0201931 A1 | 7/2015 | Zergiebel et al. | |
| 2015/0272577 A1 | 10/2015 | Zemlok et al. | |
| 2015/0297199 A1 | 10/2015 | Nicholas et al. | |
| 2015/0303996 A1 | 10/2015 | Calderoni | |
| 2015/0320420 A1 | 11/2015 | Penna et al. | |
| 2015/0327850 A1 | 11/2015 | Kostrzewski | |
| 2015/0342601 A1 | 12/2015 | Williams et al. | |
| 2015/0342603 A1 | 12/2015 | Zergiebel et al. | |
| 2015/0374366 A1 | 12/2015 | Zergiebel et al. | |
| 2015/0374370 A1 | 12/2015 | Zergiebel et al. | |
| 2015/0374371 A1 | 12/2015 | Richard et al. | |
| 2015/0374372 A1 | 12/2015 | Zergiebel et al. | |
| 2015/0374449 A1 | 12/2015 | Chowaniec et al. | |
| 2015/0380187 A1 | 12/2015 | Zergiebel et al. | |
| 2016/0095585 A1 | 4/2016 | Zergiebel et al. | |
| 2016/0095596 A1 | 4/2016 | Scirica et al. | |
| 2016/0106406 A1 | 4/2016 | Cabrera et al. | |
| 2016/0113648 A1 | 4/2016 | Zergiebel et al. | |
| 2016/0113649 A1 | 4/2016 | Zergiebel et al. | |
| 2017/0128069 A1 | 5/2017 | Richard | |
| 2017/0143337 A1 | 5/2017 | Nicholas | |
| 2017/0164946 A1 | 6/2017 | Williams | |
| 2017/0175852 A1 | 6/2017 | Nicholas | |

FOREIGN PATENT DOCUMENTS

| | | |
|---|---|---|
| CN | 102247182 A | 11/2011 |
| DE | 102008053842 A1 | 5/2010 |
| EP | 0705571 A1 | 4/1996 |
| EP | 1769754 A1 | 4/2007 |
| EP | 2044890 A1 | 4/2009 |
| EP | 2055243 A2 | 5/2009 |
| EP | 2316345 A1 | 5/2011 |
| EP | 2329773 A1 | 6/2011 |
| EP | 2333509 A1 | 6/2011 |
| EP | 2446834 A1 | 5/2012 |
| EP | 2581055 A2 | 4/2013 |
| EP | 2612609 A2 | 7/2013 |
| EP | 2668910 A2 | 12/2013 |
| EP | 2722011 A1 | 4/2014 |
| EP | 2823771 A1 | 1/2015 |
| EP | 2881046 A2 | 6/2015 |
| ES | 2333509 A1 | 2/2010 |
| JP | 08038488 | 2/1996 |
| JP | 2005125075 A | 5/2005 |
| KR | 20120022521 A | 3/2012 |
| WO | 2008121234 A2 | 10/2008 |
| WO | 2009039506 A1 | 3/2009 |
| WO | 2011108840 A2 | 9/2011 |
| WO | 2012040984 A1 | 4/2012 |

OTHER PUBLICATIONS

Australian Office Action dated Jun. 13, 2019 corresponding to counterpart Patent Application AU 2019201734.
Extended European Search Report corresponding to counterpart Int'l Appln. No. EP 16 18 3520.2 dated May 3, 2017.
European Office Action corresponding to counterpart Int'l Appln. No. EP 14 19 6704.2 dated Oct. 28, 2016.
Extended European Search Report corresponding to counterpart International Application No. EP 14 18 4882.0 dated May 12, 2015.
Canadian Office Action corresponding to counterpart International Application No. CA 2640399 dated May 7, 2015.
Japanese Office Action corresponding to counterpart International Application No. JP 2011-197365 dated Mar. 23, 2015.
Japanese Office Action corresponding to counterpart International Application No. JP 2011-084092 dated May 20, 2015.
Japanese Office Action corresponding to counterpart International Application No. JP 2014-148482 dated Jun. 2, 2015.
Extended European Search Report corresponding to counterpart International Application No. EP 14 18 9358.6 dated Jul. 8, 2015.
Extended European Search Report corresponding to counterpart International Application No. EP 14 19 6148.2 dated Apr. 23, 2015.
Partial European Search Report corresponding to counterpart International Application No. EP 14 19 6704.2 dated May 11, 2015.
Australian Office Action corresponding to counterpart International Application No. AU 2010241367 dated Aug. 20, 2015.
Partial European Search Report corresponding to counterpart International Application No. EP 14 19 97833 dated Sep. 3, 2015.
Extended European Search Report corresponding to counterpart International Application No. EP 15 16 9962.6 dated Sep. 14, 2015.
Extended European Search Report corresponding to International Application No. EP 14 19 6704.2 dated Sep. 24, 2015; (11 pp.).
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.

(56) References Cited

OTHER PUBLICATIONS

Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.
Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Partial European Search Report corresponding to counterpart Int'l Appln. No. EP 16 18 3520.2 dated Dec. 13, 2016.
Extended European Search Report corresponding to counterpart Patent Appln. EP 17 17 1082.5 dated Oct. 5, 2017.
Chinese First Office Action corresponding to counterpart Chinese patent application CN 2014107508838 dated Feb. 24, 2018.
Chinese First Office Action corresponding to counterpart Patent Appln. CN 2014107511525 dated Apr. 4, 2018.
Chinese Second Office Action corresponding to counterpart Patent Appln. CN 201410751152.5 dated Dec. 10, 2018.
Japanese Final Office Action corresponding to counterpart Patent Application JP 2014-247812 dated Jan. 18, 2019.
Chinese First Office Action dated May 6, 2020 corresponding to counterpart Patent Application CN 2016106479023.

* cited by examiner

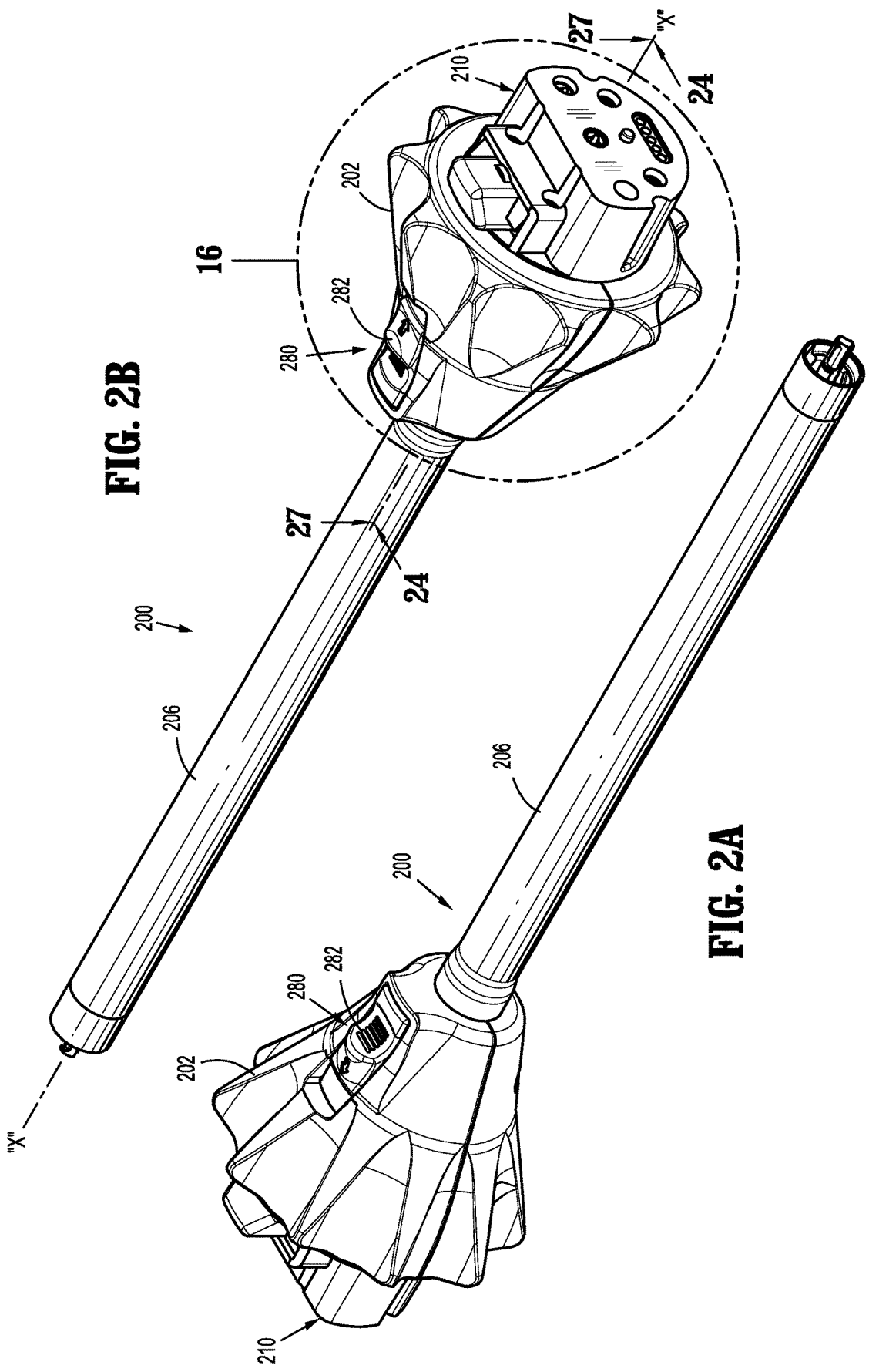

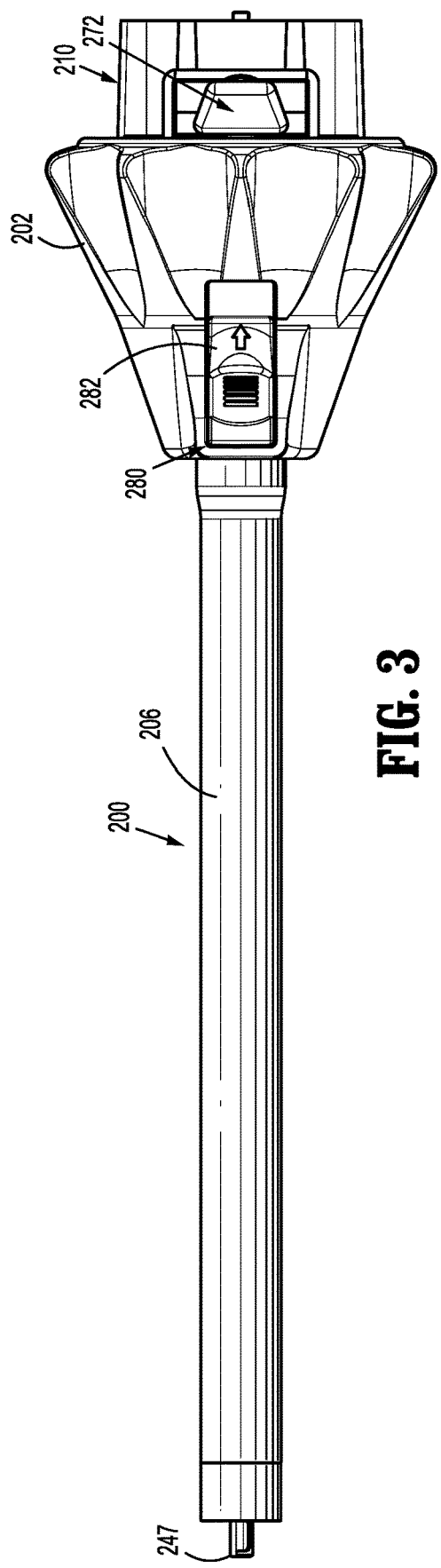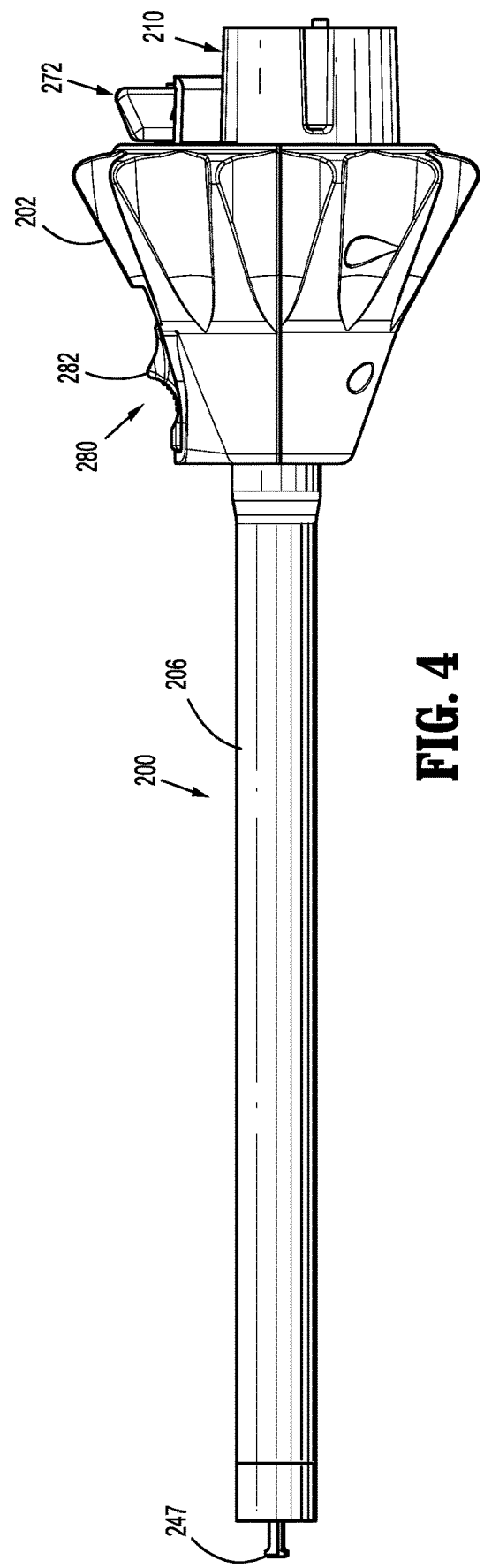

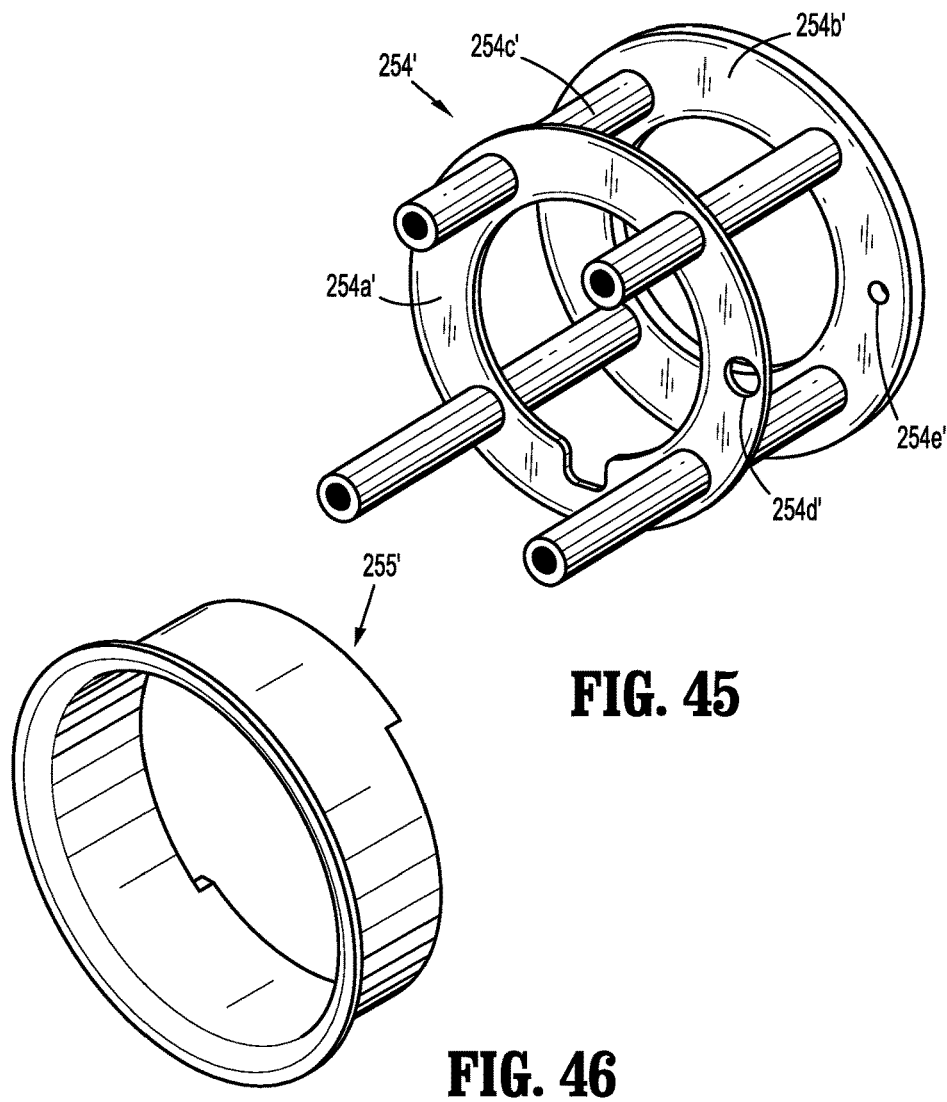
FIG. 45
FIG. 46
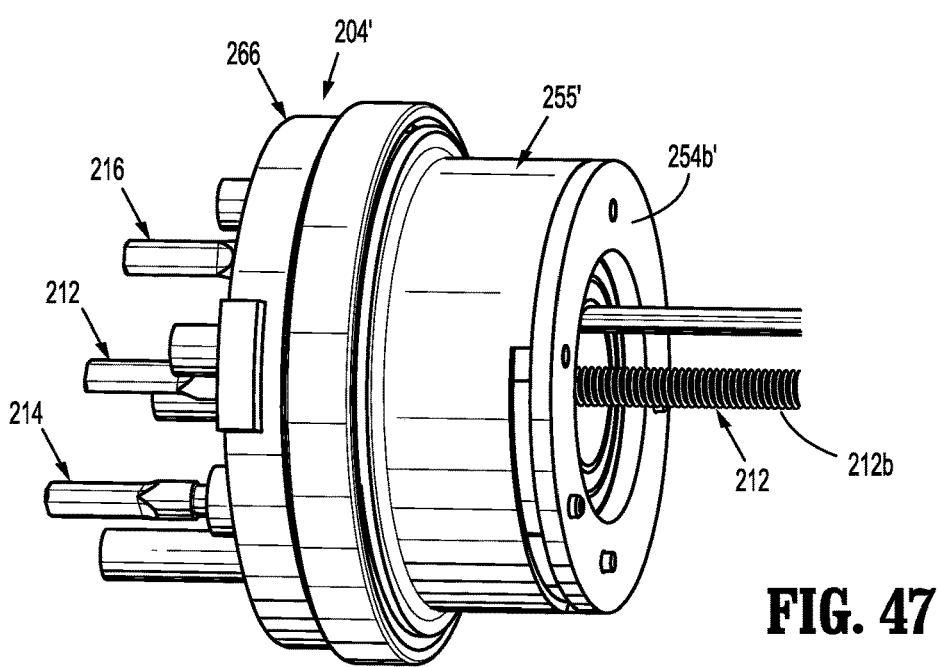
**FIG. 47

ADAPTER ASSEMBLY FOR INTERCONNECTING ELECTROMECHANICAL SURGICAL DEVICES AND SURGICAL LOADING UNITS, AND SURGICAL SYSTEMS THEREOF

CROSS-REFERENCE TO RELATED APPLICATIONS

The Present Application is a Continuation Application which claims the benefit of and priority to U.S. patent application Ser. No. 14/822,970, filed on Aug. 11, 2015, which is a Continuation-in-Part Application claiming the benefit of and priority to each of U.S. patent application Ser. No. 14/550,071, filed on Nov. 21, 2014, (now U.S. Pat. No. 9,918,713), which claims the benefit of and priority to U.S. Provisional Patent Application Ser. No. 61/913,550, filed on Dec. 9, 2013; and is a Continuation-in-Part of U.S. patent application Ser. No. 14/550,183, filed on Nov. 21, 2014, which claims the benefit of and priority to U.S. Provisional Application Ser. No. 61/913,572, filed on Dec. 9, 2013, the entire contents of each of which are incorporated herein by reference.

BACKGROUND

1. Technical Field

The present disclosure relates to adapter assemblies for use in surgical systems. More specifically, the present disclosure relates to adapter assemblies for use with and to electrically and mechanically interconnect electromechanical surgical devices and surgical loading units, and to surgical systems including hand held electromechanical surgical devices and adapter assemblies for connecting surgical loading units to the hand held electromechanical surgical devices.

2. Background of Related Art

A number of surgical device manufacturers have developed product lines with proprietary drive systems for operating and/or manipulating electromechanical surgical devices. In many instances the electromechanical surgical devices include a handle assembly, which is reusable, and disposable loading units and/or single use loading units or the like that are selectively connected to the handle assembly prior to use and then disconnected from the handle assembly following use in order to be disposed of or in some instances sterilized for re-use.

In certain instances, an adapter assembly is used to interconnect an electromechanical surgical device with any one of a number of surgical loading units to establish a mechanical and/or electrical connection therebetween. By using an adapter assembly to interconnect the electromechanical surgical device with the surgical loading units, an overall length of this electromechanical surgical system tends to be relatively greater/longer as compared to an electromechanical surgical system not using an adapter assembly. This increased length of the electromechanical surgical system (including an adapter assembly) tends to move a center of gravity of the electromechanical surgical system (including an adapter assembly) relatively distal of a center of gravity of another electromechanical surgical system (not including an adapter assembly).

With the center of gravity being located at a more distal location of the electromechanical surgical system, a torque exerted on the hand, wrist and arm of the user is increased and thus renders use of the electromechanical surgical system tiresome or cumbersome.

Accordingly, a need exists for an adapter assembly that has a relatively shorter length and that reduces the distal displacement of a center of gravity of the electromechanical surgical system.

SUMMARY

The present disclosure relates to adapter assemblies for use with and to electrically and mechanically interconnect electromechanical surgical devices and surgical loading units, and to surgical systems including hand held electromechanical surgical devices and adapter assemblies for connecting surgical loading units to the hand held electromechanical surgical devices.

According to an aspect of the present disclosure, an adapter assembly for selectively interconnecting a surgical loading unit that is configured to perform a function and a surgical device that is configured to actuate the loading unit, is provided. The loading unit may include at least one axially translatable drive member, and the surgical device may include at least one rotatable drive shaft. The adapter assembly may include a housing configured and adapted for connection with the surgical device and configured and adapted to be in operative communication with each rotatable drive shaft of the surgical device; an outer tube having a proximal end supported by the housing and a distal end configured and adapted for connection with the loading unit, wherein the distal end of the outer tube is in operative communication with each of the axially translatable drive member of the loading unit; and the force/rotation transmitting/converting assembly for interconnecting a respective one drive shaft of the surgical device and a respective one axially translatable drive member of the loading unit. The force/rotation transmitting/converting assembly may include a proximal rotation receiving member that is connectable to the respective drive shaft of the surgical device defining a threaded distal end; and a distal force transmitting member that is connectable to an articulation link of the axially translatable drive member of the loading unit. The distal force transmitting member may include a bearing assembly having an outer race threadably connected to the threaded distal end of the proximal drive shaft and an inner race; a distal articulation bar having a proximal end and a distal end, the distal end of the distal articulation bar being configured to selectively engage the axially translatable drive member of the loading unit; a proximal articulation bar having a proximal end and a distal end, the distal end of the proximal articulation bar being secured to the proximal end of the distal articulation bar; and a collar integrally supported at the proximal end of the proximal articulation bar, the collar having an outer diameter substantially equal to an outer diameter of the inner race of the bearing assembly; wherein the force/rotation transmitting/converting assembly converts and transmits a rotation of the rotatable drive shaft of the surgical device to an axial translation of the axially translatable drive member of the loading unit.

The proximal articulation bar may include a transition portion integrally supporting the collar at a proximal end thereof and a body portion at a distal end thereof, the transition portion defining an outer diameter that is greater than an outer diameter of the body portion.

The outer diameter of the collar may be greater than the outer diameter of the transition portion such that the distal articulation bar and the proximal articulation bar resist bending during use.

The distal end of the proximal articulation bar may define a cut-out configured for mating with the proximal end of the distal articulation bar.

The outer race of the bearing assembly may include a first through hole and a second through hole, the first and second through holes intersecting to define a cavity in the outer race configured for housing a ball having a threaded bore formed therein, the threaded bore configured for threadably connecting to the threaded distal end of the proximal drive shaft.

According to another aspect of the present disclosure, an adapter assembly for selectively interconnecting a surgical loading unit that is configured to perform a function and a surgical device that is configured to actuate the loading unit, is provided. The loading unit may include at least one axially translatable drive member, and the surgical device may include at least one rotatable drive shaft. The adapter assembly may include a housing configured and adapted for connection with the surgical device and configured and adapted to be in operative communication with each rotatable drive shaft of the surgical device; an outer tube having a proximal end supported by the housing and a distal end configured and adapted for connection with the loading unit, wherein the distal end of the outer tube is in operative communication with each of the axially translatable drive member of the loading unit; and the force/rotation transmitting/converting assembly for interconnecting a respective one drive shaft of the surgical device and a respective one axially translatable drive member of the loading unit. The force/rotation transmitting/converting assembly may include a proximal rotation receiving member that is connectable to a respective rotatable drive shaft of the surgical device, the proximal rotation receiving member defining a threaded distal end; and a distal force transmitting member that is connectable to an articulation link of the axially translatable drive member of the loading unit. The distal force transmitting member may include an articulation bar extending longitudinally between a proximal end and a distal end, the distal end of the articulation bar being configured to selectively engage the axially translatable drive member of the loading unit; a bearing assembly having an outer race threadably connected to the threaded distal end of the proximal drive shaft, and an inner race; and an inner sleeve supported in the inner race of the bearing assembly and extending axially from the inner race, the inner sleeve including an inner diameter and an outer diameter, the outer diameter defining a slot configured for disposal of the proximal end of the articulation bar such that the proximal end of the articulation bar is disposed between the inner race of the bearing assembly and the outer diameter of the inner sleeve; wherein the force/rotation transmitting/converting assembly converts and transmits a rotation of the rotatable drive shaft of the surgical device to an axial translation of the axially translatable drive member of the loading unit.

The housing may include a slip ring cannula disposed within the inner sleeve such that an outer diameter of the slip ring cannula engages the inner diameter of the inner sleeve utilizing an interference fit.

The outer race of the bearing assembly may include a first through hole and a second through hole, the first and second through holes intersecting to define a cavity in the outer race configured for housing a ball having a threaded bore formed therein, the threaded bore configured for threadably connecting to the threaded distal end of the proximal drive shaft.

According to another aspect of the present disclosure, an adapter assembly for selectively interconnecting a surgical loading unit that is configured to perform a function and a surgical device that is configured to actuate the loading unit, is provided. The loading unit may include at least one axially translatable drive member, and the surgical device may include at least one rotatable drive shaft. The adapter assembly may include a housing configured and adapted for connection with the surgical device and configured and adapted to be in operative communication with each rotatable drive shaft of the surgical device; an outer tube having a proximal end supported by the housing and a distal end configured and adapted for connection with the loading unit, wherein the distal end of the outer tube is in operative communication with each of the axially translatable drive member of the loading unit; and the force/rotation transmitting/converting assembly for interconnecting a respective one drive shaft of the surgical device and a respective one axially translatable drive member of the loading unit. The at least one force/rotation transmitting/converting assembly may include a proximal rotation receiving member that is connectable to a respective rotatable drive shaft of the surgical device, the proximal rotation receiving member defining at least one spur gear; a driver including an outer surface defining at least one spur gear configured for mating with the spur gear of the proximal rotation receiving member, the driver defining a bore therethrough, the bore having an inner surface defining at least one thread; and a distal force transmitting member that is connectable to an articulation link of the axially translatable drive member of the loading unit. The distal force transmitting member may include a sleeve having an outer surface defining at least one thread configured to mate with the inner surface of the driver; and an articulation bar having a proximal end secured to the sleeve and a distal end configured to selectively engage the axially translatable drive member of the loading unit; wherein the force/rotation transmitting/converting assembly converts and transmits a rotation of the rotatable drive shaft of the surgical device to a rotation of the driver such that the sleeve of the distal force transmitting member is axially translated resulting in an axial translation of the axially translatable drive member of the loading unit.

The housing may include a distal plate having a first through hole configured for locating a distal boss of the driver such that the driver is mounted co-axial to the longitudinal axis.

The distal plate may include a second through hole configured for locating a distal protrusion of the proximal rotation receiving member such that when the distal boss of the driver is located in the first through hole and the distal protrusion of the proximal rotation receiving member is located in the second through hole, the at least one spur gear of the driver is mated with the at least one spur gear of the proximal rotation receiving member.

The housing may define a proximal core portion configured for location a proximal boss of the driver such that the driver is mounted co-axial to the longitudinal axis.

The sleeve defines a bore therethrough which defines an inner surface, and wherein the proximal end of the articulation bar is secured to the inner surface of the sleeve.

BRIEF DESCRIPTION OF THE DRAWINGS

Embodiments of the present disclosure are described herein with reference to the accompanying drawings, wherein:

FIG. 2A is a front, perspective view of the adapter assembly of the present disclosure;

FIG. 2B is a rear, perspective view of the adapter assembly of FIG. 2A;

FIG. 3 is a top plan view of the adapter assembly of FIGS. 2A and 2B;

FIG. 4 is a side, elevational view of the adapter assembly of FIGS. 2A and 2B;

FIG. 45 is a perspective view of a bracket assembly of the inner housing assembly of FIGS. 43 and 44;

FIG. 46 is a perspective view of a reinforcing sleeve for use with the inner housing assembly of FIGS. 43 and 44;

FIG. 47 is a perspective view of the inner housing assembly of FIGS. 43 and 44, illustrating the reinforcing sleeve of FIG. 46 supported thereon;

DETAILED DESCRIPTION OF EMBODIMENTS

Figure 1A:
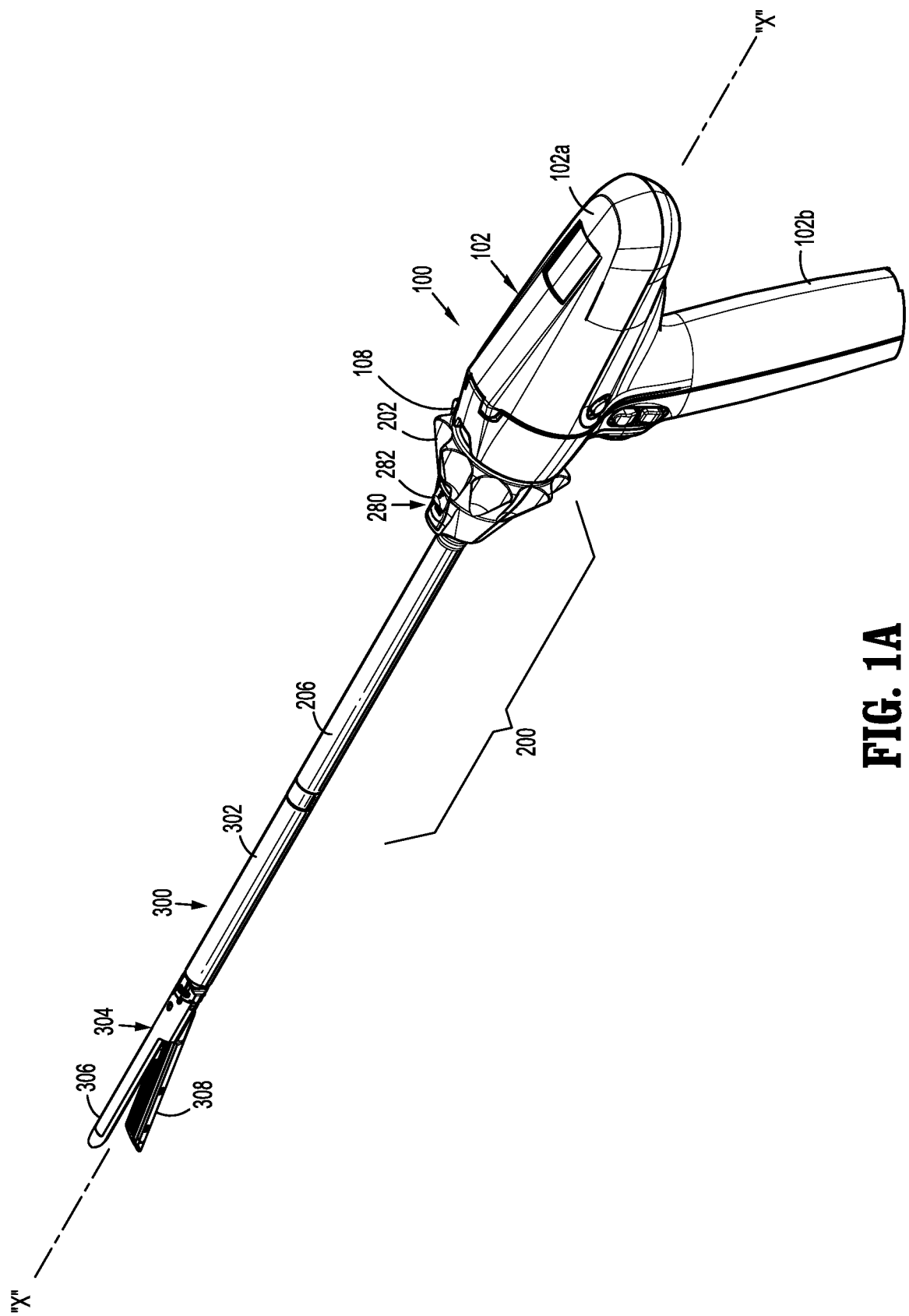
FIG. 1A is a perspective view of an adapter assembly, in accordance with an embodiment of the present disclosure, interconnected between an exemplary electromechanical surgical device and an end effector assembly.

Embodiments of the presently disclosed surgical devices, adapter assemblies, and loading unit detection assemblies for surgical devices and/or handle assemblies are described in detail with reference to the drawings, in which like reference numerals designate identical or corresponding elements in each of the several views. As used herein the term "distal" refers to that portion of the adapter assembly or surgical device, or component thereof, farther from the user, while the term "proximal" refers to that portion of the adapter assembly or surgical device, or component thereof, closer to the user.

A surgical device, in accordance with an embodiment of the present disclosure, is generally designated as 100, and is in the form of a powered hand held electromechanical instrument configured for selective attachment thereto of a plurality of different end effectors that are each configured for actuation and manipulation by the powered hand held electromechanical surgical instrument.

Figure 48:
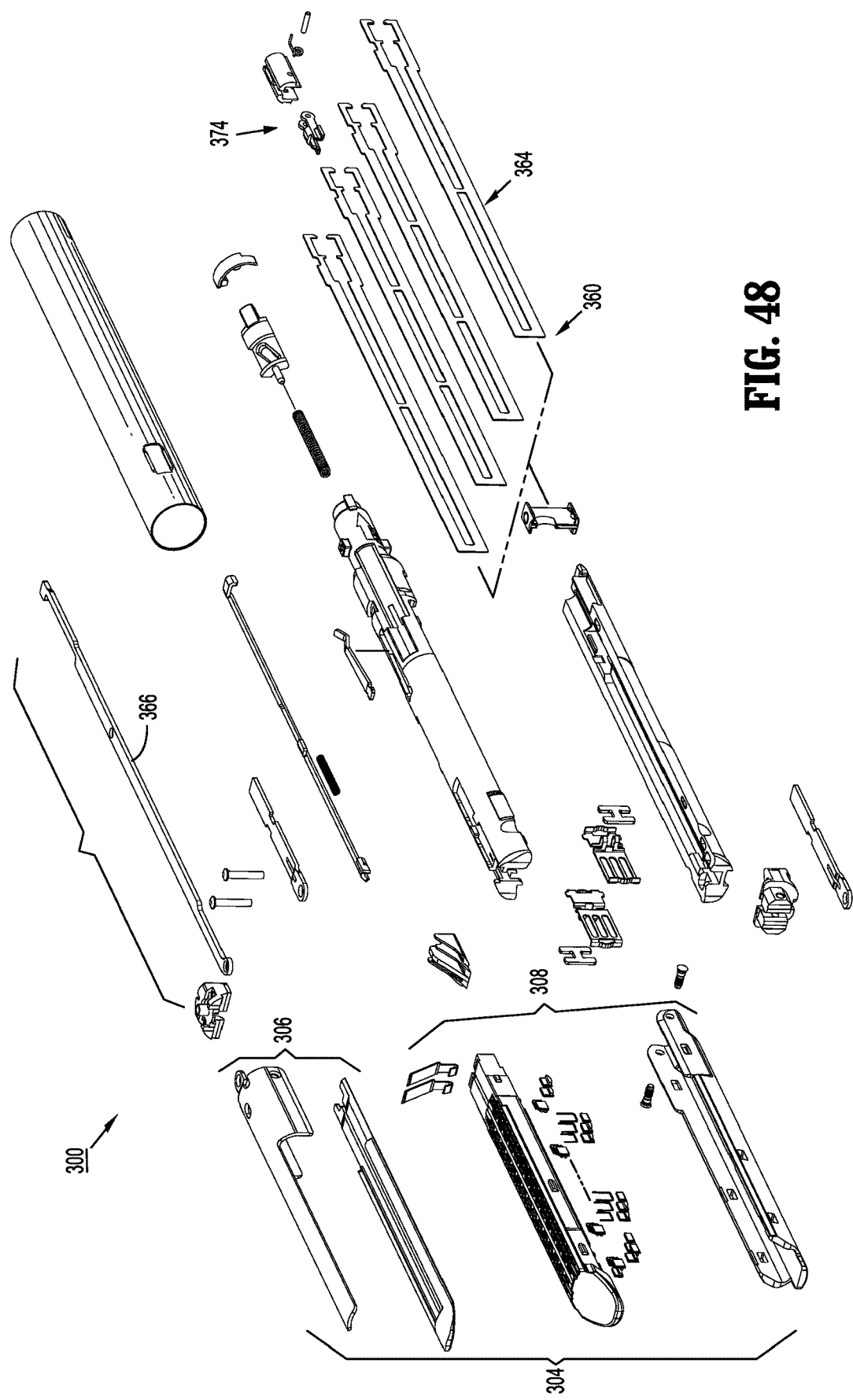
FIG. 48 is a perspective view, with parts separated, of an exemplary loading unit for use with the surgical device and the adapter of the present disclosure.

As illustrated in FIG. 1A, surgical device 100 is configured for selective connection with an adapter assembly 200, and, in turn, adapter assembly 200 is configured for selective connection with a loading unit 300 (e.g., an end effector, multiple- or single-use loading unit, see FIG. 48). Surgical device 100 and adapter assembly 200, together, may comprise an electromechanical surgical system that is configured and adapted to selectively connect with a loading unit 300 and to actuate loading unit 300.

Figure 1B:
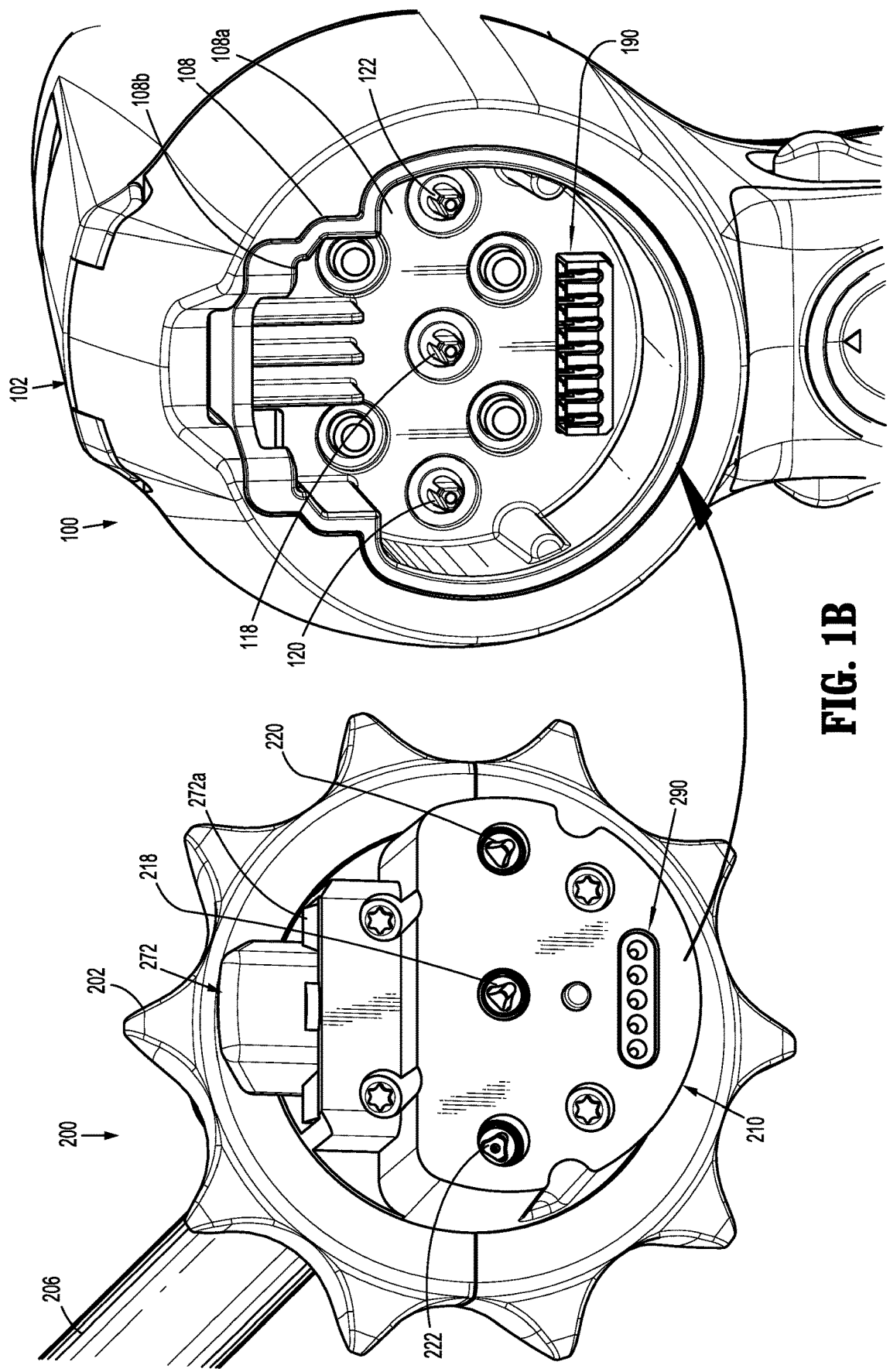
FIG. 1B is a perspective view illustrating an attachment of a proximal end of the adapter assembly to a distal end of the electromechanical surgical device.
Figure 5:
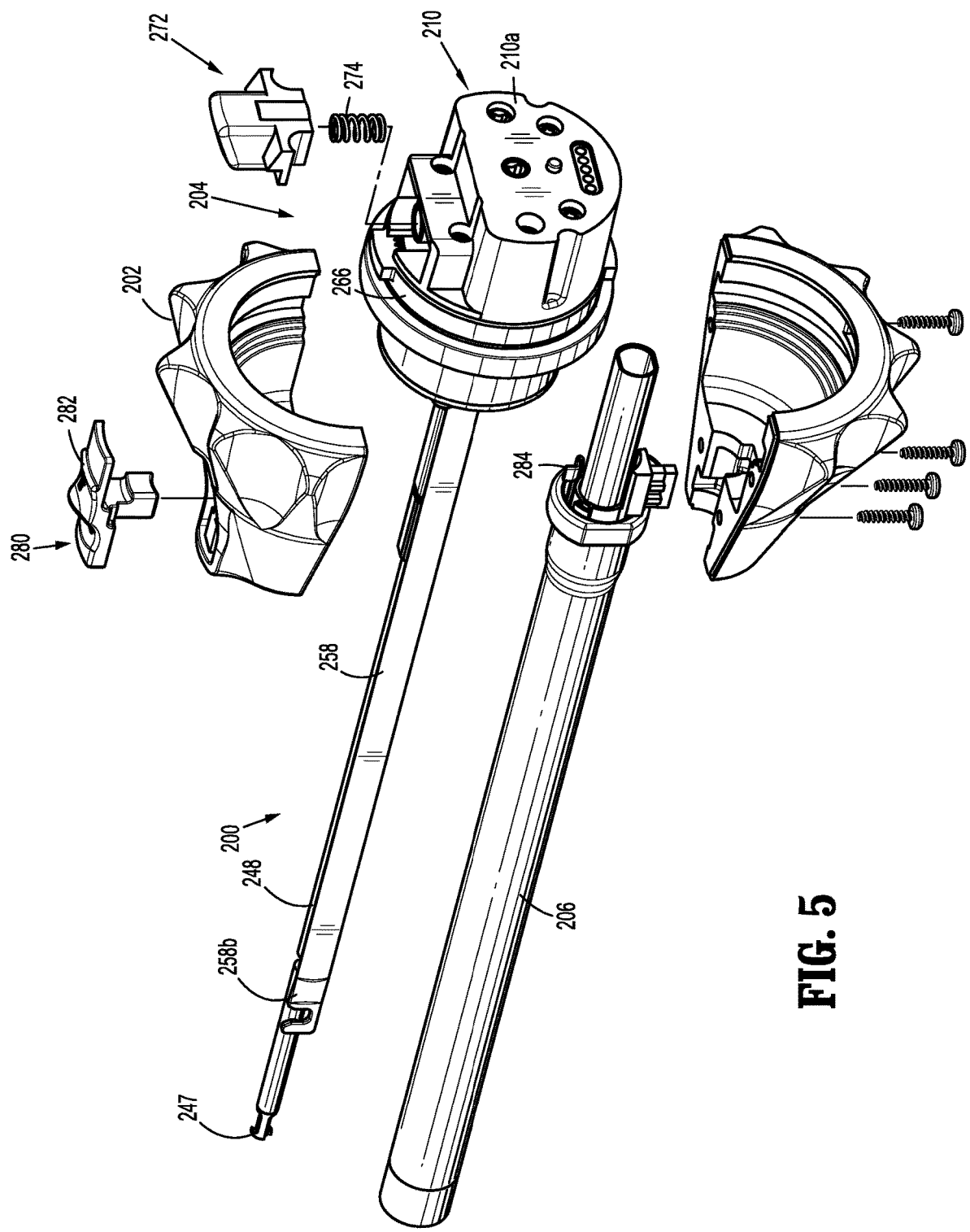
FIG. 5 is a rear, perspective view of the adapter assembly of FIGS. 2A and 2B, with some parts thereof separated.

As illustrated in FIGS. 1A and 1B, surgical device 100 includes a handle housing 102 including a circuit board (not shown) and a drive mechanism (not shown) is situated therein. The circuit board is configured to control the various operations of surgical device 100. Handle housing 102 defines a cavity therein (not shown) for selective removable receipt of a rechargeable battery (not shown) therein. The battery is configured to supply power to any of the electrical components of surgical device 100.

Handle housing 102 includes an upper housing portion 102a which houses various components of surgical device 100, and a lower hand grip portion 102b extending from upper housing portion 102a. Lower hand grip portion 102b may be disposed distally of a proximal-most end of upper housing portion 102a. The location of lower housing portion 102b relative to upper housing portion 102a is selected to balance a weight of a surgical device 100 that is connected to or supporting adapter assembly 200 and/or end effector 300.

Handle housing 102 provides a housing in which the drive mechanism is situated. The drive mechanism is configured to drive shafts and/or gear components in order to perform the various operations of surgical device 100. In particular, the drive mechanism is configured to drive shafts and/or gear components in order to selectively move a tool assembly 304 of loading unit 300 (see FIGS. 1 and 48) relative to a proximal body portion 302 of loading unit 300, to rotate loading unit 300 about a longitudinal axis "X" (see FIG. 1A) relative to handle housing 102, to move/approximate an anvil assembly 306 and a cartridge assembly 308 of loading unit 300 relative to one another, and/or to fire a stapling and cutting cartridge within cartridge assembly 308 of loading unit 300.

As illustrated in FIG. 1B, handle housing 102 defines a connecting portion 108 configured to accept a corresponding drive coupling assembly 210 of adapter assembly 200. Specifically, connecting portion 108 of surgical device 100 has a recess 108a that receives a proximal cap 210a (FIG. 6) of drive coupling assembly 210 of adapter assembly 200 when adapter assembly 200 is mated to surgical device 100. Connecting portion 108 houses three rotatable drive connectors 118, 120, 122 which are arranged in a common plane or line with one another.

When adapter assembly 200 is mated to surgical device 100, each of rotatable drive connectors 118, 120, 122 of surgical device 100 couples with a corresponding rotatable connector sleeve 218, 220, 222 of adapter assembly 200. (see FIG. 1B). In this regard, the interface between corresponding first drive connector 118 and first connector sleeve 218, the interface between corresponding second drive connector 120 and second connector sleeve 220, and the interface between corresponding third drive connector 122 and third connector sleeve 222 are keyed such that rotation of each of drive connectors 118, 120, 122 of surgical device 100 causes a corresponding rotation of the corresponding connector sleeve 218, 220, 222 of adapter assembly 200.

The mating of drive connectors 118, 120, 122 of surgical device 100 with connector sleeves 218, 220, 222 of adapter assembly 200 allows rotational forces to be independently transmitted via each of the three respective connector interfaces. The drive connectors 118, 120, 122 of surgical device 100 are configured to be independently rotated by the drive mechanism of surgical device 100. In this regard, a function selection module (not shown) of the drive mechanism selects which drive connector or connectors 118, 120, 122 of surgical device 100 is to be driven by the motor of surgical device 100.

Since each of drive connectors 118, 120, 122 of surgical device 100 has a keyed and/or substantially non-rotatable interface with respective connector sleeves 218, 220, 222 of adapter assembly 200, when adapter assembly 200 is coupled to surgical device 100, rotational force(s) are selectively transferred from drive connectors of surgical device 100 to adapter assembly 200.

The selective rotation of drive connector(s) 118, 120 and/or 122 of surgical device 100 allows surgical device 100 to selectively actuate different functions of loading unit 300. For example, selective and independent rotation of first drive connector 118 of surgical device 100 corresponds to the selective and independent opening and closing of tool assembly 304 of loading unit 300, and driving of a stapling/cutting component of tool assembly 304 of loading unit 300. As an additional example, the selective and independent rotation of second drive connector 120 of surgical device 100 corresponds to the selective and independent articulation of tool assembly 304 of loading unit 300 transverse to longitudinal axis "X" (see FIG. 1A). Additionally, for instance, the selective and independent rotation of third drive connector 122 of surgical device 100 corresponds to the selective and independent rotation of loading unit 300 about longitudinal axis "X" (see FIG. 1A) relative to handle housing 102 of surgical device 100.

As illustrated in FIG. 1A, handle housing 102 supports a plurality of finger-actuated control buttons, rocker devices and the like for activating various functions of surgical device 100.

Reference may be made to International Application No. PCT/US2008/077249, filed Sep. 22, 2008 (Inter. Pub. No. WO 2009/039506) and U.S. patent application Ser. No. 12/622,827, filed on Nov. 20, 2009, the entire content of each of which being incorporated herein by reference, for a detailed description of various internal components of and operation of exemplary electromechanical, hand-held, powered surgical instrument 100.

Turning now to FIGS. 1A-47, adapter assembly 200 includes an outer knob housing 202 and an outer tube 206 extending from a distal end of knob housing 202. Knob housing 202 and outer tube 206 are configured and dimensioned to house the components of adapter assembly 200. Outer tube 206 is dimensioned for endoscopic insertion, in particular, that outer tube is passable through a typical trocar port, cannula or the like. Knob housing 202 is dimensioned to not enter the trocar port, cannula of the like. Knob housing 202 is configured and adapted to connect to connecting portion 108 of handle housing 102 of surgical device 100.

Adapter assembly 200 is configured to convert a rotation of either of drive connectors 118 and 120 of surgical device 100 into axial translation useful for operating a drive assembly 360 and an articulation link 366 of loading unit 300, as illustrated in FIG. 48 and as will be described in greater detail below. As illustrated in FIGS. 5, 6, 13, 14, 17, 18, 20, 25-34 and 37-40, adapter assembly 200 includes a proximal inner housing assembly 204 rotatably supporting a first rotatable proximal drive shaft 212, a second rotatable proximal drive shaft 214, and a third rotatable proximal drive shaft 216 therein. Each proximal drive shaft 212, 214, 216 functions as a rotation receiving member to receive rotational forces from respective drive shafts of surgical device 100, as described in greater detail below.

As described briefly above, inner housing assembly 204 of shaft assembly 200 is also configured to rotatably support first, second and third connector sleeves 218, 220 and 222, respectively, arranged in a common plane or line with one another. Each of connector sleeves 218, 220, 222 is configured to mate with respective first, second and third drive connectors 118, 120, 122 of surgical device 100, as described above. Each of connector sleeves 218, 220, 222 is further configured to mate with a proximal end of respective first, second and third proximal drive shafts 212, 214, 216.

Inner housing assembly 204 also includes, as illustrated in FIGS. 6, 17, 27 and 28, a first, a second and a third biasing member 224, 226 and 228 disposed distally of respective first, second and third connector sleeves 218, 220, 222. Each of biasing members 224, 226 and 228 is disposed about respective first, second and third rotatable proximal drive shaft 212, 214 and 216. Biasing members 224, 226 and 228 act on respective connector sleeves 218, 220 and 222 to help maintain connector sleeves 218, 220 and 222 engaged with the distal end of respective drive rotatable drive connectors 118, 120, 122 of surgical device 100 when adapter assembly 200 is connected to surgical device 100.

In particular, first, second and third biasing members 224, 226 and 228 function to bias respective connector sleeves 218, 220 and 222 in a proximal direction. In this manner, during assembly of adapter assembly 200 to surgical device 100, if first, second and or third connector sleeves 218, 220 and/or 222 is/are misaligned with the drive connectors 118, 120, 122 of surgical device 100, first, second and/or third biasing member(s) 224, 226 and/or 228 are compressed. Thus, when surgical device 100 is operated, drive connectors 118, 120, 122 of surgical device 100 will rotate and first, second and/or third biasing member(s) 224, 226 and/or 228 will cause respective first, second and/or third connector sleeve(s) 218, 220 and/or 222 to slide back proximally, effectively coupling drive connectors 118, 120, 122 of surgical device 100 to first, second and/or third proximal drive shaft(s) 212, 214 and 216 of inner housing assembly 204.

Adapter assembly 200 includes a plurality of force/rotation transmitting/converting assemblies, each disposed within inner housing assembly 204 and outer tube 206. Each force/rotation transmitting/converting assembly is configured and adapted to transmit/convert a speed/force of rotation (e.g., increase or decrease) of first, second and third rotatable drive connectors 118, 120 and 122 of surgical instrument 100 before transmission of such rotational speed/force to loading unit 300.

Figure 6:
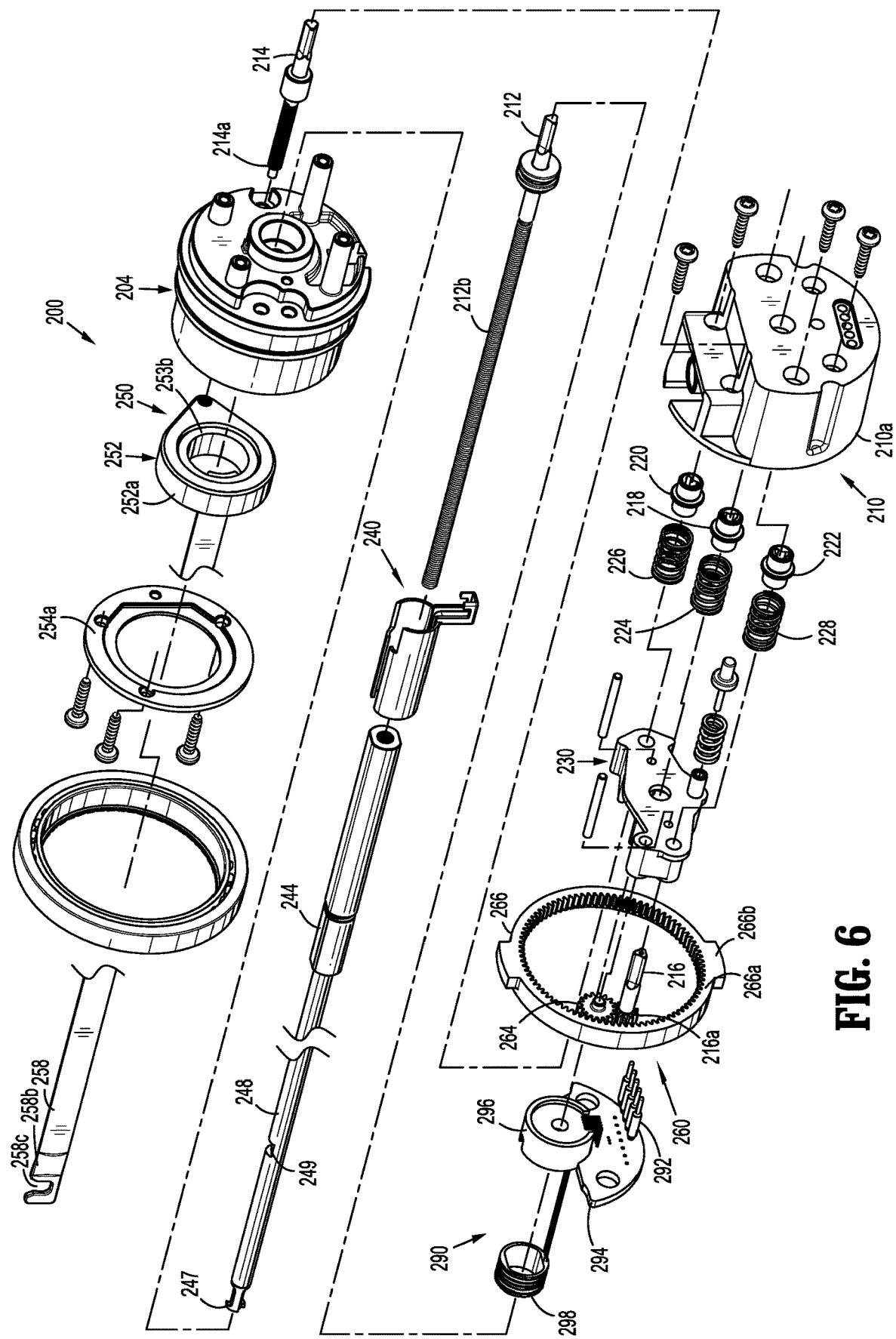
FIG. 6 is a rear, perspective view of the adapter assembly of FIGS. 2A and 2B, with most parts thereof separated.
Figure 7:
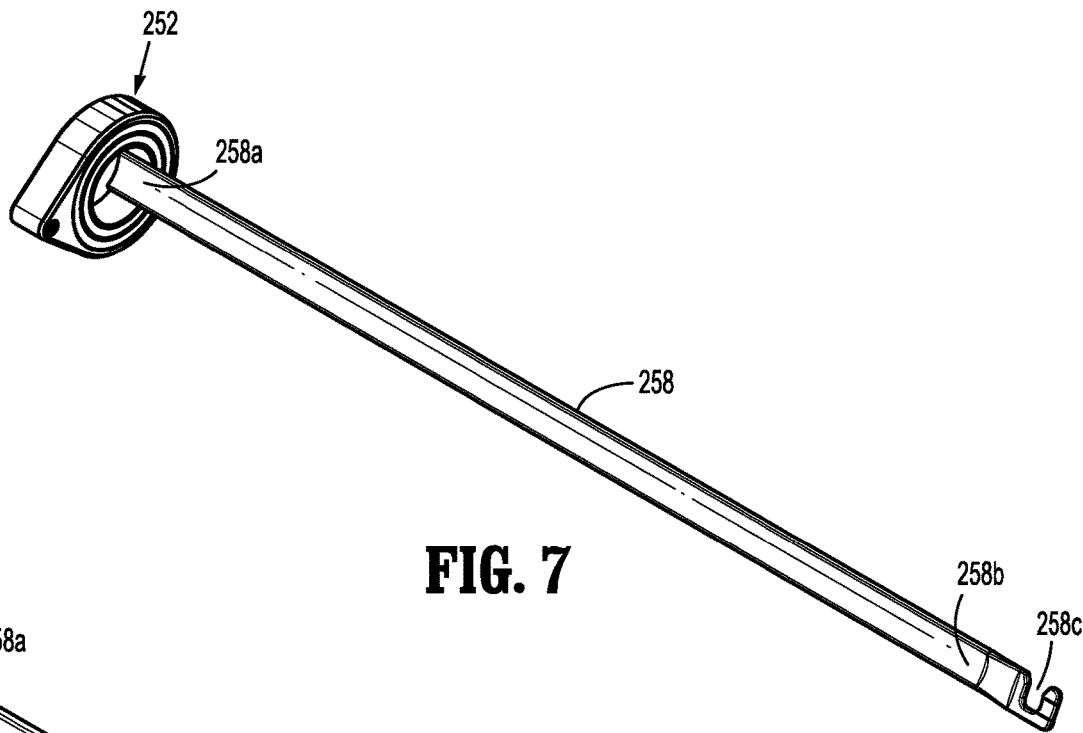
FIG. 7 is a perspective view of an articulation assembly of the adapter assembly of FIGS. 2A and 2B.
Figure 8:
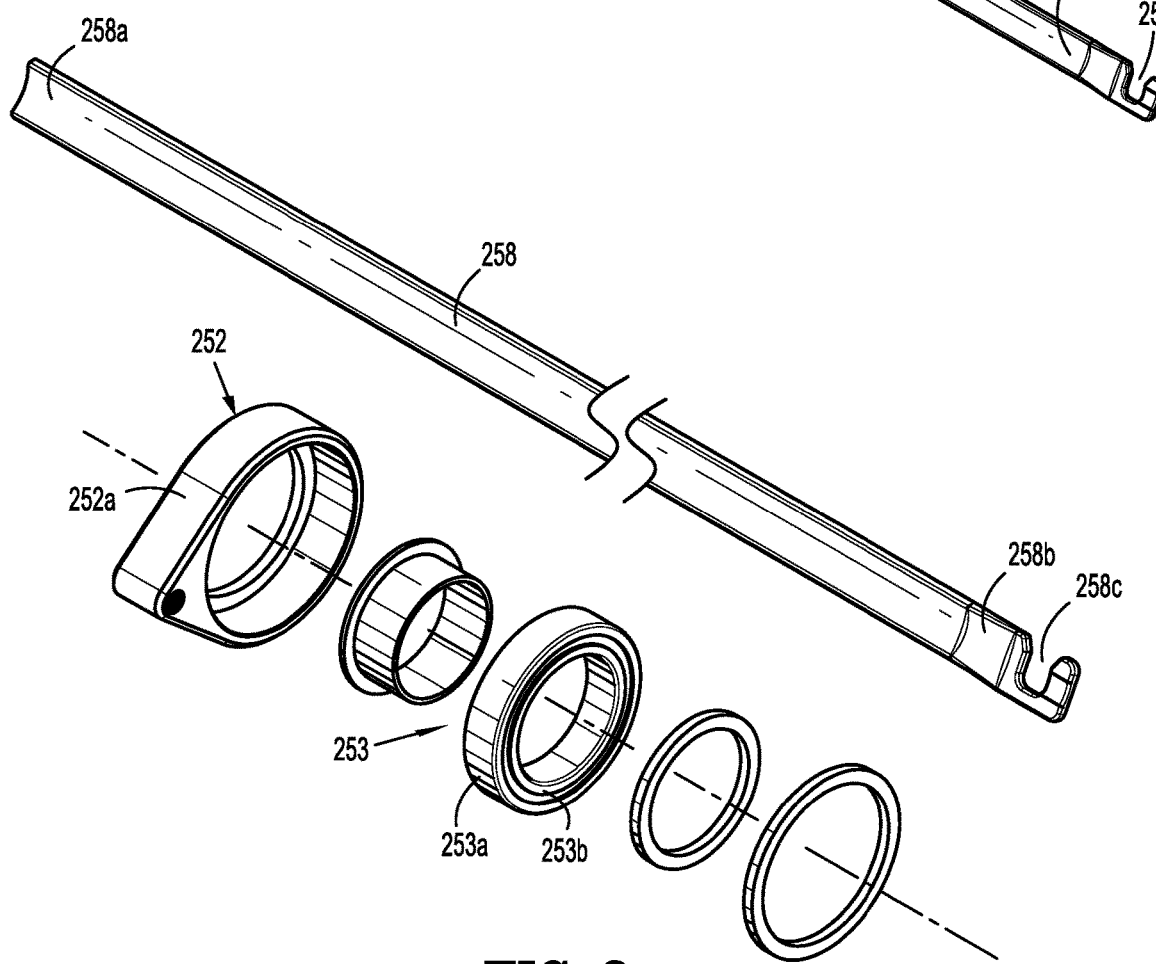
FIG. 8 is an enlarged, perspective view, with parts separated, of the articulation assembly of FIG. 7.
Figure 9:
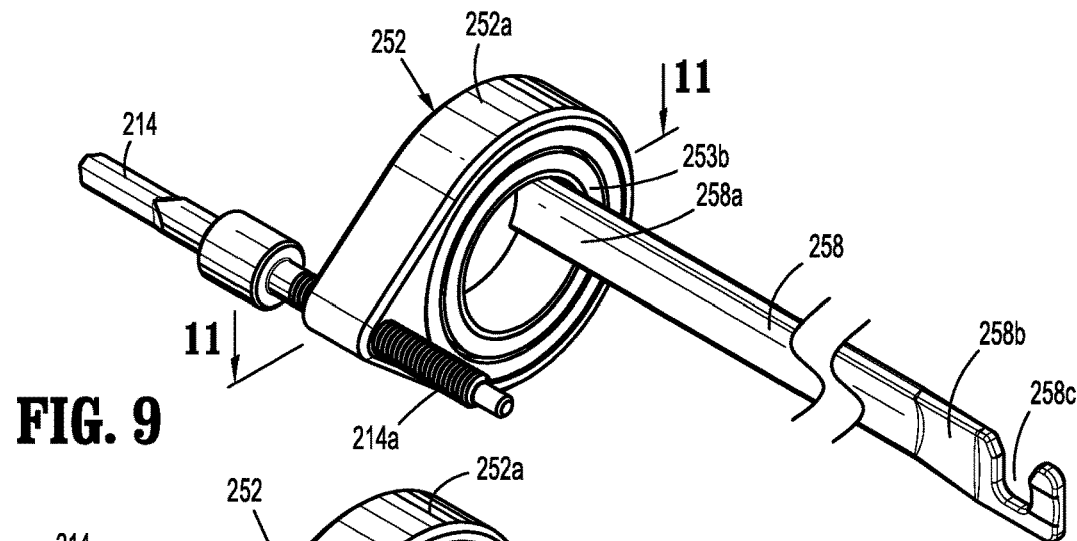
FIG. 9 is a perspective view of the articulation assembly of FIG. 7, shown in a first orientation.
Figure 10:
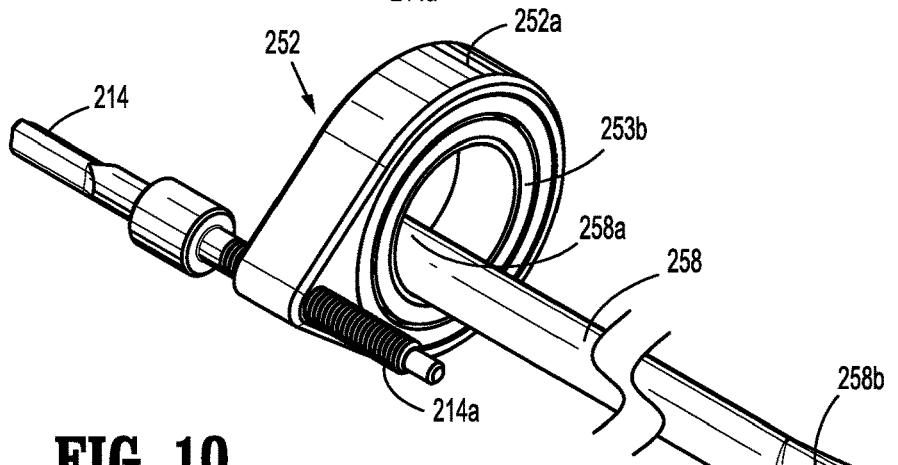
FIG. 10 is a perspective view of the articulation assembly of FIG. 7, shown in a second orientation.
Figure 11:
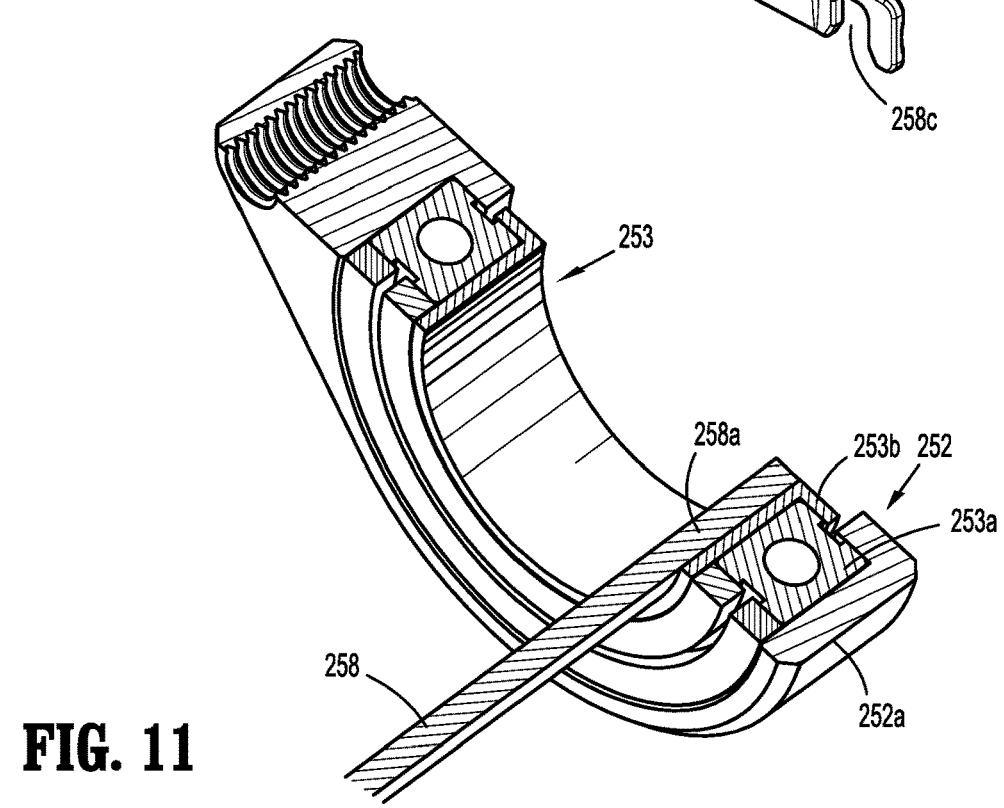
FIG. 11 is a cross-sectional view as taken along section line 11-11 of FIG. 9.
Figure 12:
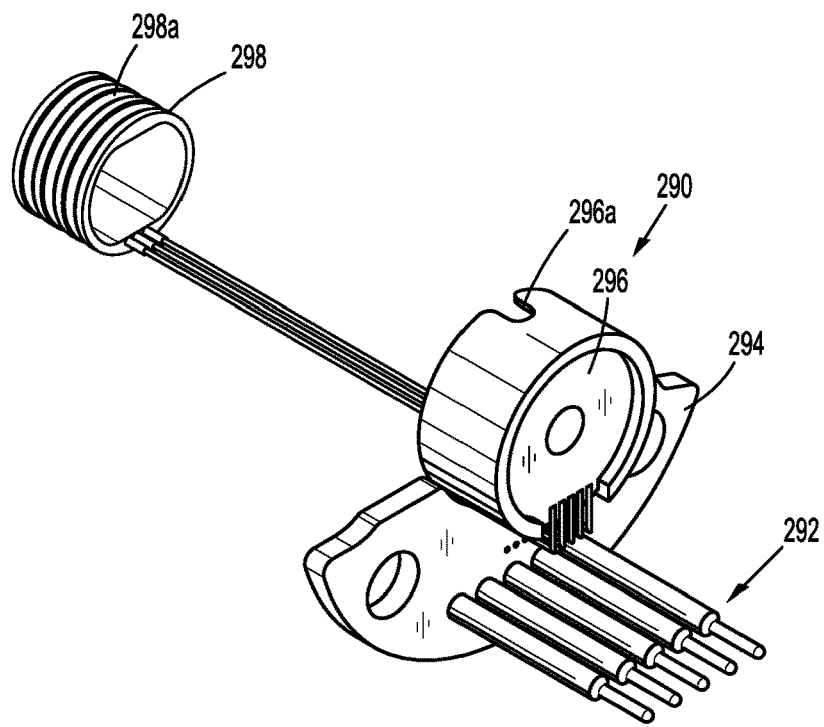
FIG. 12 is a perspective view of an electrical assembly of the adapter assembly of FIGS. 2A and 2B.
Figure 13:
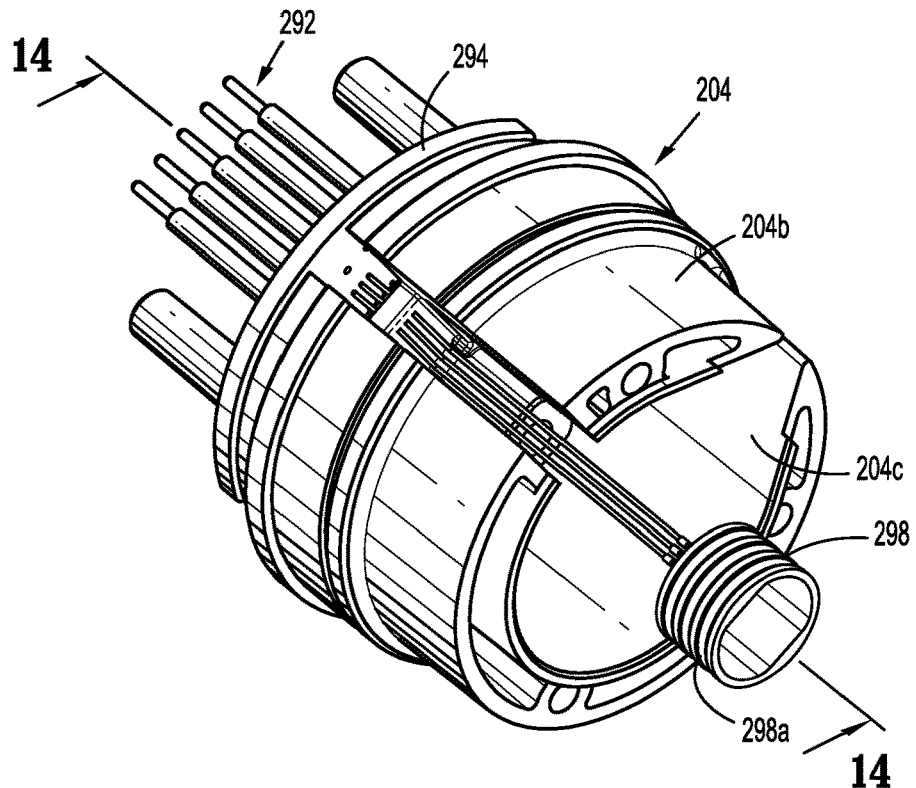
FIG. 13 is a perspective view of the electrical assembly of FIG. 12 shown connected to the core housing of the adapter assembly of FIGS. 2A and 2B.
Figure 14:
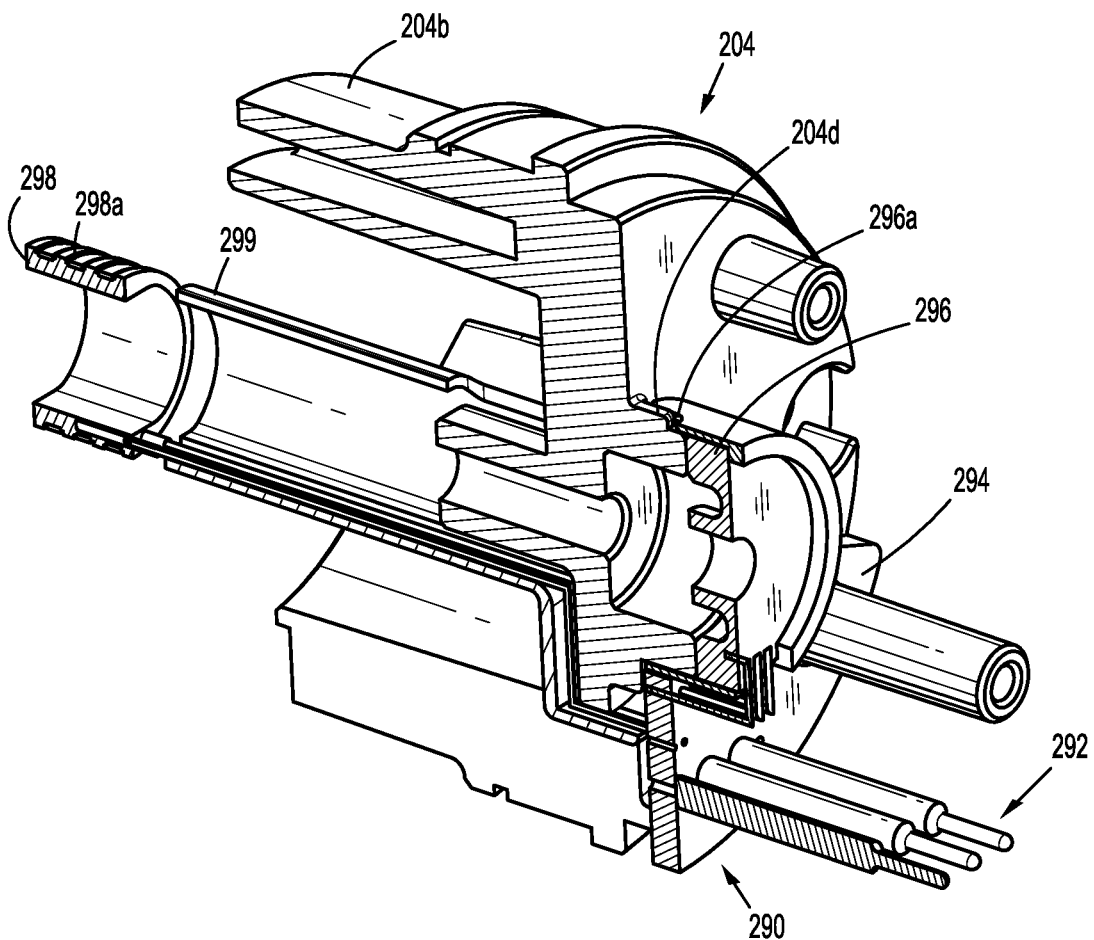
FIG. 14 is a cross-sectional view as taken along section line 14-14 of FIG. 13.
Figure 15:
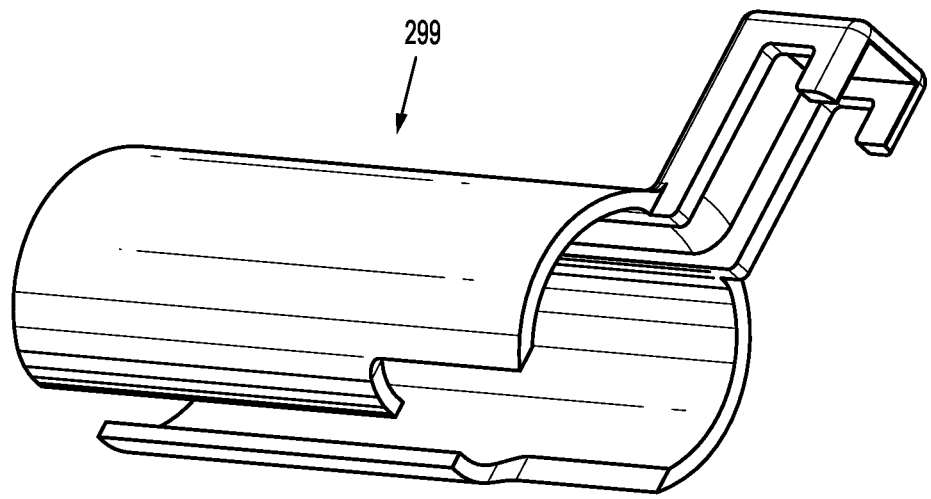
FIG. 15 is a perspective view of a slip ring cannula or sleeve of the adapter assembly of FIGS. 2A and 2B.
Figure 16:
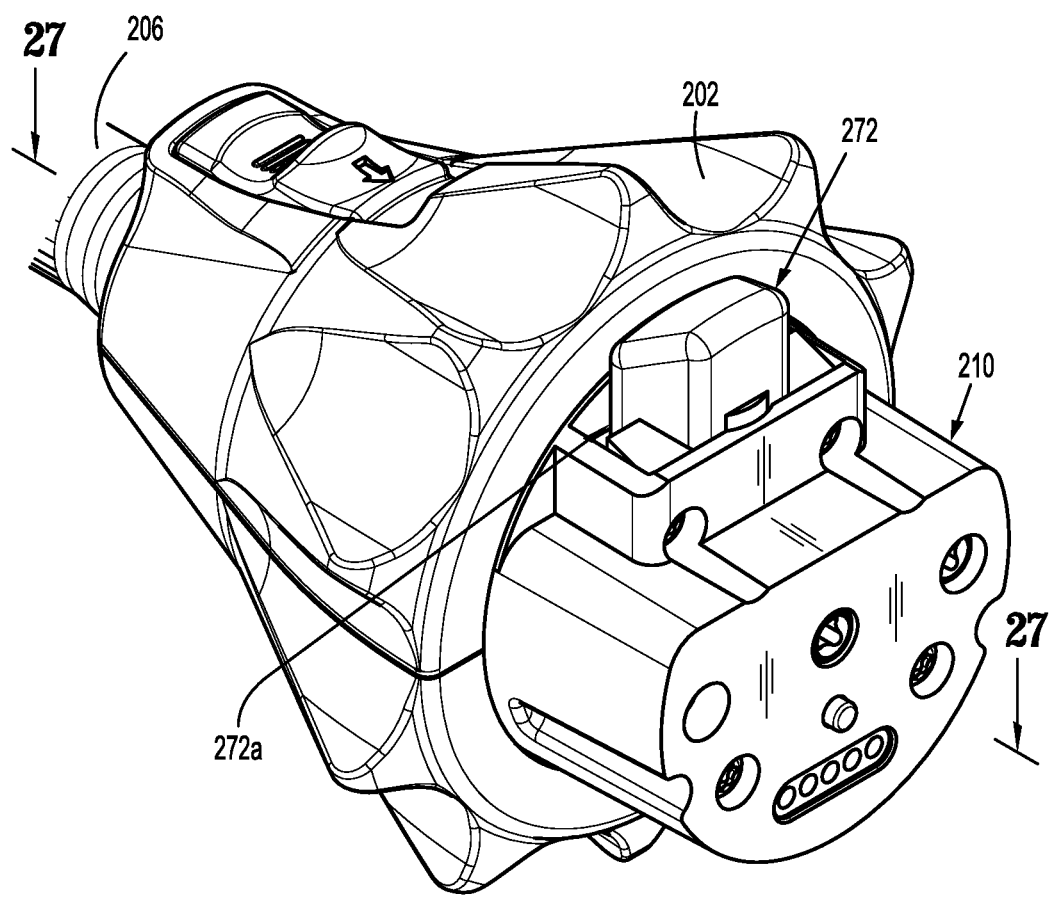
FIG. 16 is an enlarged view of the indicated area of detail of FIG. 2B, illustrating an inner housing assembly of the adapter assembly of FIGS. 2A and 2B.
Figure 17:
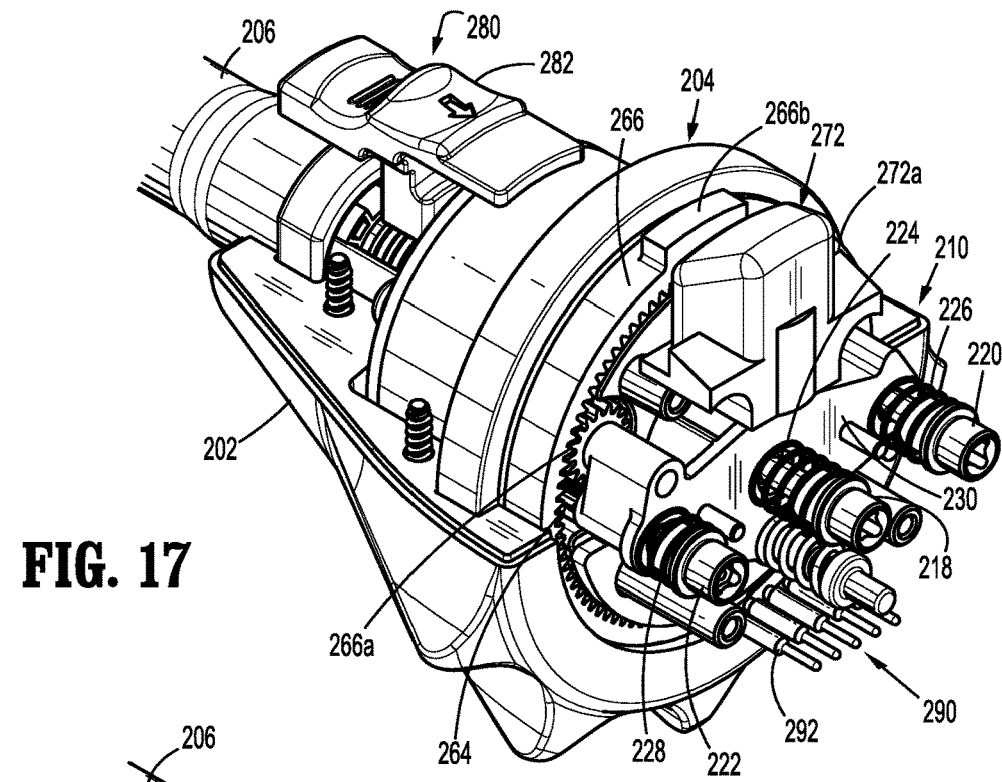
FIG. 17 is a rear, perspective view of the inner housing assembly of FIG. 16 with an outer knob housing half-section and a proximal cap removed therefrom.
Figure 18:
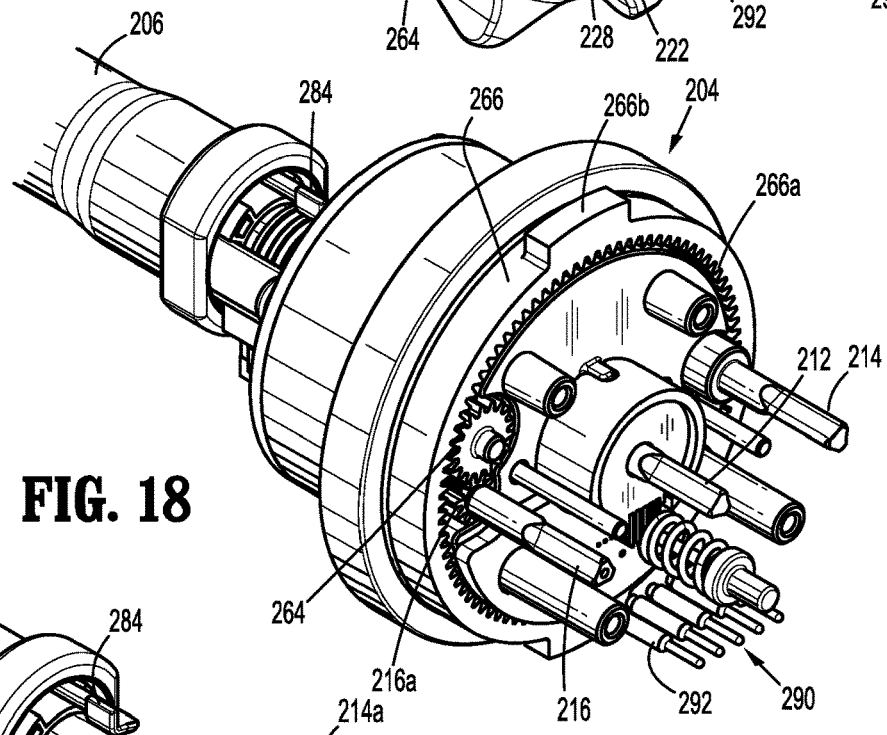
FIG. 18 is a rear, perspective view of the inner housing assembly of FIG. 16 with the outer knob housing, the proximal cap and a bushing plate removed therefrom.
Figure 19:
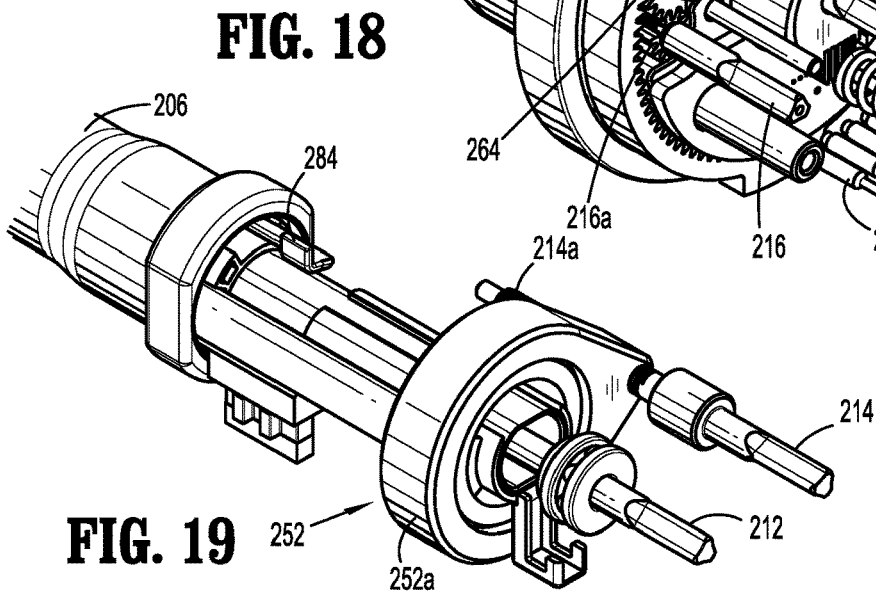
FIG. 19 is a rear, perspective view of the inner housing assembly of FIG. 16 with the outer knob housing, the proximal cap, the bushing plate and an inner housing removed therefrom.
Figure 20:
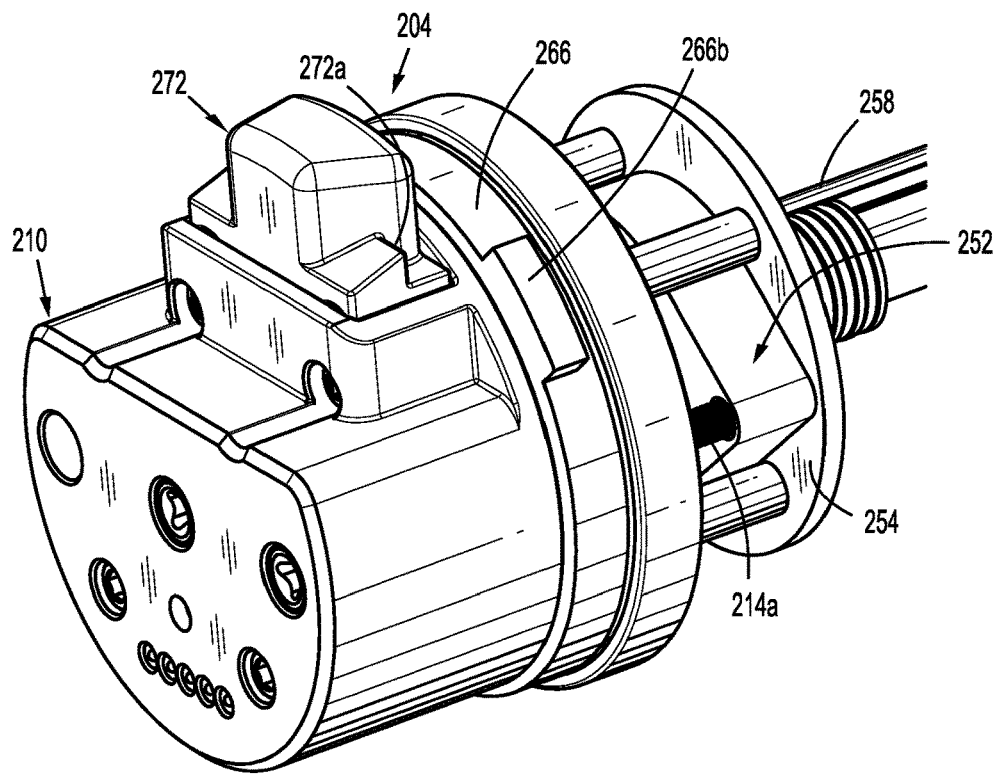
FIG. 20 is a rear, perspective view of the an alternative embodiment of inner housing assembly similar to that shown in FIG. 16 with the outer knob housing and the proximal inner housing removed therefrom.
Figure 21:
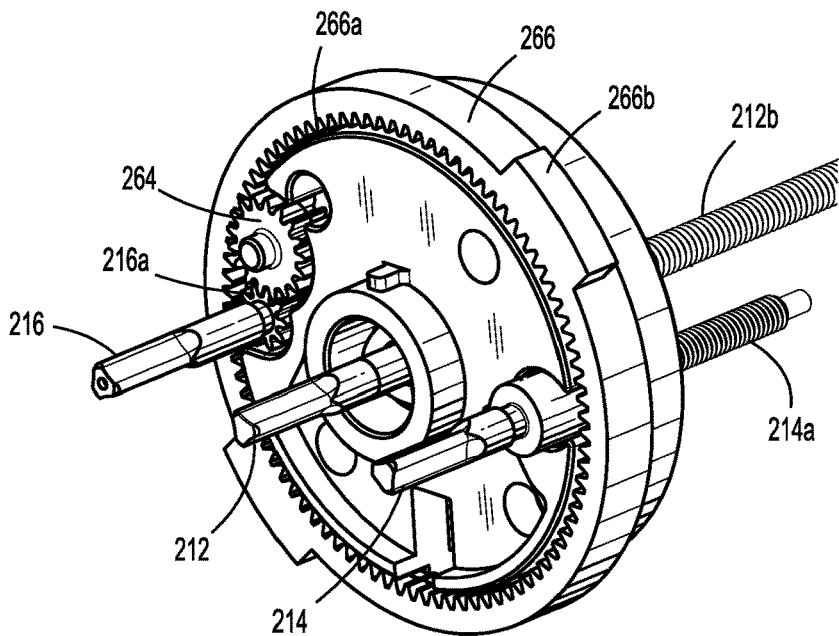
FIG. 21 is a rear, perspective view of the inner housing assembly of FIG. 20 with the outer knob housing, the proximal inner housing and the articulation assembly removed therefrom.
Figure 22:
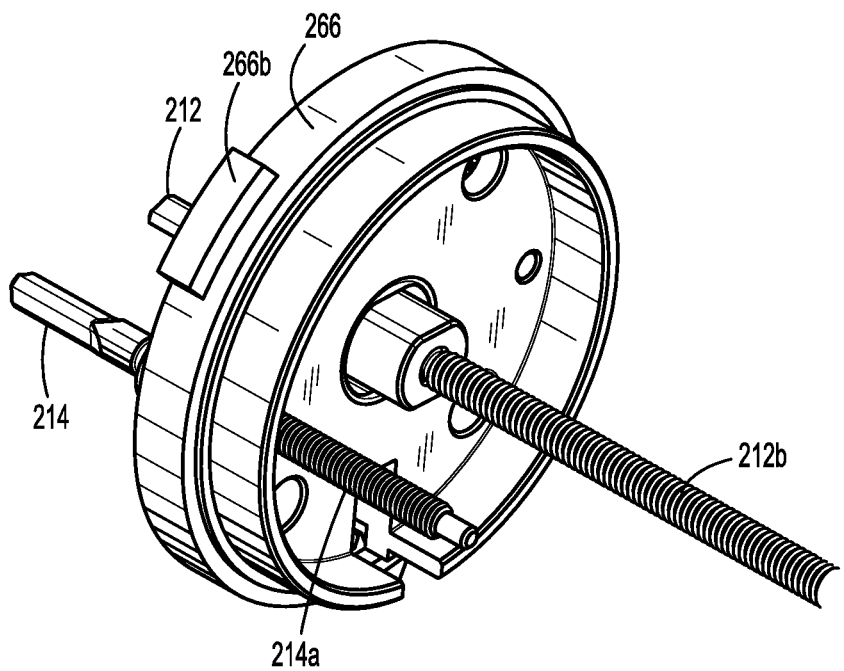
FIG. 22 is a front, perspective view of the inner housing assembly of FIG. 20 with the outer knob housing, the proximal inner housing and the articulation assembly removed therefrom.
Figure 23:
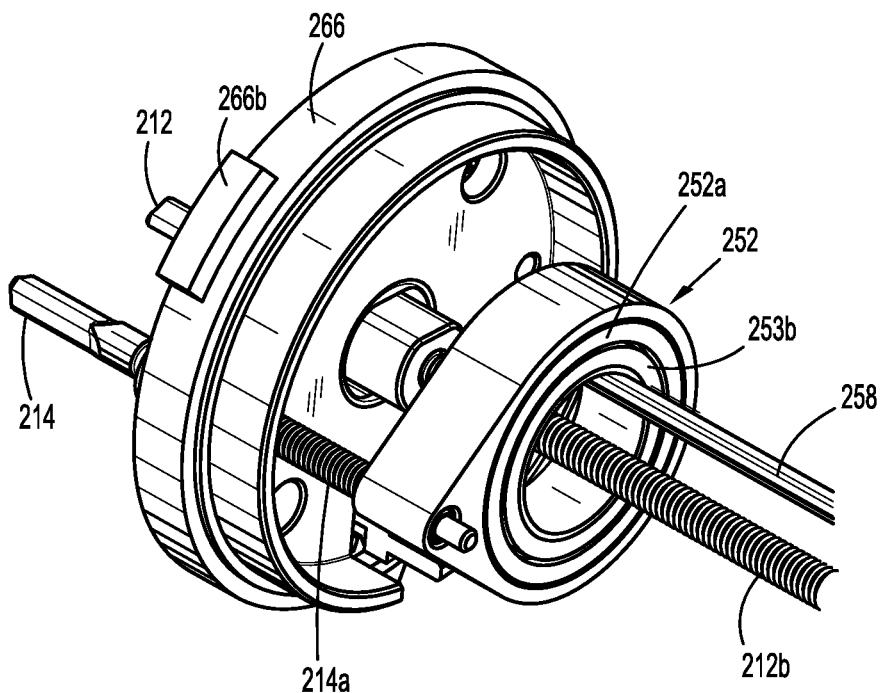
FIG. 23 is a front, perspective view of the inner housing assembly of FIG. 20 with the outer knob housing and the proximal inner housing removed therefrom.
Figure 24:
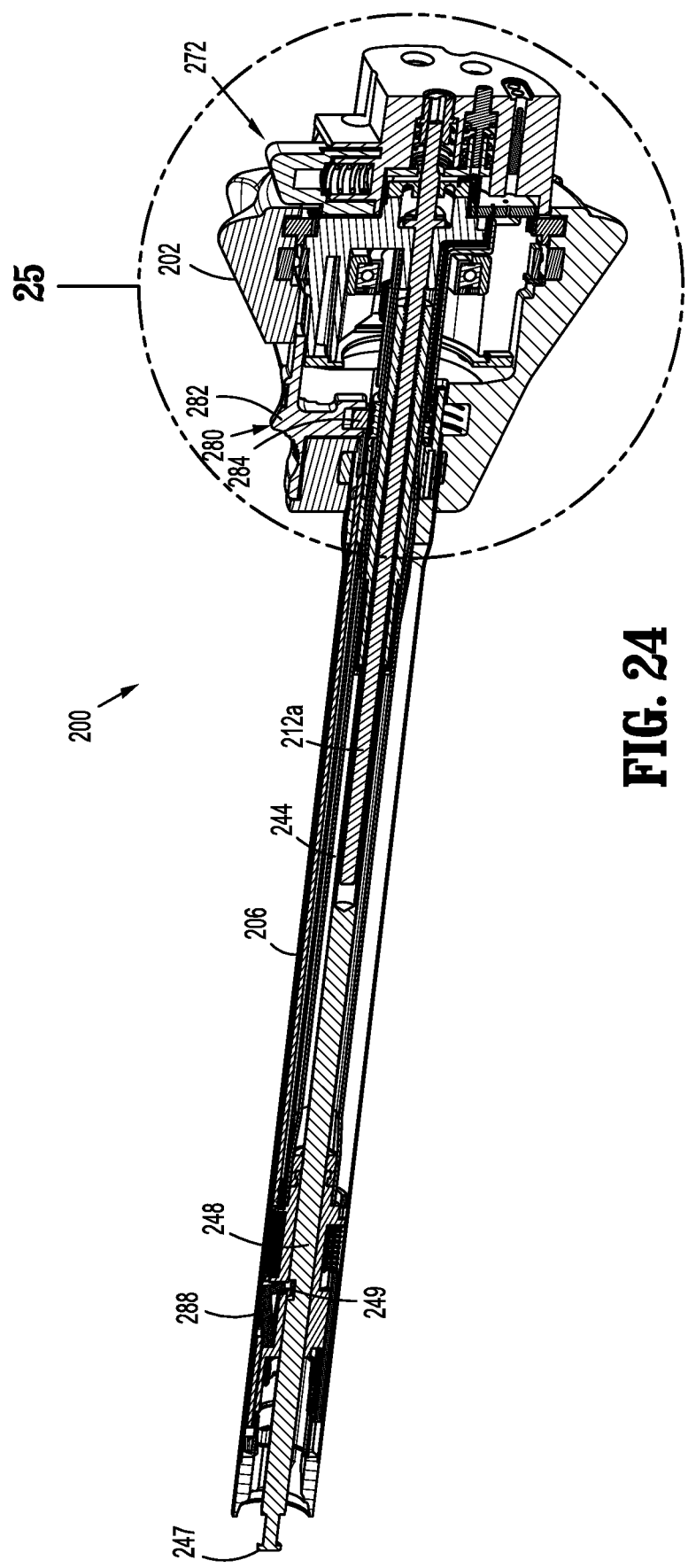
FIG. 24 is a cross-sectional view as taken along section line 24-24 of FIG. 2B.
Figure 25:
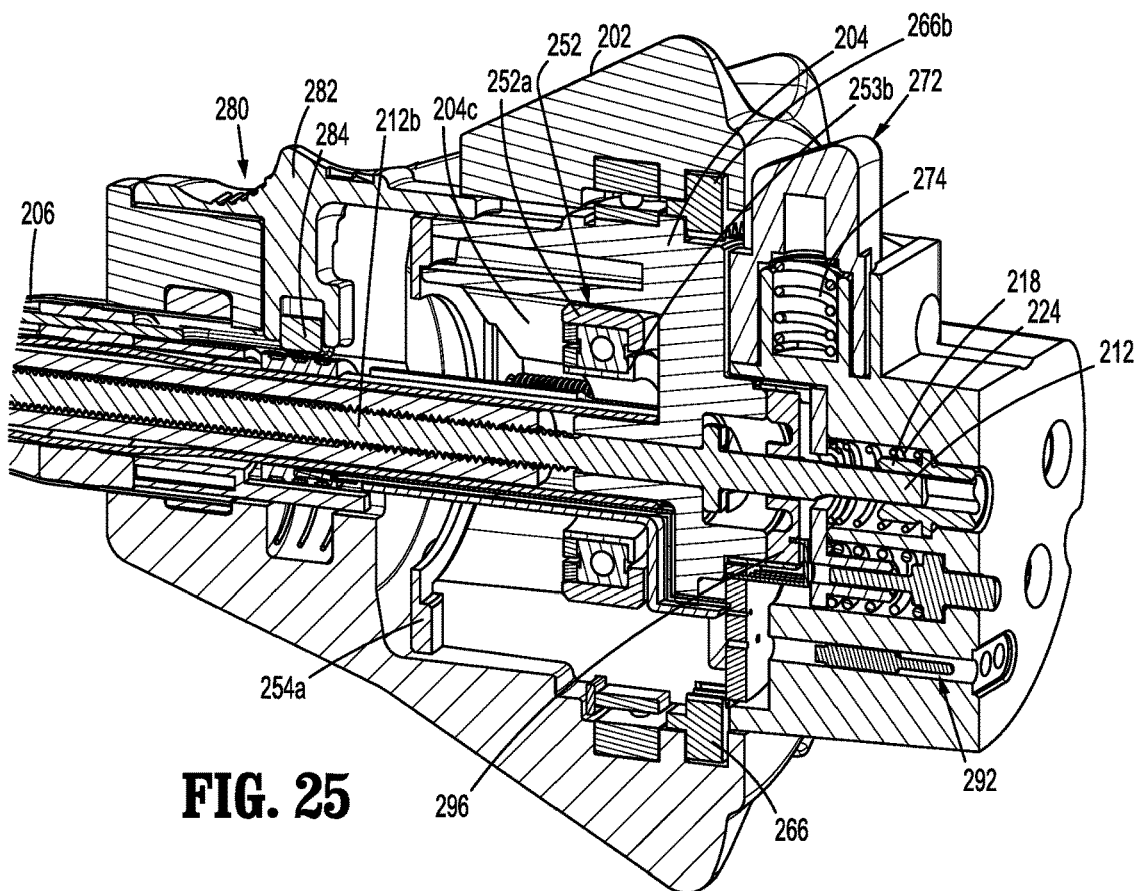
FIG. 25 is an enlarged view of the indicated area of detail of FIG. 24.
Figure 26:
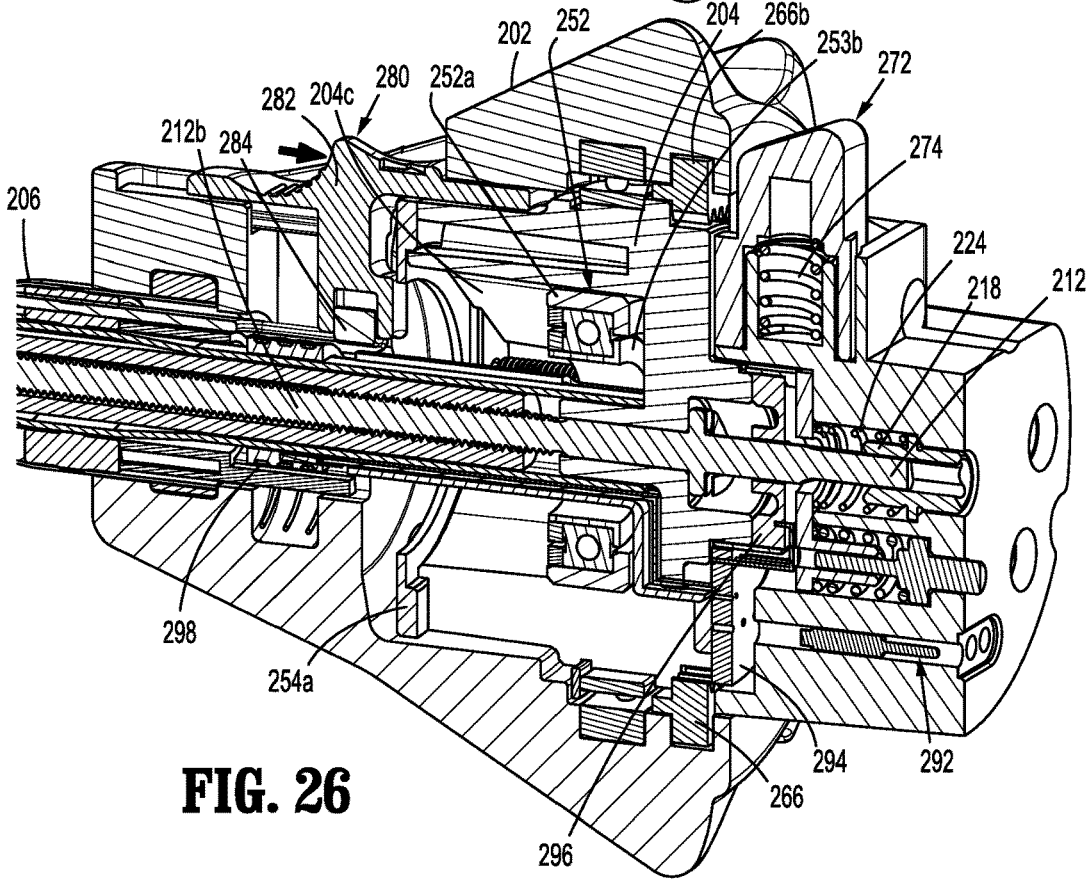
FIG. 26 is an enlarged view of the indicated area of detail of FIG. 24, illustrating a lock button being actuated in a proximal direction.
Figure 27:
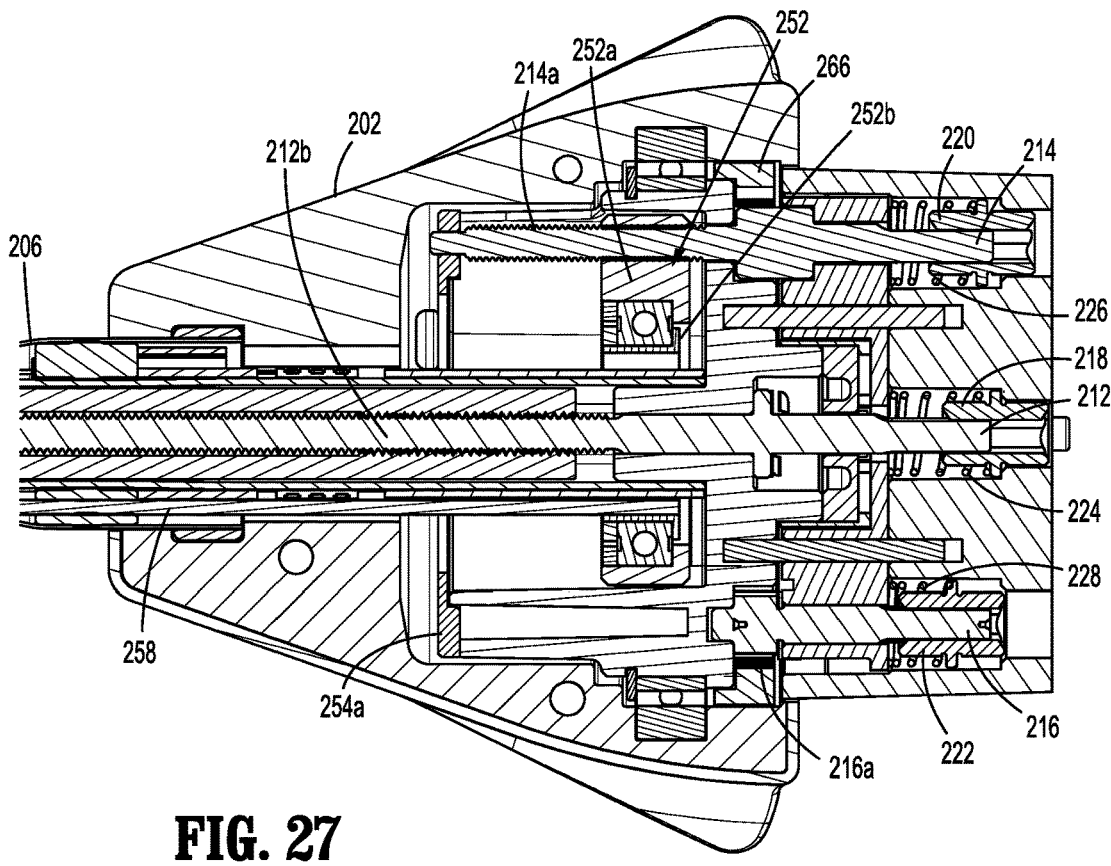
FIG. 27 is a cross-sectional view as taken along section line 27-27 of FIG. 2B.
Figure 28:
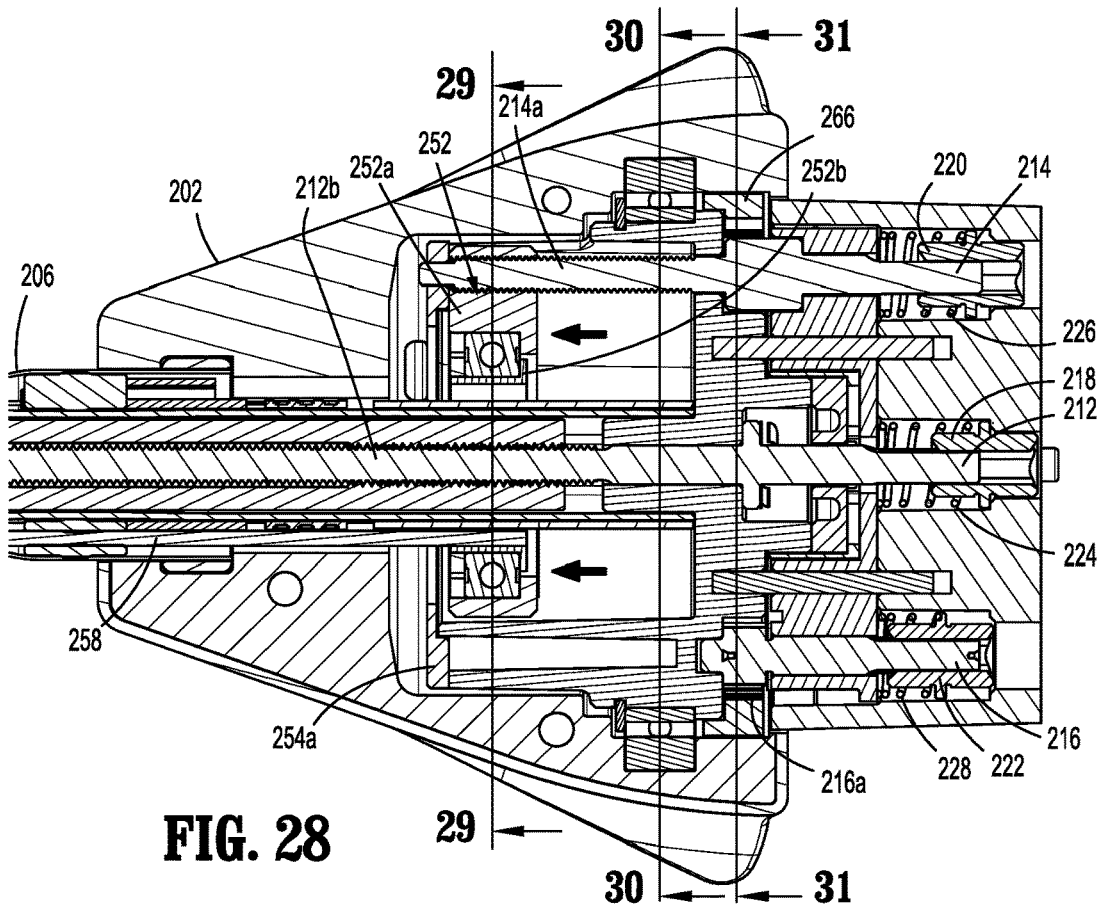
FIG. 28 is a cross-sectional view as taken along section line 27-27 of FIG. 2B, illustrating actuation of the articulation assembly in a distal direction.
Figure 31:
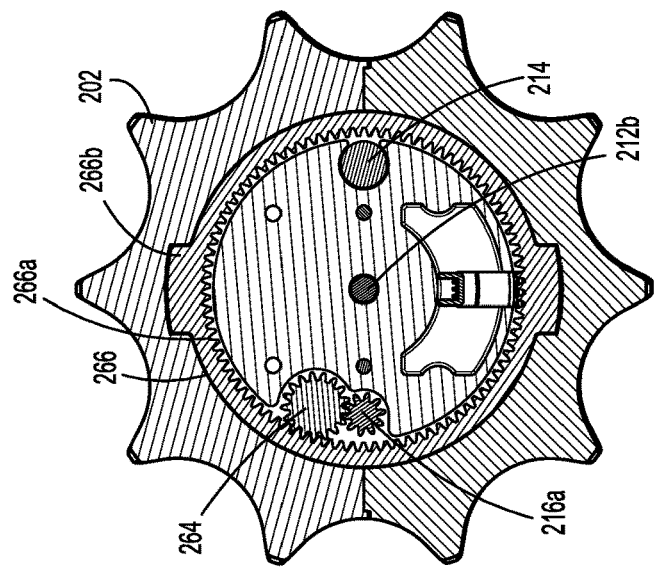
FIG. 31 is a cross-sectional view as taken along section line 31-31 of FIG. 28.
Figure 30:
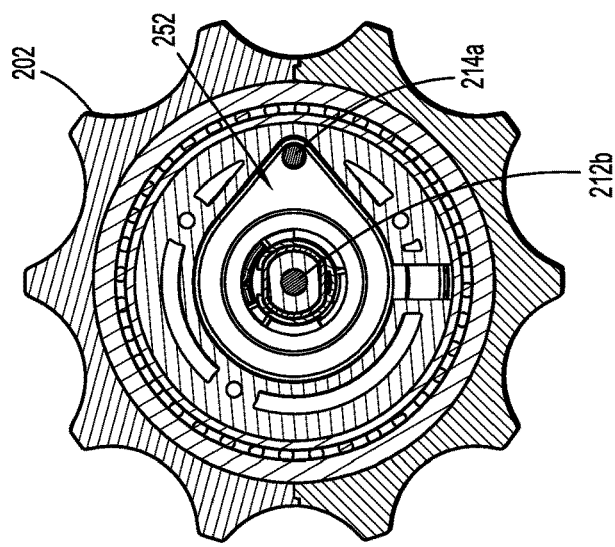
FIG. 30 is a cross-sectional view as taken along section line 30-30 of FIG. 28.
Figure 29:
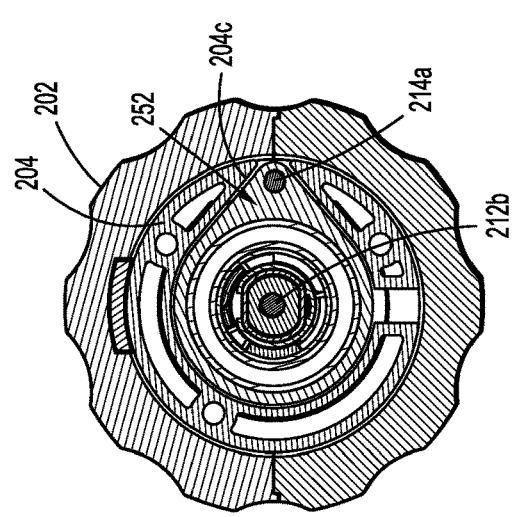
FIG. 29 is a cross-sectional view as taken along section line 29-29 of FIG. 28.
Figure 32:
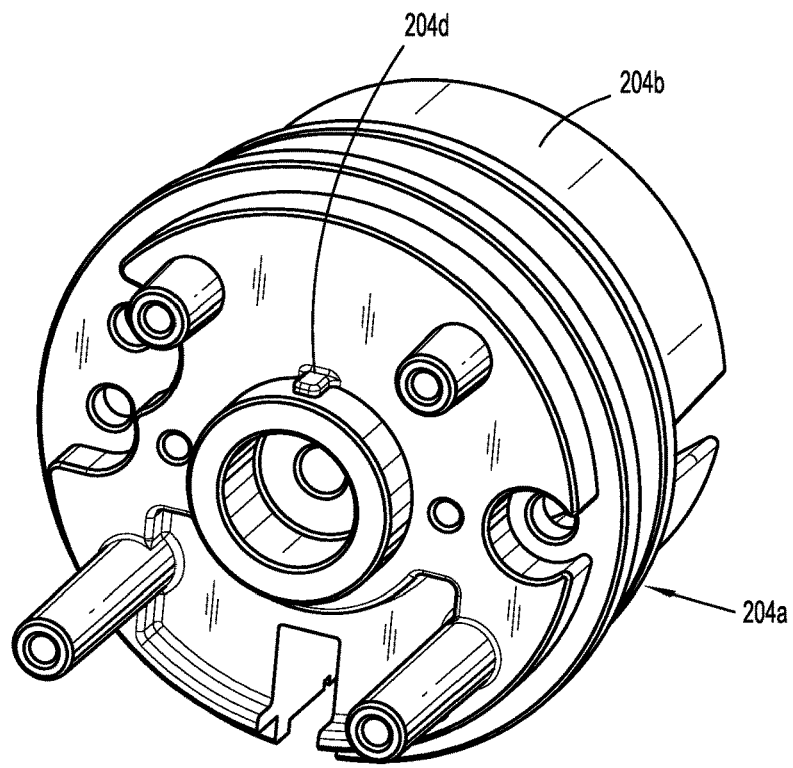
FIG. 32 is a rear, perspective view of a proximal inner housing hub according to the present disclosure.
Figure 33:
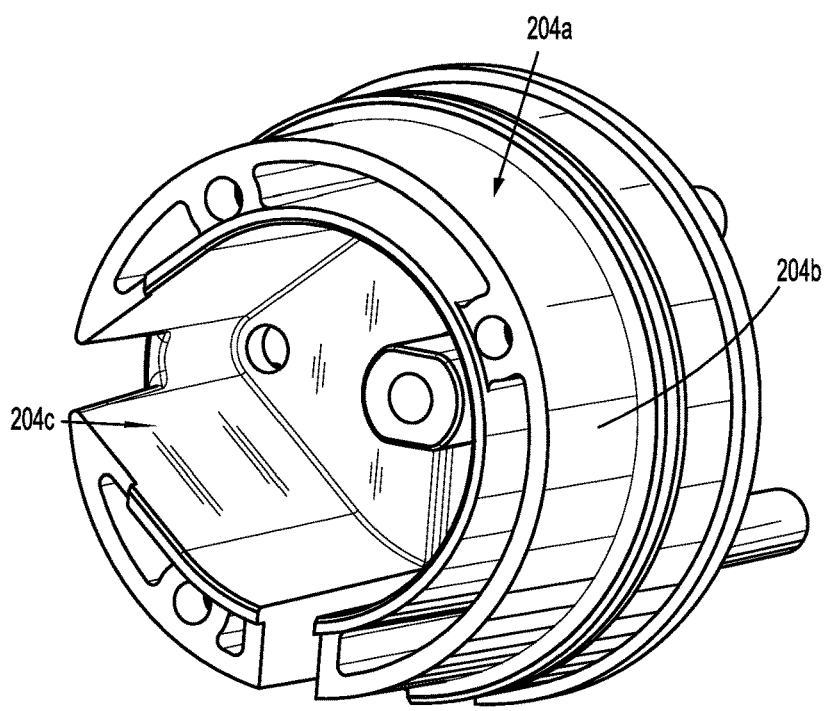
FIG. 33 is a front, perspective view of the proximal inner housing hub of FIG. 32.
Figure 34:
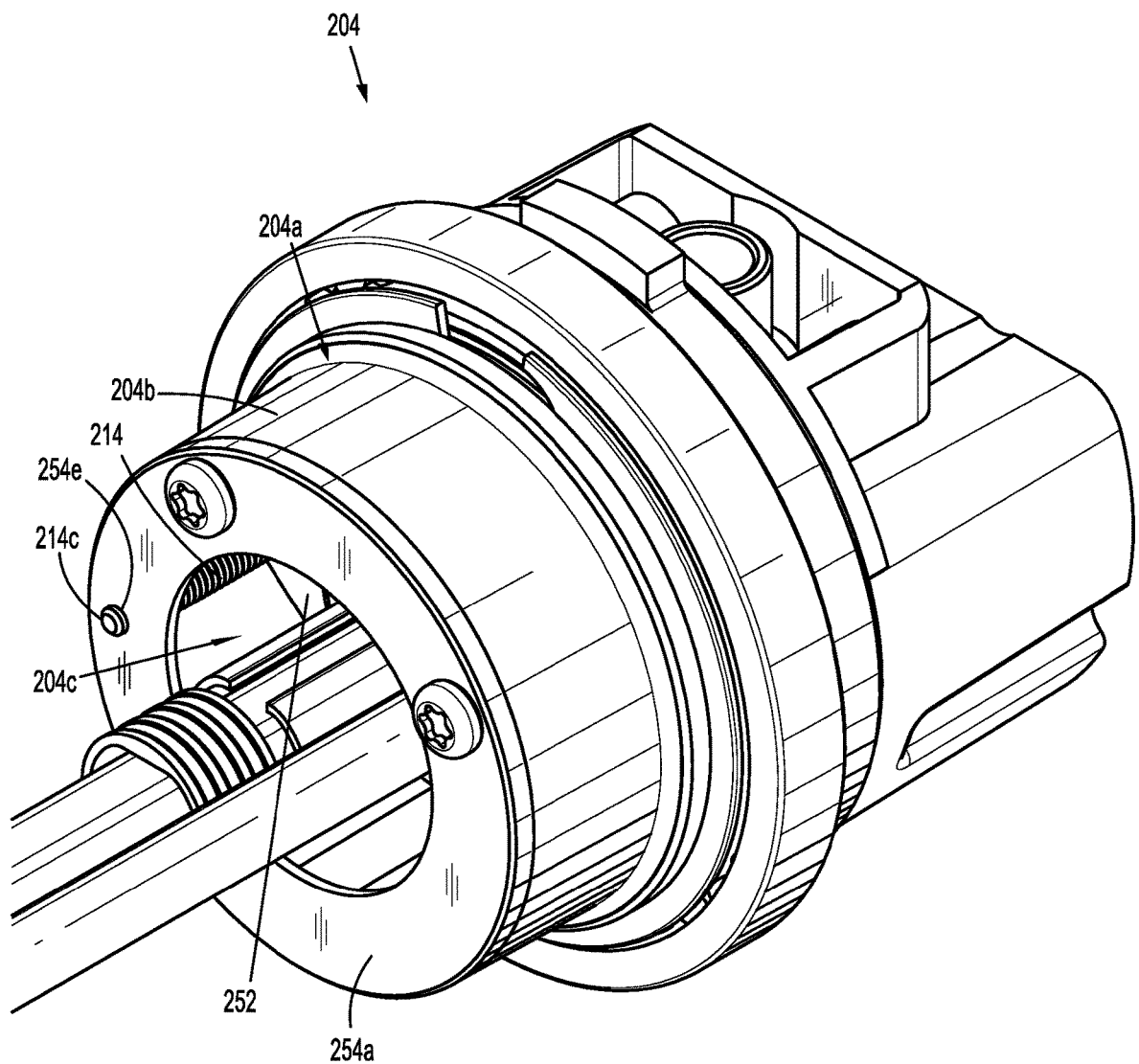
FIG. 34 is a front, perspective view of the proximal inner housing hub of FIGS. 32 and 33 illustrating a first and a second force/rotation transmitting/converting assembly and a reinforcing assembly associated therewith.
Figure 35:
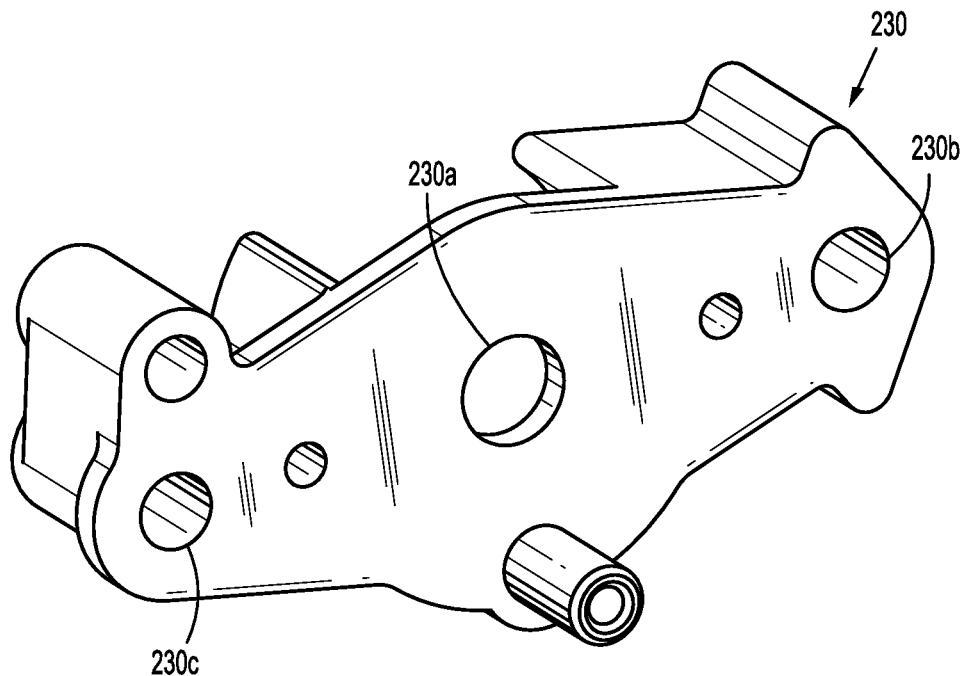
FIG. 35 is a front, perspective view of a plate bushing of the proximal inner housing assembly of the present disclosure.
Figure 36:
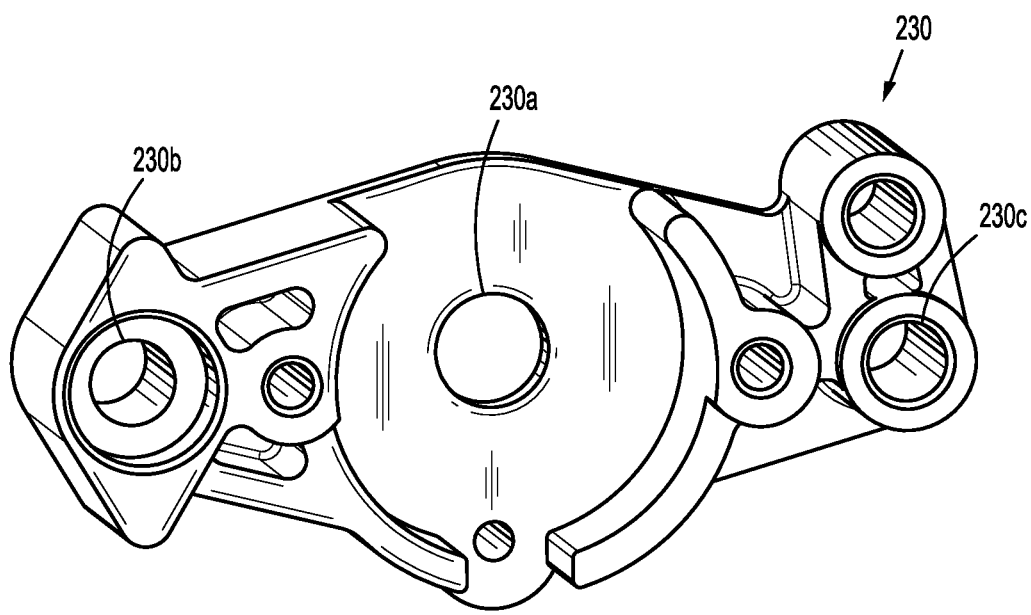
FIG. 36 is a rear, perspective view of the plate bushing of FIG. 35.
Figure 37:
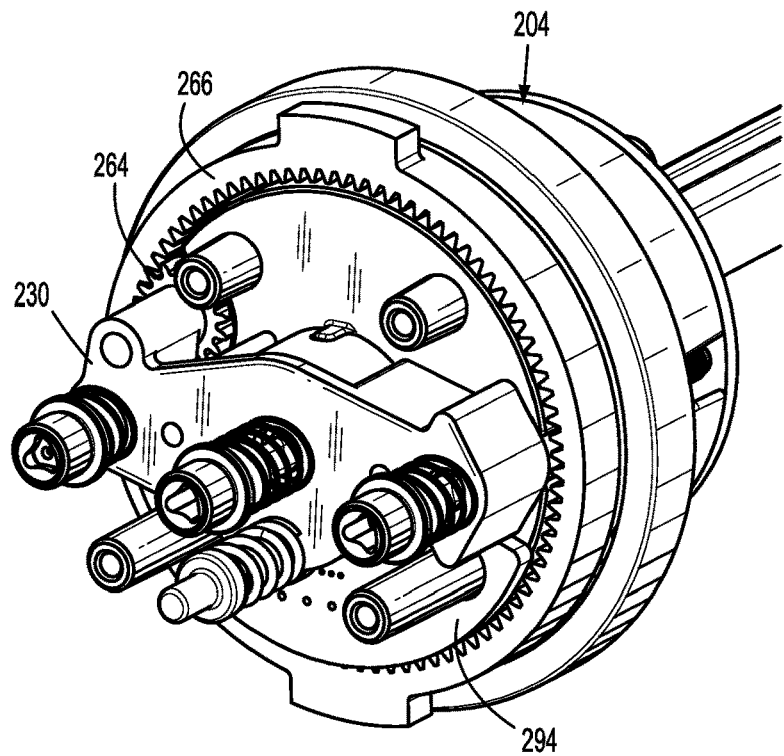
FIG. 37 is a rear, perspective view of the proximal inner housing assembly illustrating the plate bushing of FIGS. 35 and 36 attached thereto.

Specifically, as illustrated in FIG. 6, adapter assembly 200 includes a first, a second and a third force/rotation transmitting/converting assembly 240, 250, 260, respectively, disposed within inner housing 208 and outer tube 206. Each force/rotation transmitting/converting assembly 240, 250, 260 is configured and adapted to transmit or convert a rotation of a first, second and third drive connector 118, 120, 122 of surgical device 100 into axial translation of articulation bar 258 of adapter assembly 200, to effectuate articulation of loading unit 300; a rotation of a ring gear 266 of adapter assembly 200, to effectuate rotation of adapter assembly 200; or axial translation of a distal drive member 248 of adapter assembly 200 to effectuate closing, opening and firing of loading unit 300.

As shown in FIGS. 5, 6 and 24-31, first force/rotation transmitting/converting assembly 240 includes first rotatable proximal drive shaft 212, which, as described above, is rotatably supported within inner housing assembly 204. First rotatable proximal drive shaft 212 includes a non-circular proximal end portion configured for connection with first connector 218 which is connected to respective first connector 118 of surgical device 100. First rotatable proximal drive shaft 212 includes a distal end portion 212b having a threaded outer profile or surface.

First force/rotation transmitting/converting assembly 240 further includes a drive coupling nut 244 rotatably coupled to threaded distal end portion 212b of first rotatable proximal drive shaft 212, and which is slidably disposed within outer tube 206. Drive coupling nut 244 is slidably keyed within proximal core tube portion of outer tube 206 so as to be prevented from rotation as first rotatable proximal drive shaft 212 is rotated. In this manner, as first rotatable proximal drive shaft 212 is rotated, drive coupling nut 244 is translated along threaded distal end portion 212b of first rotatable proximal drive shaft 212 and, in turn, through and/or along outer tube 206.

First force/rotation transmitting/converting assembly 240 further includes a distal drive member 248 that is mechanically engaged with drive coupling nut 244, such that axial movement of drive coupling nut 244 results in a corresponding amount of axial movement of distal drive member 248. The distal end portion of distal drive member 248 supports a connection member 247 configured and dimensioned for selective engagement with a drive member 374 of drive assembly 360 of loading unit 300 (FIG. 48). Drive coupling nut 244 and/or distal drive member 248 function as a force transmitting member to components of loading unit 300, as described in greater detail below.

In operation, as first rotatable proximal drive shaft 212 is rotated, due to a rotation of first connector sleeve 218, as a result of the rotation of the first respective drive connector 118 of surgical device 100, drive coupling nut 244 is caused to be translated axially along first distal drive shaft 242. As drive coupling nut 244 is caused to be translated axially along first distal drive shaft 242, distal drive member 248 is caused to be translated axially relative to outer tube 206. As distal drive member 248 is translated axially, with connection member 247 connected thereto and engaged with drive member 374 of drive assembly 360 of loading unit 300 (FIG. 47), distal drive member 248 causes concomitant axial translation of drive member 374 of loading unit 300 to effectuate a closure of tool assembly 304 and a firing of tool assembly 304 of loading unit 300.

With reference to FIGS. 5-11, 19 and 23-31, second drive converter assembly 250 of adapter assembly 200 includes second proximal drive shaft 214 rotatably supported within inner housing assembly 204. Second rotatable proximal drive shaft 214 includes a non-circular proximal end portion configured for connection with second connector or coupler 220 which is connected to respective second connector 120 of surgical device 100. Second rotatable proximal drive shaft 214 further includes a distal end portion 214b having a threaded outer profile or surface.

Distal end portion 214b of proximal drive shaft 214 is threadably engaged with an articulation bearing housing 252a of an articulation bearing assembly 252. Articulation bearing assembly 252 includes a housing 252a supporting an articulation bearing 253 having an inner race 253b that is independently rotatable relative to an outer race 253a. Articulation bearing housing 252a has a non-circular outer profile, for example tear-drop shaped, that is slidably and non-rotatably disposed within a complementary bore 204c (FIGS. 25, 26, 29 and 33) of inner housing hub 204a.

Second drive converter assembly 250 of adapter assembly 200 further includes an articulation bar 258 having a proximal portion 258a secured to inner race 253b of articulation bearing 253. A distal portion 258b of articulation bar 258 includes a slot 258c therein, which is configured to accept a portion 366, e.g., a flag, articulation link (FIG. 47) of loading unit 300. Articulation bar 258 functions as a force transmitting member to components of loading unit 300, as described in greater detail below.

With further regard to articulation bearing assembly 252, articulation bearing assembly 252 is both rotatable and longitudinally translatable. Additionally, it is envisioned that articulation bearing assembly 252 allows for free, unimpeded rotational movement of loading unit 300 when its jaw members 306, 308 are in an approximated position and/or when jaw members 306, 308 are articulated.

In operation, as second proximal drive shaft 214 is rotated due to a rotation of second connector sleeve 220, as a result of the rotation of the second drive connector 120 of surgical device 100, articulation bearing assembly 252 is caused to be translated axially along threaded distal end portion 214b of second proximal drive shaft 214, which in turn causes articulation bar 258 to be axially translated relative to outer tube 206. As articulation bar 258 is translated axially, articulation bar 258, being coupled to articulation link 366 of loading unit 300, causes concomitant axial translation of articulation link 366 of loading unit 300 to effectuate an articulation of tool assembly 304. Articulation bar 258 is secured to inner race 253b of articulation bearing 253 and is thus free to rotate about the longitudinal axis X-X relative to outer race 253a of articulation bearing 253.

As illustrated in FIGS. 6, 17, 18, 20-23, 25-28, 31 and 37-40 and as mentioned above, adapter assembly 200 includes a third force/rotation transmitting/converting assembly 260 supported in inner housing assembly 204. Third force/rotation transmitting/converting assembly 260 includes a rotation ring gear 266 fixedly supported in and connected to outer knob housing 202. Ring gear 266 defines an internal array of gear teeth 266a (FIG. 6). Ring gear 266 includes a pair of diametrically opposed, radially extending protrusions 266b (FIG. 6) projecting from an outer edge thereof. Protrusions 266b are disposed within recesses defined in outer knob housing 202, such that rotation of ring gear 266 results in rotation of outer knob housing 202, and vice a versa.

Third force/rotation transmitting/converting assembly 260 further includes third rotatable proximal drive shaft 216 which, as described above, is rotatably supported within inner housing assembly 204. Third rotatable proximal drive shaft 216 includes a non-circular proximal end portion configured for connection with third connector 222 which is connected to respective third connector 122 of surgical device 100. Third rotatable proximal drive shaft 216 includes a spur gear 216a keyed to a distal end thereof. A reversing spur gear 264 inter-engages spur gear 216a of third rotatable proximal drive shaft 216 to gear teeth 266a of ring gear 266.

In operation, as third rotatable proximal drive shaft 216 is rotated, due to a rotation of third connector sleeve 222, as a result of the rotation of the third drive connector 122 of surgical device 100, spur gear 216a of third rotatable proximal drive shaft 216 engages reversing gear 264 causing reversing gear 264 to rotate. As reversing gear 264 rotates, ring gear 266 also rotates thereby causing outer knob housing 202 to rotate. As outer knob housing 202 is rotated, outer tube 206 is caused to be rotated about longitudinal axis "X" of adapter assembly 200. As outer tube 206 is rotated, loading unit 300, that is connected to a distal end portion of adapter assembly 200, is also caused to be rotated about a longitudinal axis of adapter assembly 200.

Adapter assembly 200 further includes, as seen in FIGS. 1B, 3-5, 16, 17, 20 and 24-26, an attachment/detachment button 272 supported thereon. Specifically, button 272 is supported on drive coupling assembly 210 of adapter assembly 200 and is biased by a biasing member 274 to an un-actuated condition. Button 272 includes lip or ledge 272a formed therewith that is configured to snap behind a corresponding lip or ledge 108b defined along recess 108a of connecting portion 108 of surgical device 100. In use, when adapter assembly 200 is connected to surgical device 100, lip 272a of button 272 is disposed behind lip 108b of connecting portion 108 of surgical device 100 to secure and retain adapter assembly 200 and surgical device 100 with one another. In order to permit disconnection of adapter assembly 200 and surgical device 100 from one another, button 272 is depresses or actuated, against the bias of biasing member 274, to disengage lip 272*a* of button 272 and lip 108*b* of connecting portion 108 of surgical device 100.

With reference to FIGS. 1A, 2A, 2B, 3-5 and 24-26, adapter assembly 200 further includes a lock mechanism 280 for fixing the axial position and radial orientation of distal drive member 248. Lock mechanism 280 includes a button 282 slidably supported on outer knob housing 202. Lock button 282 is connected to an actuation bar 284 that extends longitudinally through outer tube 206. Actuation bar 284 moves upon a movement of lock button 282. Upon a predetermined amount of movement of lock button 282, a distal end of actuation bar 284 may move into contact with a lock out (not shown), which causes the lock out to cam a camming member 288 (FIG. 24) from a recess 249 in distal drive member 248. When camming member 288 is in engagement with recess 249 (e.g., at least partially within recess 249, see FIGS. 6 and 24), the engagement between camming member 288 and distal drive member 248 effectively locks the axial and rotational position of end effector 300 that is engaged with connection member 247.

In operation, in order to lock the position and/or orientation of distal drive member 248, a user moves lock button 282 from a distal position to a proximal position (FIGS. 25 and 26), thereby causing the lock out (not shown) to move proximally such that a distal face of the lock out moves out of contact with camming member 288, which causes camming member 288 to cam into recess 249 of distal drive member 248. In this manner, distal drive member 248 is prevented from distal and/or proximal movement. When lock button 282 is moved from the proximal position to the distal position, the distal end of actuation bar 284 moves distally into the lock out, against the bias of a biasing member (not shown), to force camming member 288 out of recess 249, thereby allowing unimpeded axial translation and radial movement of distal drive member 248.

Reference may be made to U.S. Pat. No. 9,597,104, the entire content of which is incorporated herein by reference, for a more detailed discussion of the construction and operation of lock mechanism 280.

With reference to FIGS. 1B, 6, 12-15 and 25-28, adapter assembly 200 includes an electrical assembly 290 supported on and in outer knob housing 202 and inner housing assembly 204. Electrical assembly 290 includes a plurality of electrical contact pins 292, supported on a circuit board 294, for electrical connection to a corresponding electrical plug 190 disposed in connecting portion 108 of surgical device 100. Electrical contacts 290 serve to allow for calibration and communication of life-cycle information to the circuit board of surgical device 100 via electrical plugs 190 that are electrically connected to the circuit board (not shown) of surgical device 100.

Electrical assembly 290 further includes a strain gauge 296 electrically connected to circuit board 294. Strain gauge 296 is provided with a notch 296*a* which is configured and adapted to receive stem 204*d* of hub 204*a* of inner housing assembly 204. Stem 204*d* of hub 204*a* functions to restrict rotational movement of strain gauge 296. As illustrated in FIGS. 25-28, first rotatable proximal drive shaft 212 extends through strain gauge 296. Strain gauge 296 provides a closed-loop feedback to a firing/clamping load exhibited by first rotatable proximal drive shaft 212.

Electrical assembly 290 also includes a slip ring 298 disposed core tube of tube 206. Slip ring 298 is in electrical connection with circuit board 294. Slip ring 298 functions to permit rotation of first rotatable proximal drive shaft 212 and axial translation of drive coupling nut 244 while still maintaining electrical contact of electrical contact rings 298*a* thereof with at least another electrical component within adapter assembly 200, and while permitting the other electrical components to rotate about first rotatable proximal drive shaft 212 and drive coupling nut 244

Electrical assembly 290 may include a slip ring cannula or sleeve 299 positioned core tube of tube 206 to protect and/or shield any wires extending from slip ring 298.

Turning now to FIGS. 6, 11, 14, 32 and 33, inner housing assembly 204 has been designed to reduce incidents of racking of second proximal drive shaft 214 as drive shaft 214 rotates to axially translate articulation bearing assembly 252. Inner housing assembly 204 includes a hub 204*a* having a distally oriented annular wall 204*b* defining a substantially circular outer profile, and defining a substantially tear-drop shaped inner recess or bore 204*c*. Bore 204*c* of hub 204*a* is shaped and dimensioned to slidably receive articulation bearing assembly 252 therewithin.

Inner housing assembly 204 includes a ring plate 254*a* (FIG. 34) secured to a distal face of distally oriented annular wall 204*b* of hub 204*a*. Plate 254*a* defines an aperture 254*e* therethrough that is sized and formed therein so as to be aligned with second proximal drive shaft 214 and to rotatably receive a distal tip 214*c* of second proximal drive shaft 214. In this manner, distal tip 214*c* of second proximal drive shaft 214 is supported and prevented from moving radially away from a longitudinal rotational axis of second proximal drive shaft 214 as second proximal drive shaft 214 is rotated to axially translate articulation bearing assembly 252.

As illustrated in FIGS. 14, 32, 39 and 40, hub 204*a* defines a feature (e.g., a stem or the like) 204*d* projecting therefrom which functions to engage notch 296*a* of strain gauge 296 of electrical assembly 290 to measure forces experienced by shaft 212 as surgical device 100 is operated.

With reference to FIGS. 35-40, a plate bushing 230 of inner housing assembly 204 is shown and described. Plate bushing 230 extends across hub 204*a* of inner housing assembly 204 and is secured to hub 204*a* by fastening members. Plate bushing 230 defines three apertures 230*a*, 230*b*, 230*c* that are aligned with and rotatably receive respective first, second and third proximal drive shafts 212, 214, 216 therein. Plate bushing 230 provides a surface against which first, second and third biasing members 224, 226 and 228 come into contact or rest against.

Figure 40:
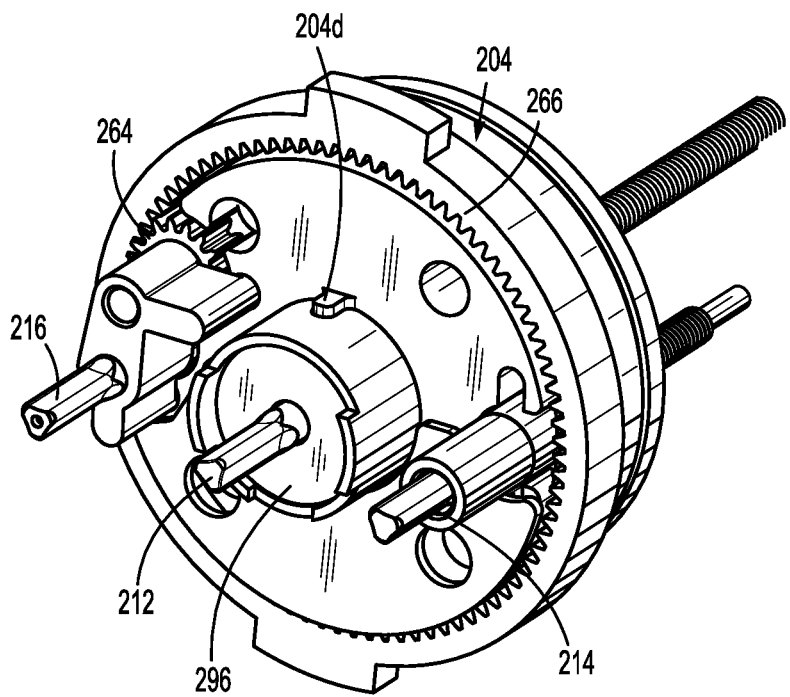
FIG. 40 is a rear, perspective view of the proximal inner housing assembly of FIG. 37 with connector sleeves removed therefrom.
Figure 41:
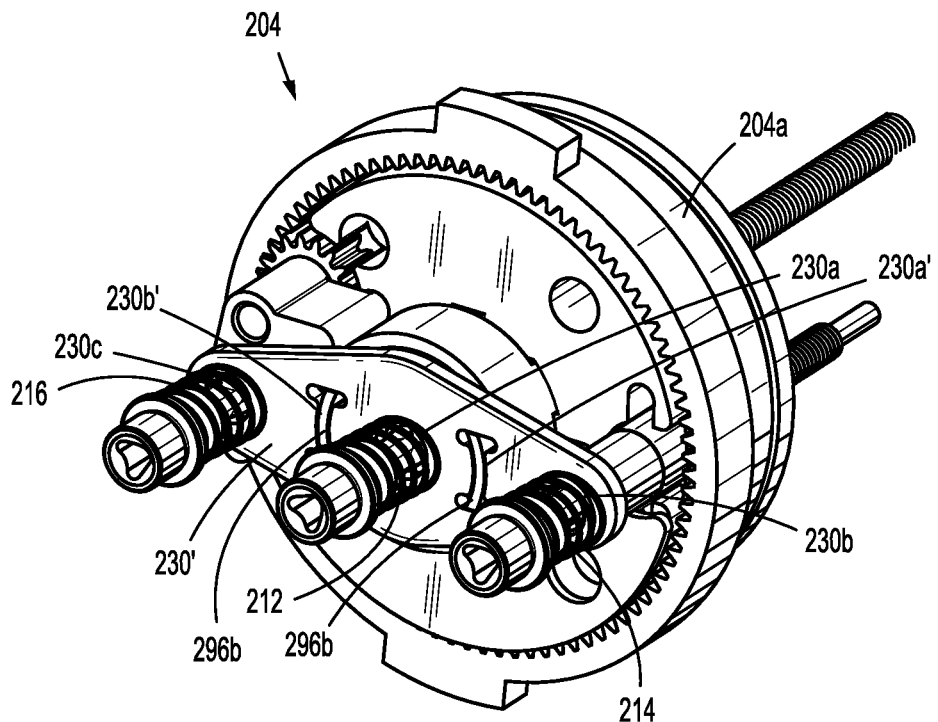
FIG. 41 is a rear, perspective of the inner housing assembly of FIG. 37 illustrating a support plate, according to another embodiment of the present disclosure, coupled thereto.
Figure 42:
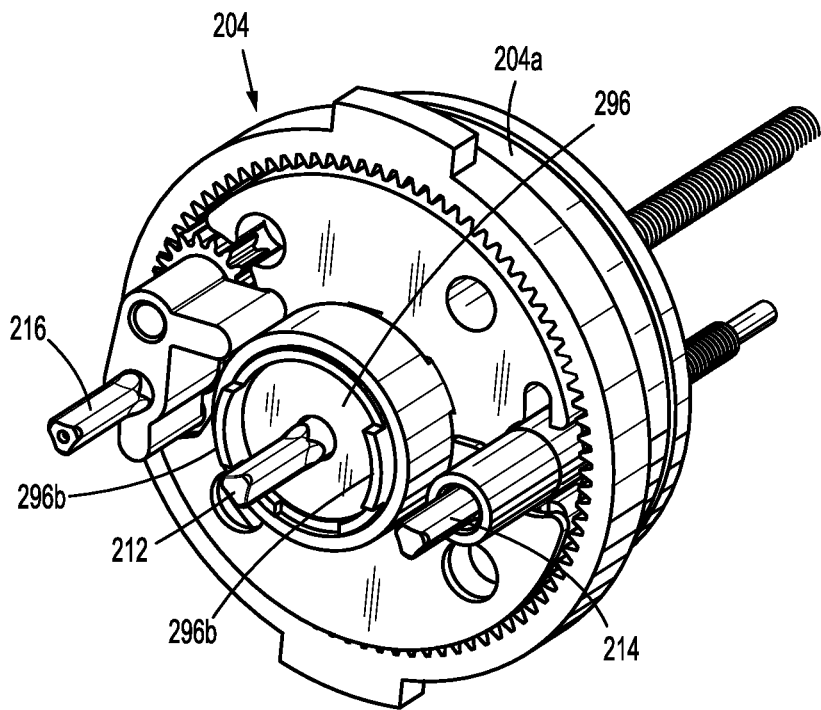
FIG. 42 is a rear, perspective of the inner housing assembly of FIG. 41 with the support plate removed therefrom.
Figure 43:
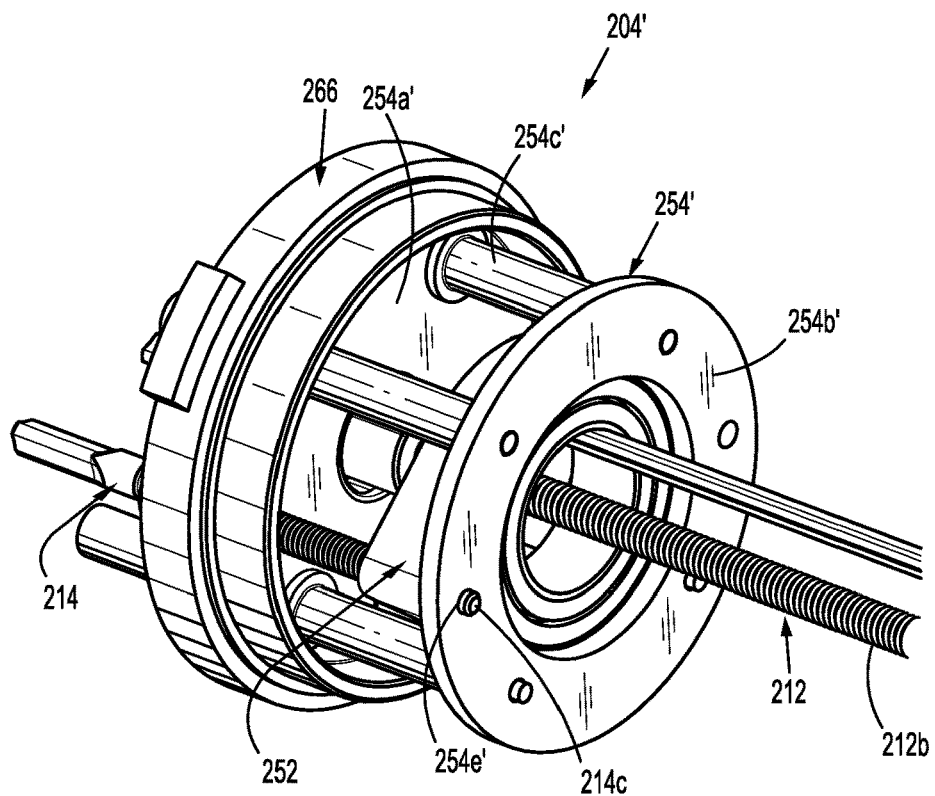
FIG. 43 is a front, perspective view of an inner housing assembly according to another embodiment of the present disclosure with the outer knob housing, the proximal inner housing removed therefrom.
Figure 44:
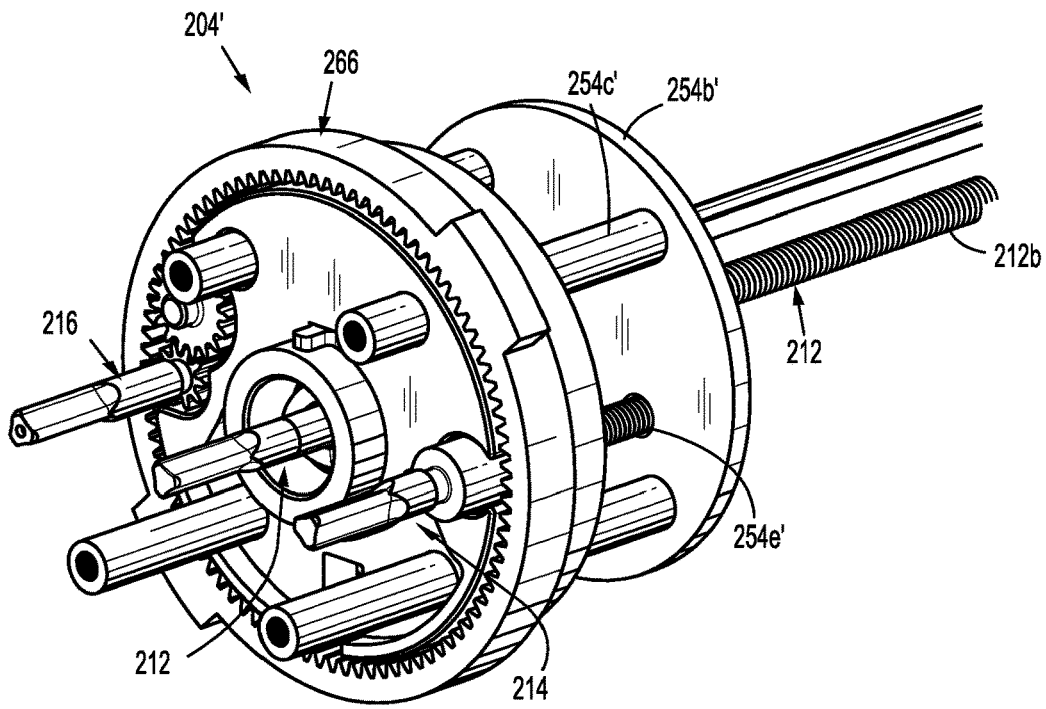
FIG. 44 is a rear, perspective view of the inner housing assembly of FIG. 43 with the outer knob housing, the proximal inner housing and the articulation assembly removed therefrom.

While plate bushing 230 has been shown and described as being a unitary monolithic piece, as illustrated in FIGS. 6 and 37-40, it is envisioned and within the scope of the present application that plate bushing 230 may be separated into several parts including, and not limited to, as seen in FIGS. 40-42, a support plate 230' extending across drive shafts 212, 214, 216, and a separate bushing for each of drive shafts 212, 214, 216 and disposed between the support plate 230' and hub 204*a* of inner housing assembly 204. Support plate 230' may include a pair of slots 230*a*', 230*b*' formed therein, which are configured and adapted to receive tabs 296*b* of strain gauge 296 that project axially therefrom.

Turning now to FIGS. 43-47, an inner housing assembly 204' according to another embodiment of the present disclosure is shown and will be described. In order to reduce incidents of racking (i.e., distal end 214*b* of second proximal drive shaft 214 moving radially away from a longitudinal rotational axis thereof) of second proximal drive shaft 214 as drive shaft 214 rotates to axially translate articulation bearing assembly 252, inner housing assembly 204' may include a reinforcement frame or bracket assembly 254'. Bracket assembly 254' includes a first plate 254*a*' and a second plate 254b' integrally connected to and spaced a distance from first plate 254a' by a plurality of connecting rods 254c' extending therebetween.

First plate 254a' is disposed adjacent to or in close proximity to ring gear 266 and defines an aperture 254d' therethrough. Aperture 254d' is sized and formed in first plate 254a' so as to be aligned with second proximal drive shaft 214 and to permit second proximal drive shaft 214 to freely rotate therewithin. Second plate 254b' is spaced from first plate 254a' so as to be disposed at a distal free end of second proximal drive shaft 214. Second plate 254b' defines an aperture 254e' therethrough. Aperture 254e' is sized and formed in second plate or flange 254b' so as to be aligned with second proximal drive shaft 214 and to rotatably receive a distal tip 214c of second proximal drive shaft 214.

In this manner, distal tip 214c of second proximal drive shaft 214 is supported and prevented from moving radially away from a longitudinal rotational axis of second proximal drive shaft 214 as second proximal drive shaft 214 is rotated to axially translate articulation bearing assembly 252.

Figure 38:
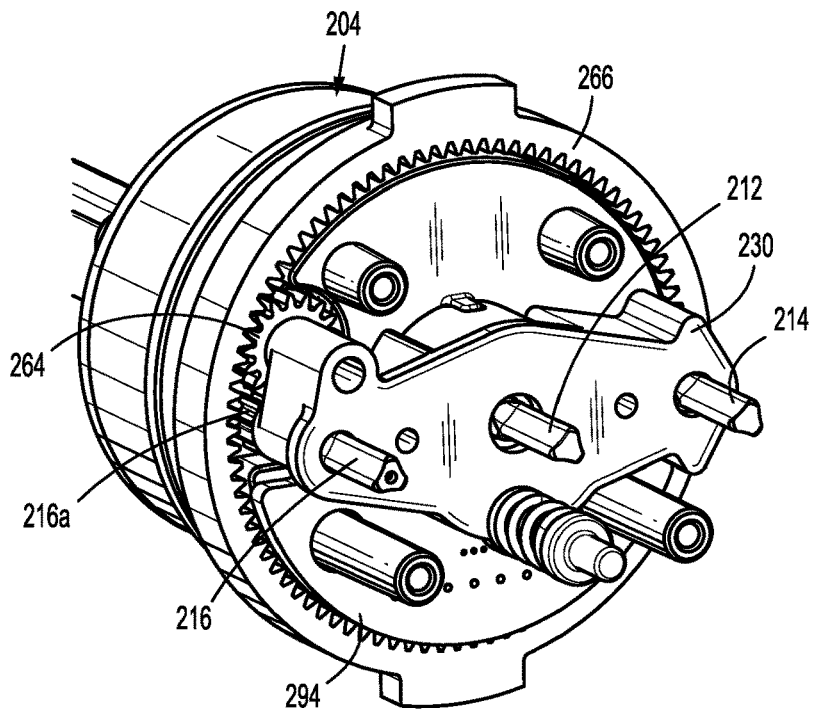
FIG. 38 is a rear, perspective view of the proximal inner housing assembly of FIG. 37 with connector sleeves removed therefrom.
Figure 39:
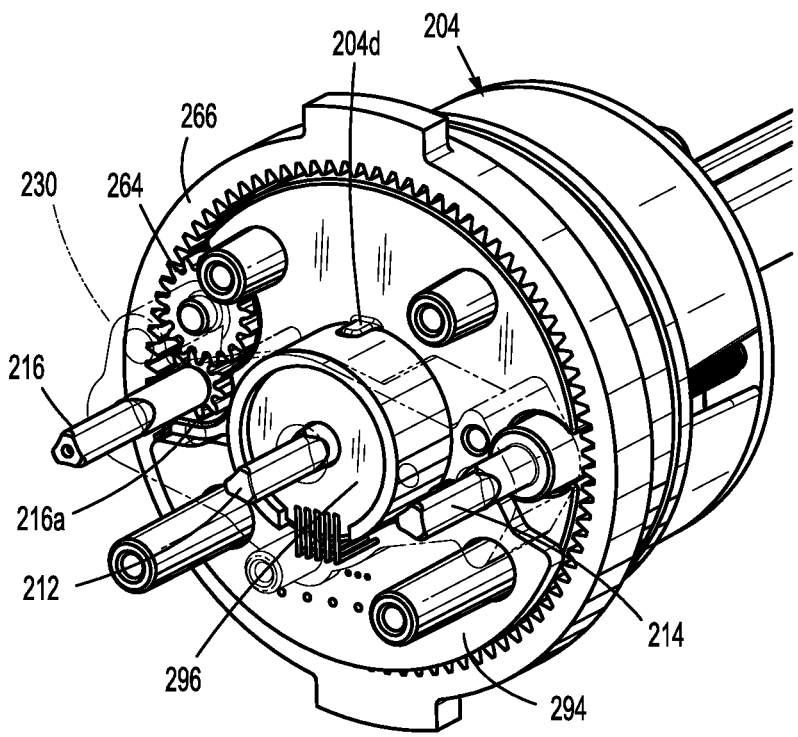
FIG. 39 is a rear, perspective view of the proximal inner housing assembly of FIG. 37 with connector sleeves removed therefrom and the plate bushing shown in phantom.

As illustrated in FIGS. 38, 46 and 47, inner housing assembly 204' may include a reinforcing sleeve 255' disposed about bracket assembly 254' to further reinforce bracket assembly 254'. It is contemplated in an embodiment that reinforcing sleeve 255' may be interposed between first plate 254a' and second plate 254b' of bracket assembly 254'. It is further contemplated that reinforcing sleeve 255' may be interposed between second plate 254b' and a distally oriented face of proximal inner housing assembly 204'.

Turning now to FIGS. 49-53, a force/rotation transmitting/converting assembly 350, according to another embodiment of the present disclosure, is shown and will be described. Force/rotation transmitting/converting assembly 350 is similar to the second force/rotation transmitting/converting assembly 250 and is only described herein to the extent necessary to describe the differences in construction and operation thereof. Likewise, another embodiment of an articulation bearing assembly is shown generally as 352. Articulation bearing assembly 352 is similar to articulation bearing assembly 252 and is only described herein to the extent necessary to describe the differences in construction and operation thereof.

Figure 49:
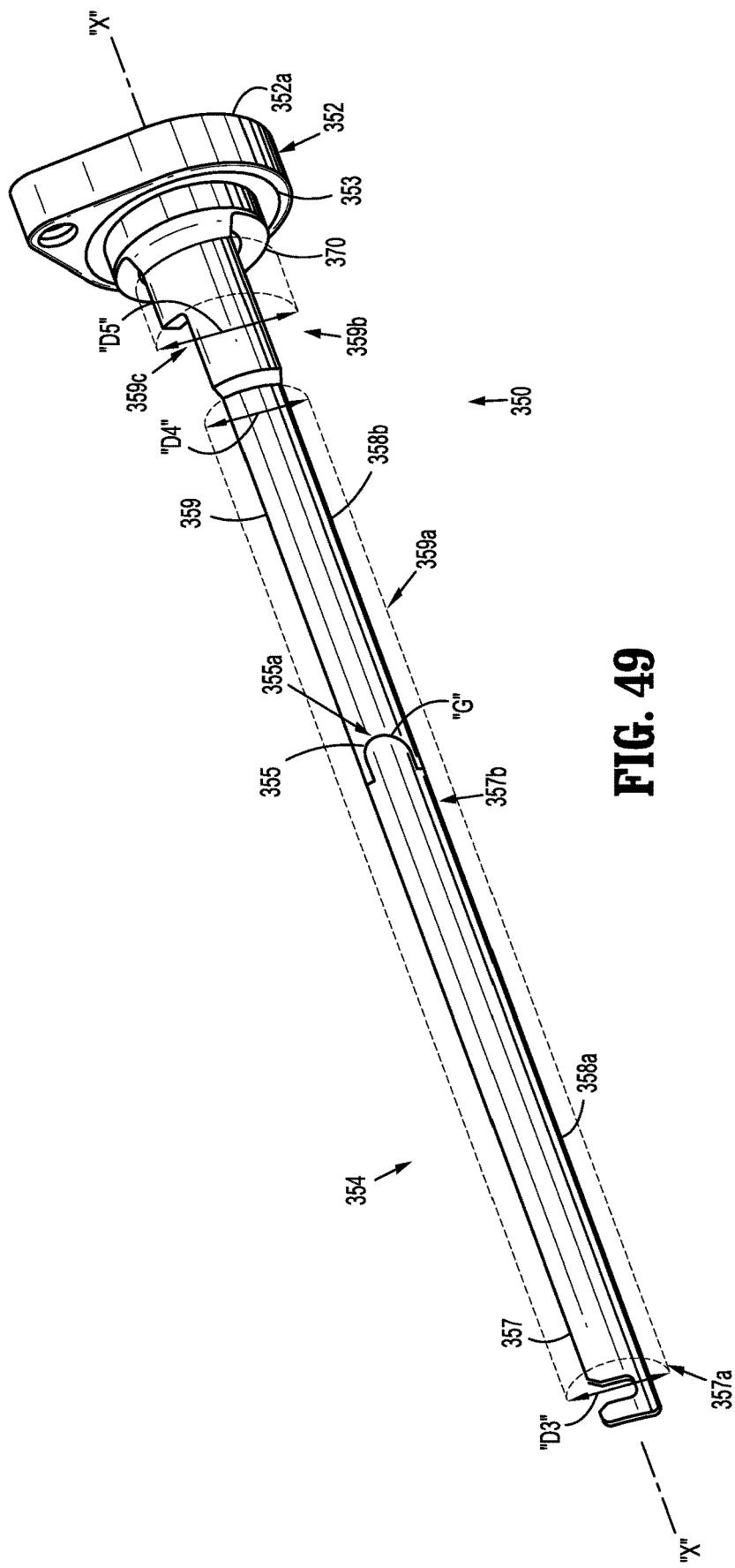
FIG. 49 is a perspective view of an alternative embodiment of an articulation assembly of the adapter assembly of FIGS. 2A and 2B.
Figure 50:
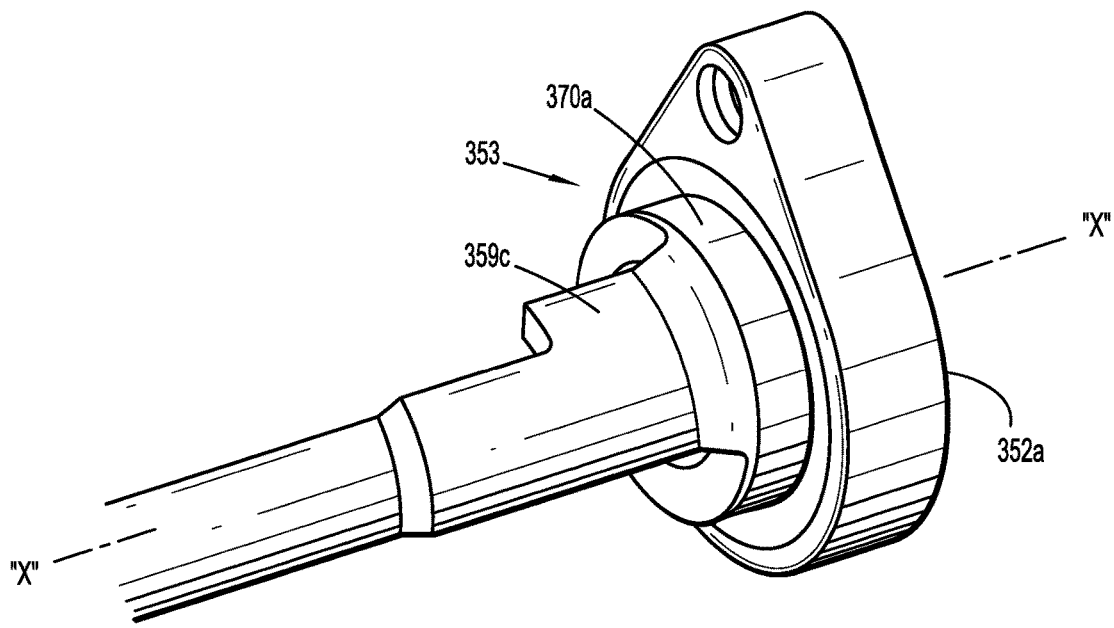
FIG. 50 is a perspective view of a bearing assembly of the articulation assembly of FIG. 49.
Figure 52:
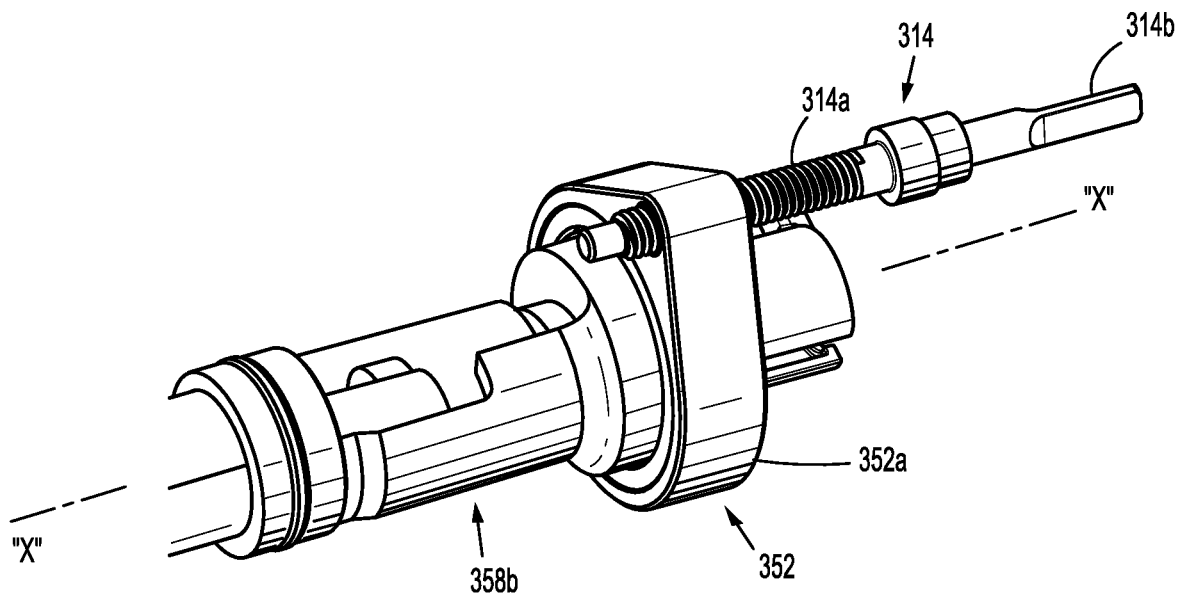
FIG. 52 is a perspective view of the bearing assembly of FIG. 50 including a proximal drive shaft.

With reference to FIGS. 49 and 52, force/rotation transmitting/converting assembly 350 includes a distal force transmitting member 354 and a proximal drive shaft 314. Proximal drive shaft 314 is rotatably supported within an inner housing assembly 312 (see FIG. 53). Proximal drive shaft 314 includes a distal portion 314a having a threaded outer profile or surface and a non-circular proximal portion 314b configured for mating with a respective drive connector 120 of surgical device 100 (see FIG. 1B).

Distal force transmitting member 354 includes, an articulation bearing assembly 352, a distal articulation bar 358a, a proximal articulation bar 358b, and a collar 370. Articulation bearing assembly 352 includes a bearing housing 352a supporting an articulation bearing 353. In embodiments, bearing housing 352a has a non-circular outer profile, such as, for example, a tear-drop shape.

Figure 57:
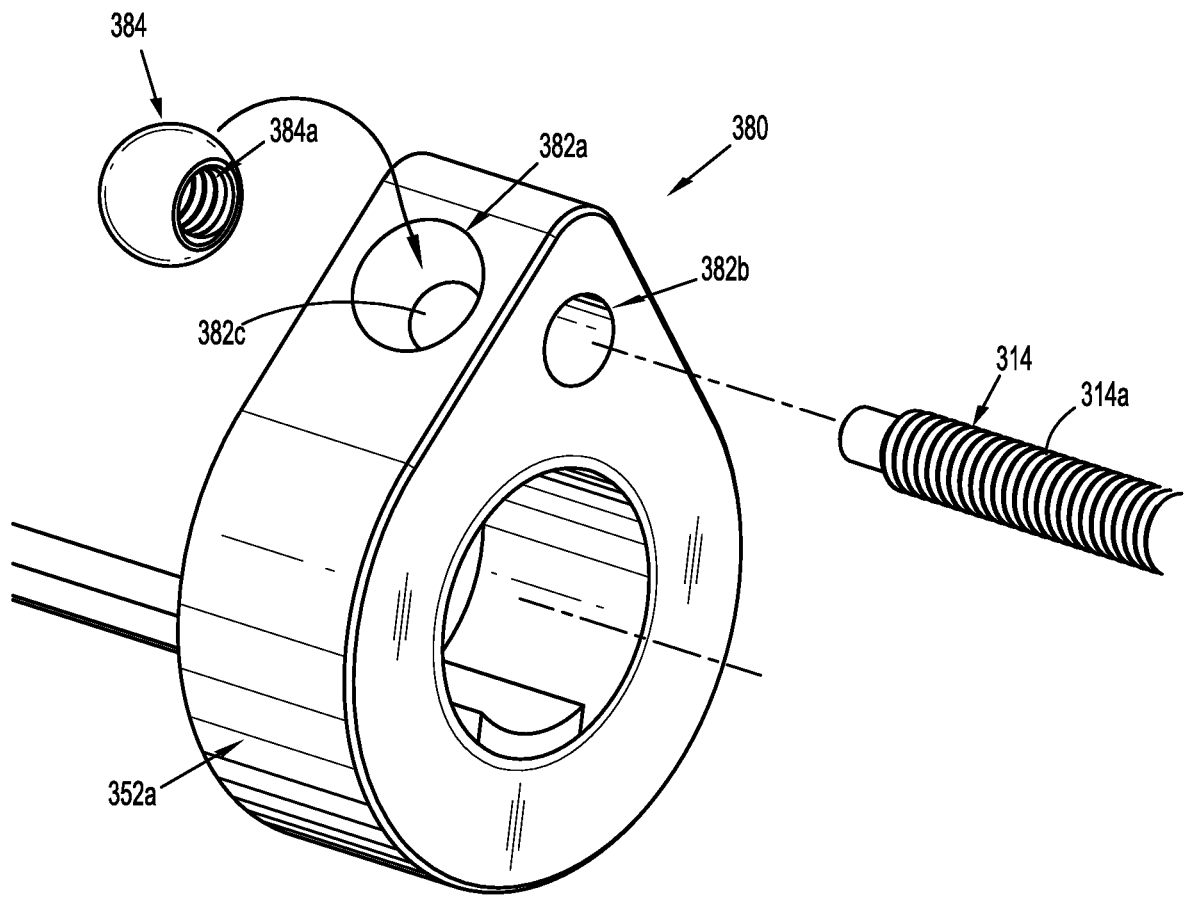
FIG. 57 is a rear perspective view of yet another alternative embodiment of a bearing assembly similar to those shown in FIGS. 50 and 55.

In embodiments such as the one shown in FIG. 57, bearing housing 352a includes a racking assembly 380. Racking assembly 380 includes a first through hole 382a and a second through hole 382b. First and second through holes 382a, 382b intersect to define a cavity 382c in bearing housing 352a. Cavity 382c is configured to house a ball 384 having a threaded bore 384a formed therein. The threaded bore 384a of ball 384 is configured to threadably connect to the threaded distal portion 314a of the proximal drive shaft 314. In this embodiment, bearing housing 352a is able to or free to rack during actuation of the force/rotation transmitting/converting assembly 350 without the stress from the racking being transferred to the proximal drive shaft 314, thereby preventing bending of the proximal drive shaft 314.

Figure 51:
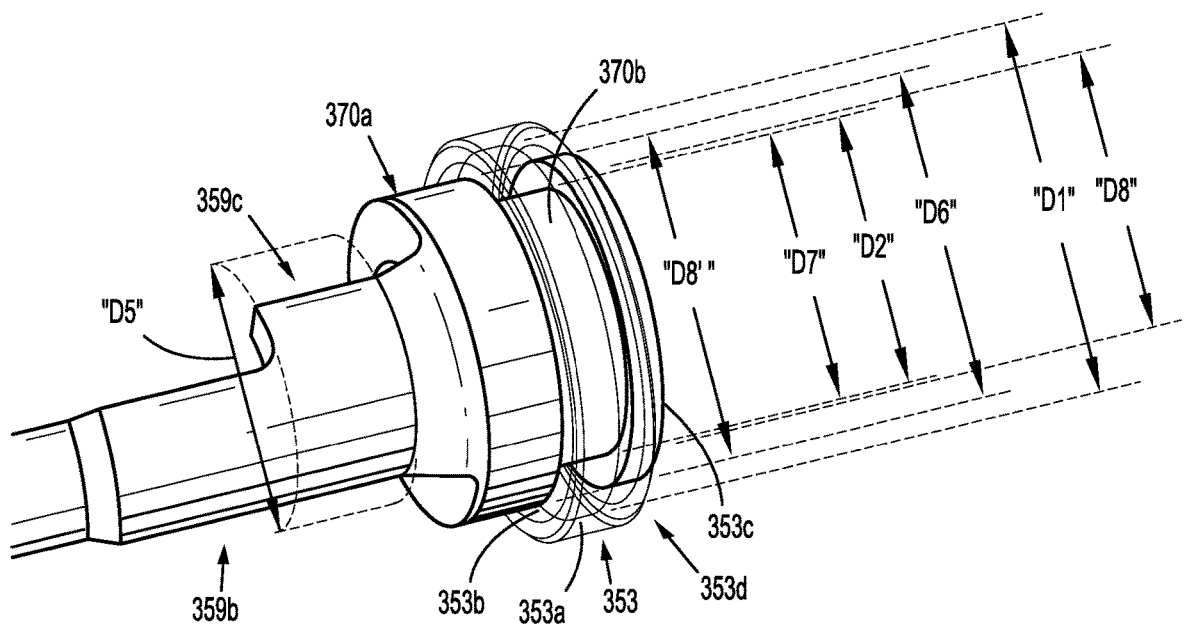
FIG. 51 is a perspective, cutaway view of the bearing assembly of FIG. 50, with a bearing housing removed therefrom.

With reference momentarily to FIG. 51, articulation bearing 353 includes an inner race 353b that is independently rotatable relative to an outer race 353a about the longitudinal axis "X." In embodiments, outer race 353a and inner race 353b each defines a circular cross-section having an inner diameter of "D1" and "D2" respectively, wherein inner diameter "D1" is greater than "D2."

With reference back to FIG. 49, distal articulation bar 358a includes a body portion 357 extending along longitudinal axis "X" between a distal end 357a and a proximal end 357b. Similarly, proximal articulation bar 358b includes a body portion 359 extending along longitudinal axis "X" between a distal end 359a and a proximal end 359b. Body portion 357 of the distal articulation bar 358a includes an outer diameter "D3." Similarly, body portion 359 of the proximal articular bar 358b includes an outer diameter "D4," wherein outer diameter "D3" is equal to outer diameter "D4."

In embodiments as shown in FIG. 49, distal end 359a of the proximal articulation bar 358a defines a cut out 355 shaped for mating with the proximal end 357b of the distal articulation bar 358a. This enables distal end 359a of proximal articulation bar 358b to connect to the proximal end 357b of the distal articulation bar 358a. In embodiments, distal end 359a of proximal articulation bar 358b is welded to proximal end 357b of the distal articulation bar 358a. However, it is envisioned that the distal and proximal articulation bars 358a, 358b may be fixedly connected using adhesives. In embodiments, cut out 355 is shaped such that there is a gap "G" between the proximal end 357b of the distal articulation bar 358a and a proximal portion 355a of cut out 355. Gap "G" enables distal end 357a of the distal articulation bar 358a to be spaced from the articulation bearing 353 with greater accuracy and repeatability within the tolerance.

Proximal articulation bar 358b further includes a transition portion 359c extending proximally from proximal articulation bar 358b. Transition portion 359c includes an outer diameter "D5," wherein outer diameter "D5" is greater than outer diameter "D3" and outer diameter "D4." As shown in FIG. 49, transition portion 359c abuts collar 370. In effect, proximal articulation bar 358b includes a body portion 359 that extends proximally to transition portion 359c, which extends proximally to collar 370.

As shown in FIG. 51, collar 370 of distal force transmitting member 354 includes a first portion 370a having a first outer diameter "D6" and a second portion 370b having a second outer diameter "D7," wherein first outer diameter "D6" is greater than second outer diameter "D7." In embodiments, second portion 370b is correspondingly sized with the inner race 353b of the articulation bearing 353 such that the second portion 370b of collar 370 engages an inner surface (not shown) of inner race 353b of the articulation bearing 353. In these embodiments, first portion 370a of collar 370 is larger than the inner race 353b of the articulation bearing 353 such that only the second portion 370b of collar 370 mates with the inner race 353b of articulation bearing 353.

In some embodiments, collar 370 is affixed to articulation bearing 353 by welding second portion 370b of collar 370 to inner race 353b of articulation bearing 353. In embodiments, a washer 353c is welded to a proximal end 353d of the articulation bearing 353 to further secure collar 370 to articulation bearing 353. As shown in FIG. 51, washer 353c has an outer diameter "D6'" equal to the first outer diameter "D6" of the first portion 370a of collar 370a. Washer 353c has an inner diameter "D8" which is greater than the second outer diameter "D7" of the second portion 370b of collar 370 such that the second portion 370b of collar 370 engages an inner surface (not shown) of washer 353c. It is envisioned that washer 353c can be secured to the proximal end 353d of the articulation bearing 353 and second portion 370b of collar 370 using adhesives or other securing means.

Continuing with FIG. 51, outer diameter "D5" of the transition portion 359c and first outer diameter "D6" of the first portion 370a of collar 370 are both greater than outer diameter "D4" of body portion 359. In embodiments, outer diameter "D5" of the transition portion 359c is less than outer diameter "D6" of the first portion 370a of collar 370. However, in alternate embodiments, outer diameter "D5" may be equal to outer diameter "D6." In operation, the larger outer diameter "D6" of the first portion 370a of collar 370 enables proximal articulation bar 358b to resist bending as the force/rotation transmitting/converting assembly 350 converts and transmits a rotation of the proximal drive shaft 314 to an axial translation of the loading unit 300 (FIG. 48). This relationship is determined by the equation:

$$F_B = MR/I$$

where "M" is the moment, "R" is the radius of the object resisting the force, and "I" is the moment of inertia.

Figure 53:
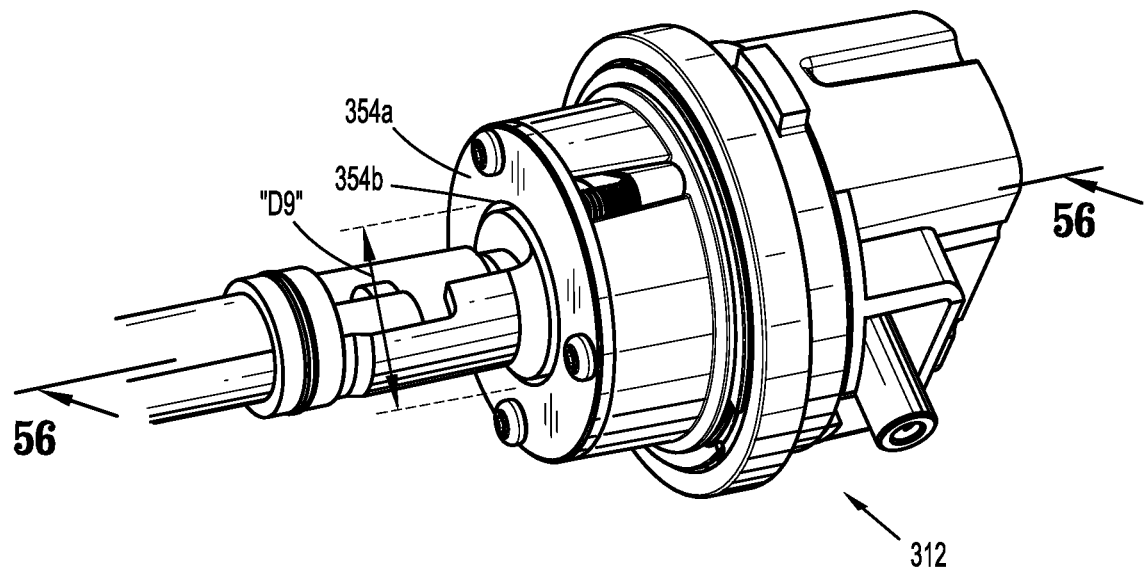
FIG. 53 is a perspective view of an alternative embodiment of an inner housing assembly similar to that shown in FIG. 16 with the outer knob housing and the proximal inner housing removed therefrom.

With reference to FIG. 53, force/rotation transmitting/converting assembly 350 further includes an articulation plate 354a configured to secure the distal force transmitting member 354 within the inner housing assembly 312. Articulation plate 354a defines a through hole 354b having a diameter "D9" configured for locating and supporting the first portion 370a of collar 370. The diameter "D9" of the through hole 354b of the articulation plate 354a is greater than the first outer diameter "D6" of the first portion 370a of the collar 370 such that the mating of articulation plate 354a and collar 370 reinforces collar 370 to resist bending of the proximal articulation bar 358b.

Figure 54:
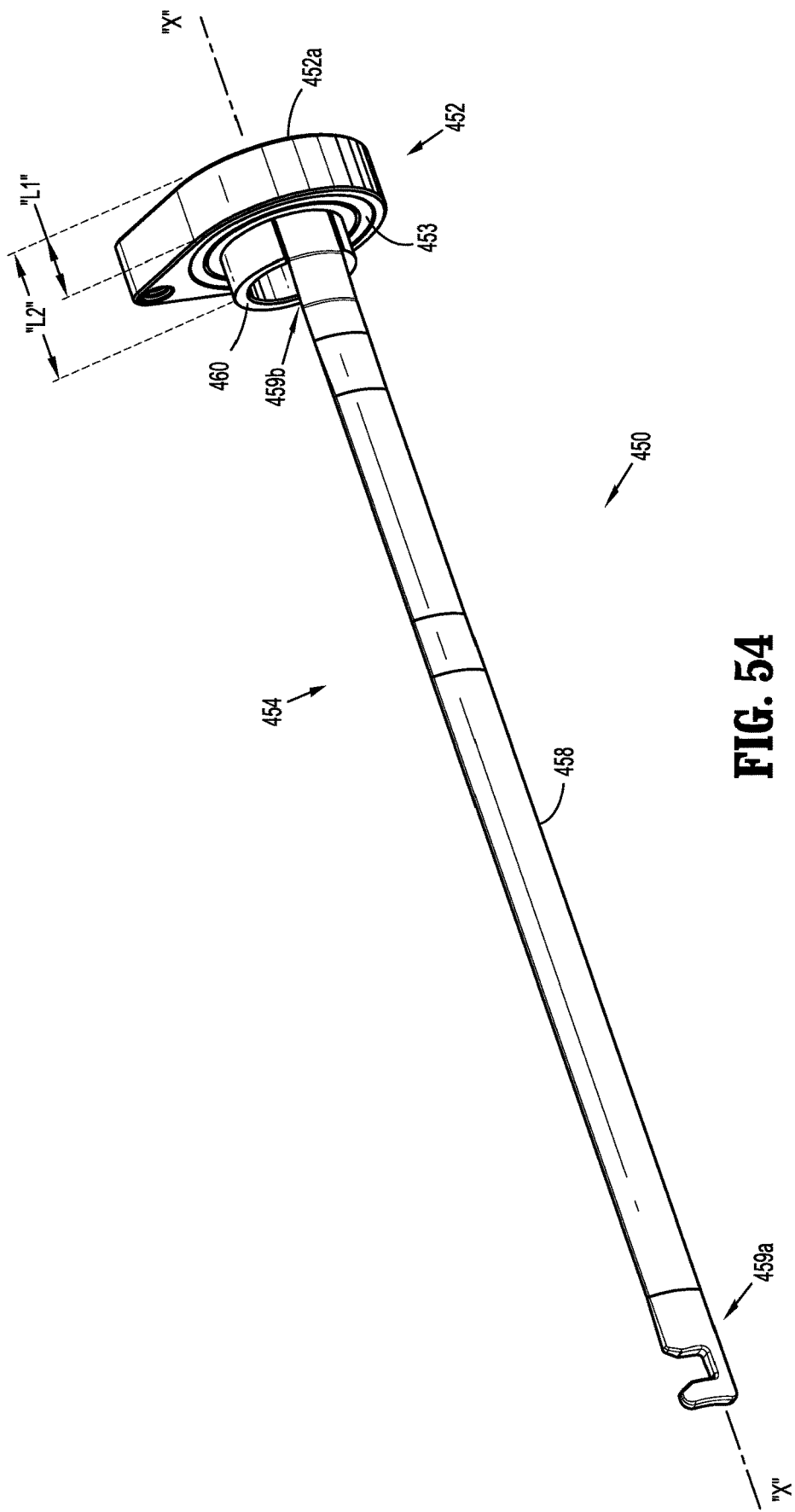
FIG. 54 is a perspective view of another alternative embodiment of an articulation assembly of the adapter assembly of FIGS. 2A and 2B.
Figure 55:
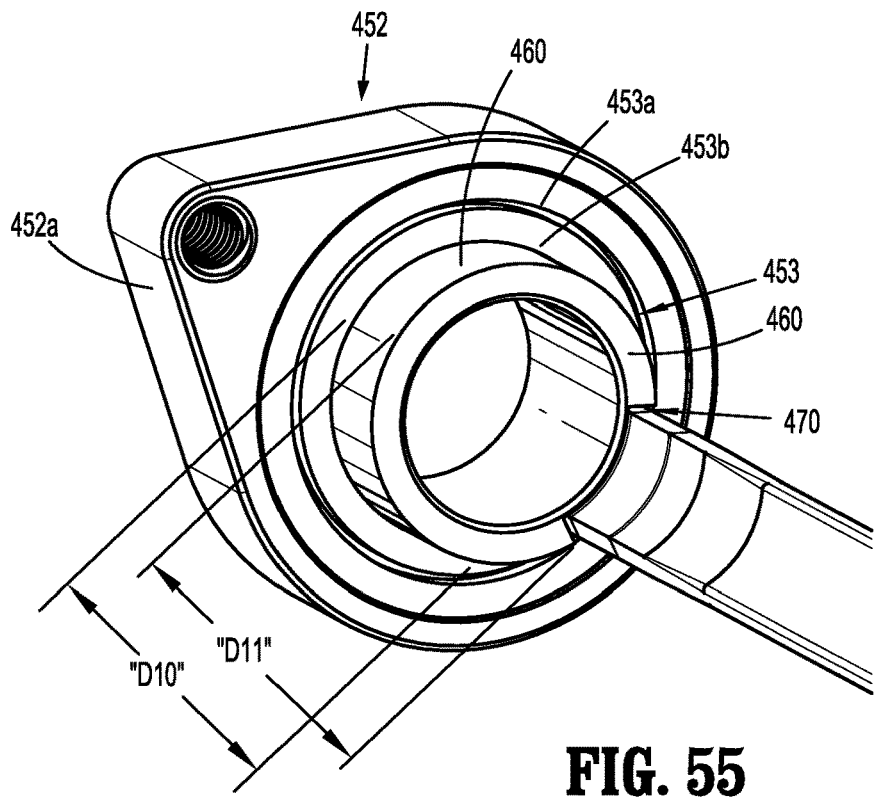
FIG. 55 is a perspective view of a bearing assembly of the articulation assembly of FIG. 54.
Figure 56:
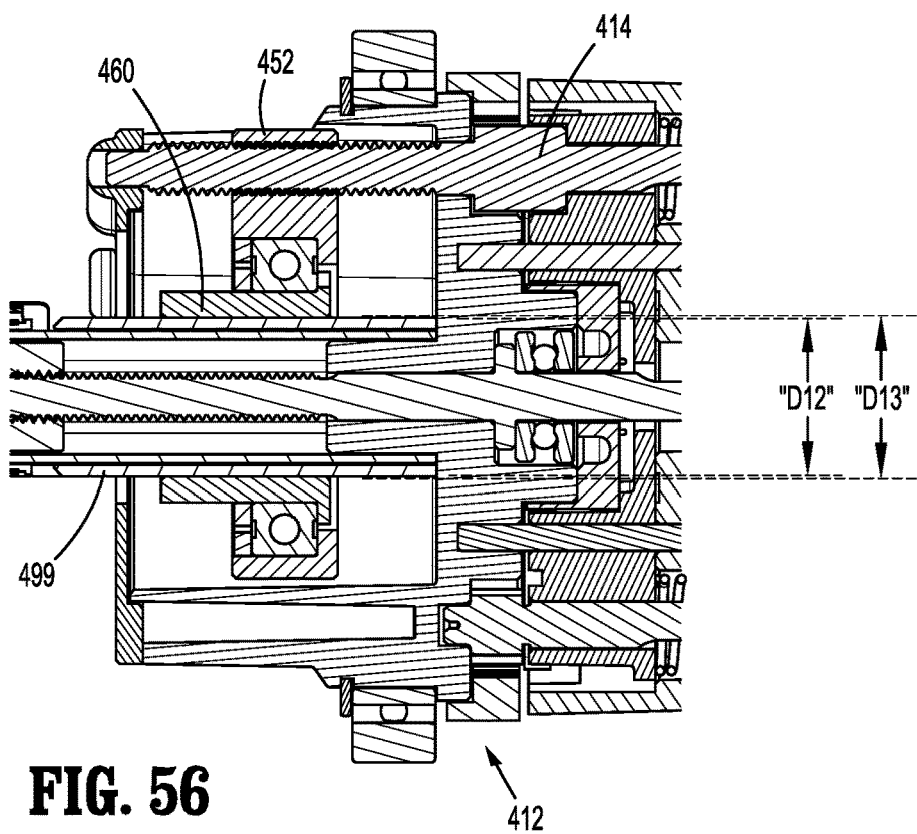
FIG. 56 is a cross-sectional view of an inner housing assembly similar to that shown in FIG. 53 taken along section line 56-56 of FIG. 53.

Turning now to FIGS. 54-56, a force/rotation transmitting/converting assembly 450, according to another embodiment of the present disclosure, is shown and will be described. Force/rotation transmitting/converting assembly 450 is similar to the second force/rotation transmitting/converting assembly 250, 350 and is only described herein to the extent necessary to describe the differences in construction and operation thereof. Likewise, another embodiment of an articulation bearing assembly is shown generally as 452. Articulation bearing assembly 452 is similar to articulation bearing assembly 252, 352 and is only described herein to the extent necessary to describe the differences in construction and operation thereof.

With reference to FIG. 55, distal force transmitting member 454 includes, an articulation bearing assembly 452, an articulation bar 458, and an inner sleeve 460. Articulation bearing assembly 452 includes a bearing housing 452a supporting an articulation bearing 453. Articulation bearing 453 includes an inner race 453b that is independently rotatable relative to an outer race 453a. Outer race 453a and inner race 453b each defines a circular cross-section.

In some embodiments, bearing housing 452a has a non-circular outer profile, such as, for example, a tear-drop shape. In embodiments, the bearing housing 452a includes a racking assembly 380 (FIG. 57) similar to the one described above with reference to bearing housing 352a. In this embodiment, racking assembly 380 enables bearing housing 452a to rack during actuation of the force/rotation transmitting/converting assembly 450 without the stress from the racking being transferred to the proximal drive shaft 414, thereby preventing bending of the proximal drive shaft 414.

Articulation bar 458 extends along longitudinal axis "X" between a distal portion 459a and a proximal portion 459b. Distal portion 459a of the articulation bar 458 is configured to connect to articulation link 366 (FIG. 48) of loading unit 300. As will be discussed in greater detail below, proximal portion 459b of the articulation bar 458 is disposed between the inner race 453b of the articulation bearing 453 and the inner sleeve 460.

Inner sleeve 460 extends axially beyond the articulation bearing 453. For example, the articulation bearing 453 may define a length "L1," and inner sleeve 460 may define a length "L2," wherein length "L1" is less than length "L2." It is envisioned that the longer aspect ratio of the inner sleeve 460 relative to the articulation bearing 453 will reduce bending of the articulation bar 458 as it rotates about the longitudinal axis "X" relative to the articulation bearing 453. Though the figures show inner sleeve 460 extending distally from articulation bearing 453, it is envisioned that inner sleeve 460 may also extend proximally from articulation bearing 453.

As shown in FIG. 55, inner sleeve 460 is supported within inner race 453b of articulation bearing 453. Accordingly, inner race 453b defines an inner diameter "D10" and inner sleeve 460 defines an outer diameter "D11," wherein inner diameter "D10" is greater than outer diameter "D11" such that an outer surface 460a of inner sleeve 460 abuts an inner surface (not shown) of inner race 453b.

In embodiments, the outer surface 460a of inner sleeve 460 defines a slot 470 shaped for disposal of the proximal portion 459b of the articulation bar 458, e.g., proximal portion 459b of the articulation bar 458 is disposed in slot 470 between inner sleeve 460 and inner race 453b. To secure the proximal portion 459b of the articulation bar 458 to the articulation bearing 453, the proximal portion 459b of the articulation bar 458 is welded into the slot 470. However, in embodiments, any appropriate means, such as for example, adhesives may be used to secure the articulation bar 458 to the articulation bearing 453. In embodiments, there may be a gap (not shown) between the proximal portion 459b of the articulation bar 458 and a proximal face (not shown) of the slot 470 on the outer surface 460a of the inner sleeve 460. It is envisioned that the gap would enable a manufacturer to space the articulation bar 458 in relation to the articulation bearing 453 with greater accuracy and repeatability.

With reference to FIG. 56, an inner housing assembly 412, similar to inner housing assembly 312, is shown. Inner housing assembly 412 includes an electrical assembly 490 similar to electrical assembly 290. The electrical assembly 490 includes a slip ring cannula 499 supported within inner sleeve 460 to protect and/or shield any wires extending through slip ring cannula 499. Slip ring cannula 499 has an outer diameter "D12" which is less than an inner diameter "D13" of the inner sleeve 460 such that the slip ring cannula 499 engages the inner sleeve 460 utilizing an interference fit.

Figure 58:
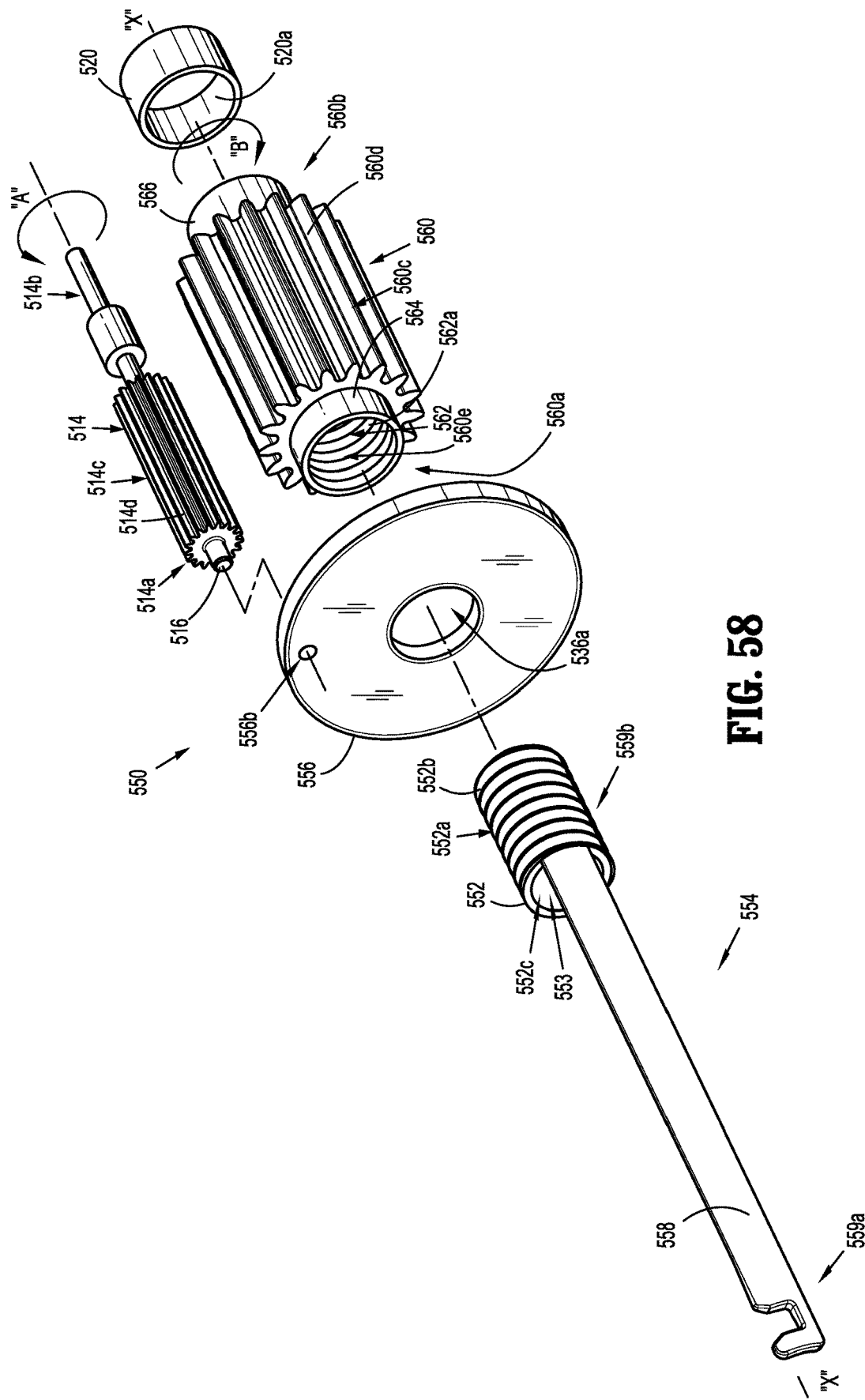
FIG. 58 is a perspective view of still another alternative embodiment of an articulation assembly of the adapter assembly of FIGS. 2A and 2B.

Turning now to FIG. 58, a force/rotation transmitting/converting assembly 550 according to another embodiment of the present disclosure is shown and will be described. Force/rotation transmitting/converting assembly 550 is similar to the second force/rotation transmitting/converting assembly 250, 350, and 450 and is only described herein to the extent necessary to describe the differences in construction and operation thereof.

Force/rotation transmitting/converting assembly 550 includes a proximal rotation receiving member, such as, for example, a proximal drive shaft 514 engagable with a respective rotatable drive shaft (not shown) of the surgical device 100, a driver 560, and a distal force transmitting member 554. The proximal drive shaft 514 extends along longitudinal axis "X" between a distal portion 514a and a proximal portion 514b. The proximal drive shaft 514 member includes an outer surface 514c defining a plurality of spur gears 514d extending along the longitudinal axis "X."

The driver 560 extends along longitudinal axis "X" between a distal portion and 560a and a proximal portion 560b. The driver 560 includes an outer surface 560c defining a plurality of spur gears 560d extending along the longitudinal axis "X" where the plurality of spur gears 560d of the driver 560 are configured to engage the plurality of spur gears 514d of the proximal drive shaft 514. Accordingly, when the proximal drive shaft 514 is rotated relative to the driver 560 about the longitudinal axis "X" in a direction given by arrow "A," the driver 560 is rotated in the opposite direction relative to the proximal drive shaft 514 about the longitudinal axis "X" given by arrow "B."

With continued reference to FIG. 58, driver 560 includes an inner surface 560e defining a bore 562 therethrough. The bore 562 defines a plurality of threads 562a. Distal portion 560a of the driver 560 defines a protrusion, such as, for example, a distal boss 564. Similarly, proximal portion 560b of the driver 560 defines a protrusion, such as, for example, a proximal boss 566.

An inner housing assembly (not shown) similar to inner housing assembly 312 and 412, includes a distal articulation plate 556 defining a first through hole 556a configured for locating the distal boss 564 of the driver 560. When distal boss 564 is mounted into the first through hole 556a of the distal articulation plate 556, the driver 560 is co-axial to the longitudinal axis "X." Distal articulation plate 556 also includes a second through hole 556b configured for locating and supporting a distal protrusion 516 extending from the distal portion 514a of the proximal drive shaft 514.

When the distal boss 564 of the driver 560 is located in the first through hole 556a and the distal protrusion 516 of the proximal drive shaft 514 is located in the second through hole 556b, the plurality of spur gears 560d of the driver 560 are engagable with the plurality of spur gears 514d of the proximal drive shaft 514. The housing (not shown) also includes a proximal core portion 520 configured for locating the proximal boss 566 of the driver 560. The proximal core portion 520 includes a through hole 520a configured to locate the proximal boss 566 of the driver 560 such that the driver 560 is co-axial to longitudinal axis "X."

Continuing with reference to FIG. 58, the distal force transmitting member 554 includes a sleeve 552 and an articulation bar 558. Sleeve 552 includes an outer surface 552a defining a plurality of threads 552b configured to engage with the plurality of threads 562a defined in the bore 562 of the driver 560. Sleeve 552 also includes an inner surface 552c defining a bore 553 therethrough. Articulation bar 558 extends along longitudinal axis "X" between a distal portion 559a and a proximal portion 559b. The proximal portion 559b of the articulation bar is secured to the inner surface 552c of the sleeve 552 such that when the sleeve is threadingly connected to the driver 560, the articulation bar 558 is co-axial to longitudinal axis "X."

In operation, as the proximal drive shaft 514 is rotated about the longitudinal axis "X" in the direction given by arrow "A," the plurality of spur gears 514d engages the plurality of spur gears 560d of the driver 560 to rotate driver 560 about the longitudinal axis "X" in the direction given by arrow "B." As driver 560 rotates, the sleeve 552 of the distal force transmitting member 554 is axially translated, resulting in axial translation of the loading unit 300 of surgical device 100.

In accordance with the present disclosure, an overall length of adapter assembly 200 has been reduced as compared to prior adapter assemblies that have been developed to transmit/convert forces/rotations from surgical device 100 to loading unit 300. By reducing an overall length of adapter assembly 200, a center of gravity of an assembled surgical device 100, adapter assembly 200 and loading unit 300 has been shifted proximally as compared to a center of gravity of an assembled surgical device 100, a prior adapter assembly and a loading unit 300. As such, a level of comfort to the end user in using the electromechanical surgical system of the present disclosure has been increased, and a level of fatigue has been decreased.

In operation, when a button of surgical device 100 is activated by the user, the software checks predefined conditions. If conditions are met, the software controls the motors and delivers mechanical drive to the attached surgical stapler, which can then open, close, rotate, articulate or fire depending on the function of the pressed button. The software also provides feedback to the user by turning colored lights on or off in a defined manner to indicate the status of surgical device 100, adapter assembly 200 and/or loading unit 300.

Reference may be made to U.S. Pat. No. 7,819,896, the entire contents of each of which are incorporated herein by reference, for a detailed discussion of the construction and operation of loading unit 300, as illustrated in FIGS. 1 and 48.

Any of the components described herein may be fabricated from either metals, plastics, resins, composites or the like taking into consideration strength, durability, wearability, weight, resistance to corrosion, ease of manufacturing, cost of manufacturing, and the like.

It will be understood that various modifications may be made to the embodiments of the presently disclosed adapter assemblies. Therefore, the above description should not be construed as limiting, but merely as exemplifications of embodiments. Those skilled in the art will envision other modifications within the scope and spirit of the present disclosure.

What is claimed is:

1. A force/rotation transmitting/converting assembly for interconnecting a drive shaft of a surgical device and an axially translatable drive member of a loading unit, wherein the force/rotation transmitting/converting assembly includes:

a bearing assembly having a first through hole and a second through hole, the first through hole and the second through hole intersecting to define a cavity configured for housing a ball having a threaded bore formed therein, the threaded bore configured for threadably connecting to a threaded portion of the drive shaft of the surgical device.

2. The force/rotation transmitting/converting assembly according to claim 1, wherein the bearing assembly includes an outer race connected to a distal end of the drive shaft of the surgical device.

3. The force/rotation transmitting/converting assembly according to claim 2, wherein the outer race is threadably connected to a threaded distal end of the drive shaft of the surgical device.

4. The force/rotation transmitting/converting assembly according to claim 1, wherein the threaded bore is configured for threadably connecting to a distal end of the drive shaft of the surgical device.

5. The force/rotation transmitting/converting assembly according to claim 1, wherein the bearing assembly includes an inner race and an outer race.

6. The force/rotation transmitting/converting assembly according to claim 5, further comprising an inner sleeve supported at least partially within the inner race of the bearing assembly and extending axially from the inner race.

7. A force/rotation transmitting/converting assembly for interconnecting a drive shaft of a surgical device and an axially translatable drive member of a loading unit, wherein the force/rotation transmitting/converting assembly includes:
- a receiving member that is connectable to a drive shaft of the surgical device, the receiving member including at least one spur gear;
- a driver including at least one spur gear configured for mating with the at least one spur gear of the receiving member, the driver defining a bore therethrough; and
- a force transmitting member that is connectable to a portion of the axially translatable drive member of the loading unit, the force transmitting member including:
  - a sleeve configured to mate with the driver;
  - an articulation bar configured to selectively engage the axially translatable drive member of the loading unit; and
  - a bearing assembly defining a cavity configured for housing a ball having a threaded bore formed therein, the threaded bore configured for threadably connecting to a threaded portion of the drive shaft of the surgical device.

8. The force/rotation transmitting/converting assembly according to claim 7, wherein the force/rotation transmitting/converting assembly converts and transmits a rotation of the drive shaft of the surgical device to a rotation of the driver such that the sleeve of the distal force transmitting member is axially translated resulting in an axial translation of the axially translatable drive member of the loading unit.

9. The force/rotation transmitting/converting assembly according to claim 7, wherein the bore of the driver defines at least one thread.

10. The force/rotation transmitting/converting assembly according to claim 9, wherein the sleeve includes at least one thread configured to mate with the at least one thread of the bore of the driver.

11. The force/rotation transmitting/converting assembly according to claim 7, wherein a proximal end of the articulation bar is secured to the sleeve.

12. The force/rotation transmitting/converting assembly according to claim 7, wherein the force transmitting member is connectable to an articulation link of the axially translatable drive member of the loading unit.

13. The force/rotation transmitting/converting assembly according to claim 7, wherein a proximal end of the articulation bar is secured to the sleeve, and wherein a distal end of the articulation bar is configured to selectively engage the axially translatable drive member of the loading unit.

14. The force/rotation transmitting/converting assembly according to claim 7, wherein the sleeve defines a bore therethrough which defines an inner surface, and wherein a proximal end of the articulation bar is secured to the inner surface of the sleeve.

* * * * *